US010654907B2

(12) United States Patent
Hirano et al.

(10) Patent No.: US 10,654,907 B2
(45) Date of Patent: May 19, 2020

(54) METHODS AND COMPOSITIONS FOR PRODUCING A CELL EXPRESSING A T CELL RECEPTOR

(71) Applicant: UNIVERSITY HEALTH NETWORK, Toronto (CA)

(72) Inventors: Naoto Hirano, Toronto (CA);
Munehide Nakatsugawa, Sapporo (JP);
Toshiki Ochi, Toon (JP)

(73) Assignee: University Health Network, Toronto (CA)

( * ) Notice: Subject to any disclaimer, the term of this patent is extended or adjusted under 35 U.S.C. 154(b) by 612 days.

(21) Appl. No.: 15/111,639

(22) PCT Filed: Jan. 28, 2015

(86) PCT No.: PCT/CA2015/000049
§ 371 (c)(1),
(2) Date: Jul. 14, 2016

(87) PCT Pub. No.: WO2015/113140
PCT Pub. Date: Aug. 6, 2015

(65) Prior Publication Data
US 2016/0340403 A1 Nov. 24, 2016

Related U.S. Application Data

(60) Provisional application No. 61/933,048, filed on Jan. 29, 2014.

(51) Int. Cl.
*C07K 14/725* (2006.01)
*C12N 15/10* (2006.01)
*C12N 5/078* (2010.01)

(52) U.S. Cl.
CPC ........ *C07K 14/7051* (2013.01); *C12N 5/0634* (2013.01); *C12N 15/1034* (2013.01); *C12N 15/1055* (2013.01); *C12N 15/1037* (2013.01); *C12N 2510/00* (2013.01)

(58) Field of Classification Search
CPC .............. C07K 14/7051; C12N 5/0634; C12N 15/1034; C12N 15/1055; C12N 2510/00
USPC ................. 435/325, 372, 69.6, 7.24
See application file for complete search history.

(56) References Cited

U.S. PATENT DOCUMENTS

| 8,119,772 | B2 | 2/2012 | Yang et al. | |
| 9,296,807 | B2 | 3/2016 | Mineno et al. | |
| 10,081,663 | B2 * | 9/2018 | Eisenbach | C07K 14/7051 |
| 2009/0226404 | A1 | 9/2009 | Schuler et al. | |
| 2014/0065111 | A1 * | 3/2014 | Eisenbach | C07K 14/7051 |
| | | | | 424/93.21 |

FOREIGN PATENT DOCUMENTS

| WO | 2010089412 | | 8/2010 |
| WO | 2012/040012 | A1 | 9/2011 |
| WO | 2012154858 | | 8/2012 |
| WO | 2013/177247 | A1 | 5/2013 |

OTHER PUBLICATIONS

Yamada-Ohnishi et al. (2004) Stem Cell and Development, vol. 13, 315-322.*
Zheng et al. (1989) PNAS, vol. 86, 3758-3762.*
Thomas et al. (2011) Blood, vol. 118(2), 319-329.*
H J Stauss et al., Immunotherapy with gene-modified T cells: Limiting side effects provides new challenges. Jun. 27, 2013; vol. 20, No. 11: 1029-1032, Gene Therapy, GB.
Linnemann C. et al., T-Cell Receptor Gene Therapy: Critical Parameters for Clinical Success, Journal of Investigative Dermatology. Jun. 16, 2011; vol. 131, No. 9: 1806-1816, US.
Uttenthal B J. et al., Challenges in T cell receptor gene therapy, Journal of Gene Medicine. Jun. 1, 2012; vol. 14, No. 6: 386-399. John Wiley & Songs, Inc, US.
T. Ochi et al., Optimization of T-Cell Reactivity by Exploiting TCR Chain Centricity for the purpose of Safe and Effective Antitumor TCR Gene Therapy, Gene Therapy, Cancer Immunology Research. Sep. 1, 2015; vol. 3, No. 9: 1070-1081, US.
Kunert A. et al., TCR-Engineered T Cells Meet New Challenges to Treat Solid Tumors: Choice of Antigen, T Cell Fitness, and Sensitization of Tumor Milieu, Front Immunol. Nov. 8, 2013; vol. 4: 363.
Hinrichs CS, et al., Exploiting the curative potential of adoptive T-cell therapy for cancer, Immunol Rev. 2014; vol. 257, No. 1:56-71.
Li et al., Directed evolution of human T-cell receptors with picomolar affinities by phage display. Nature Biotechnology, Mar. 2005, 349-354, vol. 23, No. 3.
Dietrich et al., Prevalent role of TCR alpha-chain in the selection of the preimmune repertoire specific for a human tumor-associated self-antigen. J Immunol. 2003, vol. 170, No. 10, 5103-9.
Trautmann et al., Dominant TCR Vα usage by virus and tumor-reactive T cells with wide affinity ranges for their specific antigens, Eur J Immunol. 2002, vol. 32, Issue 11: 3181-90.
Wei et al., The extent of the human germline T-cell receptor V beta gene segment repertoire. Immunogenetics. 1994, vol. 40, No. 1: 27-36.
Imataki et al., IL-21 can supplement suboptimal Lck-independent MAPK activation in a STAT-3-dependent manner in human CD8(+) T cells. J Immunol. 2012; 188(4):1609-19.

(Continued)

*Primary Examiner* — Anne Marie S Wehbe
(74) *Attorney, Agent, or Firm* — Bereskin & Parr LLP; Carmela De Luca; Amy Dam

(57) ABSTRACT

Provided is a method for determining a TCR polypeptide chain that can form a TCR specific for a peptide of interest. Also provided are methods and compositions for producing a cell expressing a T cell receptor (TCR) specific for a peptide of interest, methods and compositions for producing a TCR chain nucleic acid and/or pair of TCR chain polypeptides and/or nucleic acids encoding a TCR, a cell population comprising the cell harboring the nucleic acids encoding a TCR obtained by said method, and a method for treating a disorder comprising administering to the subject said cell population.

17 Claims, 35 Drawing Sheets

Specification includes a Sequence Listing.

(56) References Cited

OTHER PUBLICATIONS

Schultz ES, Lethe B, Cambiaso CL, Van Snick J, Chaux P, Corthals J, Heirman C, Thielemans K, Boon T, van der Bruggen P. A MAGE-A3 peptide presented by HLA-DP4 is recognized on tumor cells by CD4+ cytolytic T lymphocytes. Cancer Res. Nov. 15, 2000; 60: 6272-6275. (PMID: 1 1 103782).

Vigneron N, Ooms A, Morel S, a W, Degiovanni G, Van den Eynde B. A peptide derived from melanocytic protein gp100 and presented by HLA-B35 is recognized by autologous cytolytic T lymphocytes on melanoma cells. Tissue Antigens 2005; 65: 156-162. (PMID: 15713214).

Tomita Y, Imai K, Senju S, Irie A, Inoue M, Hayashida Y, Shiraishi K, Mori T, Daigo Y, Tsunoda T, Ito T, Nomori H, Nakamura Y, Kohrogi H, Nishimura Y. A novel tumor-associated antigen, cell division cycle 45-like can induce cytotoxic T-lymphocytes reactive to tumor cells. Cancer Sci; Apr. 2011, 102: 697-705. (PMID: 21231984).

Vigneron N, Van den Eynde BJ. Proteasome subtypes and the processing of tumor antigens: increasing antigenic diversity. Curr. Opin Immunol 2012; 24: 84-91 . (PMID: 22206698).

Ma W, Vigneron N, Chapiro J, Stroobant V, Germeau C, Boon T, Coulie PG, Van den Eynde BJ. A MAGE-C2 antigenic peptide processed by the immunoproteasome is recognized by cytolytic T cells isolated from a melanoma patient after successful immunotherapy. Int J Cancer 2011; 129. 2427-2434. (PMID: 21207413).

Corbiere V, Chapiro J, Stroobant V, Ma W, Lurquin C, Lethe B, van Baren N, Van den Eynde BJ, Boon T, Coulie PG. Antigen spreading contributes to MAGE vaccination-induced regression of melanoma metastases. Cancer Res 2011; 71 : 1253-1262. (PMID: 21216894).

Dalet A, Stroobant V, Vigneron N, Van den Eynde BJ. Differences in the production of spliced antigenic peptides by the standard proteasome and the immunoproteasome. Eur J Immunol. 2011; 41 : 39-46. (PMID: 21 182075).

Chapiro J, Claverol S, Piette F, Ma W, Stroobant V, Guillaume B, Gairin J-E, Morel S, Burlet-Schiltz O, Monsarrat B, Boon T, Van den Eynde B. Destructive cleavage of antigenic peptides either by the immunoproteasome or by the standard proteasome results in differential antigen presentation. J Immunol 2006; 176: 1053-1061. (PMID: 16393993).

Guillaume B, Chapiro J, Stroobant V, Colau D, Van Holle B, Parvizi G, Bousquet-Dubouch MP, Theate I, Parmentier N, Van den Eynde BJ. Two abundant proteasome subtypes that uniquely process some antigens presented by HLA class I molecules. Proc Natl Acad Sci U S A Oct. 26, 2010; vol. 107, No. 43: 18599-18604. (PMID: 20937868).

Dalet A, Robbins PF, Stroobant V, Vigneron N, Li YF, El-Gamil M, Hanada K, Yang JC, Rosenberg SA, Van den Eynde BJ. An antigenic peptide produced by reverse splicing and double asparagine deamidation. Proc Natl Acad Sci USA Jul. 19, 2011 ; vol. 108, No. 29: E323-331. (PMID: 21670269).

Vigneron N, Stroobant V, Chapiro J, Ooms A, Degiovanni G, Morel S, van der Bruggen P, Boon T, Van den Eynde B. An antigenic peptide produced by peptide splicing in the proteasome. Science Apr. 23, 2004; 304: 587-590. (PMID: 15001714).

Skipper JCA, Hendrickson RC, Gulden PH, Brichard V, Van Pel A, Chen Y, Shabanowitz J, Wolfel T, Slingluff CL, Jr, Boon T, Hunt DF, Engelhard VH. An HLA-A2-restricted tyrosinase antigen on melanoma cells results from posttranslational modification and suggests a novel pathway for processing of membrane proteins. J Exp Med Feb. 1996; 183: 527-534. (PMID: 8627164).

Hanada K, Yewdell JW, Yang JC. Immune recognition of a human renal cancer antigen through posttranslational protein splicing. Nature Jan. 15, 2004; 427: 252-256. (PMID: 14724640).

Chaux P, Vantomme V, Stroobant V, Thielemans K, Corthals J, Luiten R, Eggermont AM, Boon T, van der Bruggen P. Identification of MAGE-3 epitopes presented by HLA-DR molecules to CD4+ T lymphocytes. J Exp Med Mar. 1, 1999; vol. 189, No. 5: 767-777. (PMID: 10049940).

Zarour HM, Storkus WJ, Brusic V, Williams E, Kirkwood JM. NY-ESO-1 encodes DRB1 *0401—restricted epitopes recognized by melanoma-reactive CD4+ T cells. Cancer Res Sep. 1, 2000; 60: 4946-4952. (PMID: 10987311).

Parkhurst et al. Characterization of Genetically Modified T-Cell Receptors that Recognize the CEA:691-699 Peptide in the Context of HLA-A2.1 on Human Colorectal Cancer Cells. Clinical Cancer Research, Jan. 1, 2009, 15(1):169-80.

Theoret et al., Relationship of p53 overexpression on cancers and recognition by anti-p53 T cell receptor-transduced T cells. Human Gene Therapy, Nov. 2008, 19(11): 1219-32.

Kung P, Goldstein G, Reinherz EL, Schiossman SF. Monoclonal antibodies defining distinctive human T cell surface antigens. Science, vol. 206, pp. 347-349 (Oct. 1979).

Barker et al., Combined effect of total nucleated cell dose and HLA match on transplantation outcome in 1061 cord blood recipients with hematologic malignancies. Blood Mar. 4, 2010 115(9): 1843-9.

Haque et al., Allogeneic cytotoxic T-cell therapy for EBV-positive posttransplantation lymphoproliferative disease: results of phase 2 multicenter clinical trial. Blood 110(4) : 1123-31 (Aug. 15, 2007).

Li et al., Transgenic mice with a diverse human T cell antigen receptor repertoire. Nature Med. Sep. 2010, 16(9): 1029-34.

Barker et al., Successful treatment of EBV-associated posttransplantation lymphoma after cord blood transplantation using a third-party EBV-specific cytotoxic T lymphocytes. Blood, Dec. 2, 2010, 5045-5049, vol. 116, No. 23.

Robbins et al., Single and Dual Amino Acid Substitutions in TCR CDRs Can Enhance Antigen-Specific T Cell Functions. The Journal of Immunology, 2008, 6116-6131, vol. 180, No. 9.

Johnson et al., Gene Transfer of Tumor-Reactive TCR Confers Both High Avidity and Tumor Reactivity to Nonreactive Peripheral Blood Mononuclear Cells and Tumor-Infiltrating Lymphocytes. The Journal of Immunology, 2006, 6548-6559, vol. 177, No. 9.

Heemskerk et al., Redirection of antileukemic reactivity of peripheral T lymphocytes using gene transfer of minor histocompatibility antigen HA-2-specific T-cell receptor complexes expressing a conserved alpha joining region. Gene Therapy, Blood, 2003, vol. 102, No. 10, 3530-3540.

Liang et al. A Single TCRalpha-Chain with Dominant Peptide Recognition in the Allorestricted HER2/neu-Specific T Cell Repertoire. The Journal of Immunology, Dec. 30, 2009, 184:1617-1629.

McAulay et al. Epitope Specificity and Clonality of EBV-Specific CLTs Used to Treat Posttransplant Lymphoproliferative Disease. The Journal of Immunology, 2009, 182: 3892-3901.

Stadinski et al., A Role for Differential Variable Gene Pairing in Creating T Cell Receptors Specific for Unique Major Histocompatibility Ligands. Cell Press; Immunity 35, 694-704, Nov. 23, 2011.

Tanaka-Harada et al., Biased usage of BV gene families of T-Cell receptors of WT1 (Wilms' tumor gene)-specific CD8 T cells in patients with myeloid malignancies. Cancer Science Feb. 2010; 101: 594-600.

Yang et al., Development of optimal bicistronic lentiviral vectors facilitates high-level TCR gene expression and robust tumor cell recognition. Gene Therapy 2008, 15, 1411-1423.

Yokosuka et al., Predominant Role of T Cell Receptor (TCR)alpha Chain in Forming Preimmune TCR Repertoire Revealed by Clonal TCR Reconstitution System. J. Exp. Med. 2002. vol. 195, No. 8: 991-1001.

Purbhoo et al., The Human CD8 Coreceptor Effects Cytotoxic T Cell Activation and Antigen Sensitivity Primarily by Mediating Complete Phosphorylation of the T Cell Receptor Chain. J. Biol. Chem. 2001, 276: 32786-32792.

Nakatsugawa et al. TCR Hemichain Gene Transfer Generates High Avidity Antitumor T Cells. Immune Therapy Program, Princess Margaret Cancer Centre, Toronto, ON (May 2014).

Ochi et al., Molecular Separation of Antigen Reactivity and Allogeneic Reactivity in Human T Cells. Immune Therapy Program, Princess Margaret Cancer Centre, Toronto, ON (May 2014).

* cited by examiner

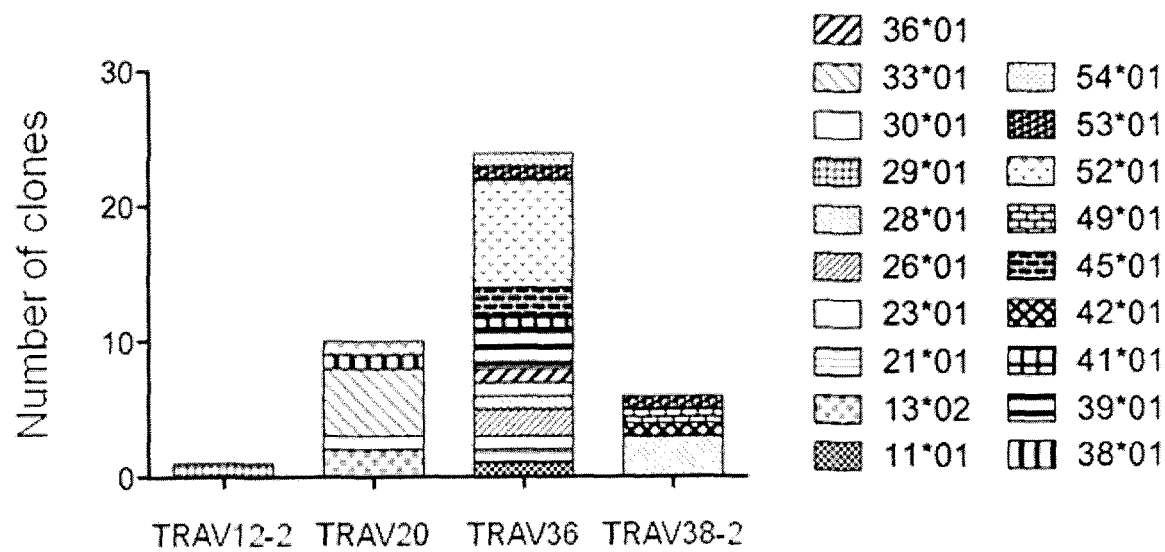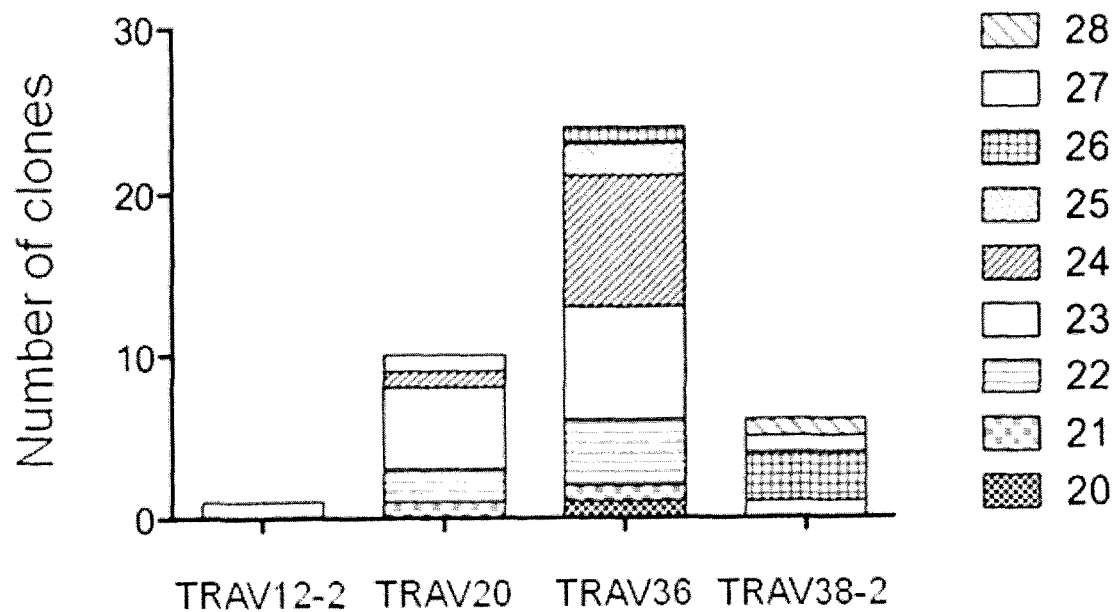
Fig.10

Fig. 12

SEQ ID NO:1

TCRα chain, Clone SIG35α nucleotide sequence

ATGATGCGGCCCATCGTGCTGGTGCTGCTGTTCGCTGCTAGCCTGGCCCAGAAAGAGGTGGAACAGAATCAGGGCCCCTCTGAGCGTGCCCG
AGGGGGCCATTGCCAGCCTGAACTGCACCTACAGCGACCGGGGCTCCCAGAGCTTCTTCTGGTACAGACAGTACAGCGGCAAGAGCCCGAGCT
GATCATGTTCATCTACAGCAACGGCGACAAAGAGGACGGCCGGTTCACCGCCCAGCTGAACAAGGCCAGTCAGTACGTGTCCCTGCTGATCCGG
　　　　　　　　CDR1
GACAGCCAGCCCAACATCCAGAACCCCGACCCGCCACCTACCTGTGCCGTGTCCATCGGCTTCGTCCATCGGCTTCGGCAACGTGCTGCACTGCGGCAGCGGCACCCAGGTCATCG
　　　CDR2
TGCTGCCCAACATCCAGAACCCCGACCCGCCGCCGTGTACCAGTGCGGGACAAGAGCAGCGACAAGAGCGTGTGCCTGTTCACCGACTTTGA
CAGCCAGACCAACGTGTCCCAGAAGGACAAGAGCGACGTGTACATCACCGACAAGACCGTGCTGGACATGCGGAGCATGGACTTCAAGAGCAAC
AGCGCCGTGGCCGTGAGCAACAAGAGCGACTTCGCCTGCGCCAACGCCTTCAACAACAGCATCATCCCCGAGGACACATTCTTCCCAAGCCCCG
AGAGCAGCGACGTGAAGCTGGTGGAAAAGAGCTTCGAGACCGACACCAACCTGAATCCAGAACTGAACCTGATCGGCTTCAGAATCCT
GCTGCTGAAGGTGGCCGGCTTCAACCTGCTGATGACCCTGCGGCTGTGGTCCTCGTGA
　　　　　　　　　　　　　　　CDR3

SEQ ID NO:2

TCRα chain, Clone SIG35α amino acid sequence

MMRPIVLVLLFATSALAQKEVEQNSGPLSVPEGAIASLNCTYSDRGSQSFFWYRQYSGKSPELIMFIYSNGDKEDGRFTAQLNKASQYVSLLIR
DSQPSDSATYLCAVSIGFGNVLHCGSGTQVIVLPNIQNPDPAVYQLRDSKSSDKSVCLFTDFDSQTNVSQSKDSDVYITDKTVLDMRSMDFKSN
　　　　　　　　　　　　　　CDR1　　　　　　　　　　　　　　　　　　　　　　　　　　　　CDR2
SAVAMSNKSDFACANAFNNSIIPEDTFFPSPESSCDVKLVEKSFETDTNLNFQNLSVIGFRILLKVAGFNLLMTLRLWSS
　　　　CDR3

Fig. 13

SEQ ID NO:3

TCRβ chain, Clone 794 nucleotide sequence

ATGGGCCCCCAGTCCTCCTTGGCTATGTGGTCCTTTGCCTTCTAGGAGCAGGCCCCCTGGAAGCCCAAGTGACCCAGAACCCAAGATACCTCATC
ACAGTGACTGGAAAGAAGTTAACAGTGACTTGTTCTCAGAATATGAACCATGAGTATATGTCCTGGTATCGACAAGACCCAGGGCTGGGCTTA
AGGCAGATCTACTATTCAATGAATGTTGAGGTGACTGATAAGGGAGATGTTCCTGAAGGGTACAAAGTCTCTCGAAAAGAGAAGAGGAATTTC
CCCCTGATCCTGGAGTCGCGCCAGCCCCAACCAGACCCTCTCTGTACTTCTGTGCCAGGAGTCGCTGAGCTGTGTTTGAGCCATCAGAAGCAGAGATCTCCACACCC
GGGACCAGGTTAACCGTTGTAGAGGACCTGAAACAAGGTGTTCCCTGACCACGTGGAGCTGGAAGCCCTCAAGGAGCAGCGCTGAGCAGCAGATACTGCCTGAGGAGTGCACAGTGGGGT
AAAAGGCCACACTGGTGTGCCTGGCACTGGCCAAGGAGGACCCCCTCAAGGAGCAGCCCCCTCAAGGAGCAGCCCTGAGCCGCCACCTTCTGG
CAGCAGGACCGGCGCAACCACTTCGCTGTCAAGTCCAGTTCGAAGTCCAGTTCAAGAGAATGACGAGTGAGCAGGATGGACCAGGATAGGGCCAAACCCGTCACCC
AGATCGTCAGCGCGGGAGCGCTGGGTAGAGCAGACTGTGGCTTTACCTGGTGTCCTACCAGCAGGGTCCTGCTGCCACCATCCTCTATGA
GATCCTGCTAGGGAAGGCCACCCTGTATGCTGTGCTGGTCAGCGCCCTTGTCTGTGTTGATGGCCATGGTCAAGAGAAAAGGATTTCTGA

SEQ ID NO:4

TCRβ chain, Clone 794 amino acid sequence

MGPQLLGYVVLCLLGAGPLEAQVTQNPRYLITVTGKKLTVTCSQNMNHEYMSWYRQDPGLGLRQIYYSMNVEVTDKGDVPEGYKVSRKEKRNF
PLILESPSPNQTSLYFCASSLLGDYGYTFGSGTRLTVVEDLNKVFPPEVAVFEPSEAEISHTQKATLVCLATGFFPDHVELSWWVNGKEVHSG
VSTDPQPLKEQPALNDSRYCLSSRLRVSATFWQNPRNHFRCQVQFYGLSENDEWTQDRAKPVTQIVSAEAMGRADCGFTSVSYQQGVLSATILY
EIILGKATIYAVLIVSALVLMAMVKRKDF

Fig. 14

SEQ ID NO:5
TCRβ chain, Clone 830 nucleotide sequence

ATGGGCCCCCAGCTCCTTGGCTATGTGGTCCTTTGCCTTCTAGGAGCAGGCCCCCTGGAAGCCCAAGTGACCCAGAACCCAAGATACCTCATCA
CAGTGACTGGAAAGAAGTTAACAGTGACTTGTCTCAGAATGAACCATGAGTATATGTCCTGGTATCGACAAGACCCAGGGCTGGGCTTAAG
                                                CDR1
GCAGATCTACTATTCAATGAATGTTGAGGTGACTGATAAGGGAGATGTTCCTGAAGGGTACAAAGTCTCTCGAAAAGAGAAGAGGAATTTCCCC
                               CDR2
CTGATCCTGGAGTCGCCCAGCCCCAACCAGACCTCTCTGTACTTCTGTGCCAGCAGTTTAGGGGGTGCCTACGAGCAGTACTTCGGGCCGGGCA
                                                   CDR3
CCAGGCTCACGGTCGTGTGCCTGGCCACAGAGGACCTGAAAAACGTGTTCCCACCCGAGGTCGCTGCTGTGTTTGAGCCATCAGAAGCAGAGATCTCCACACCCAAAA
GGCCACACTGGTCGTGTGCCTGGCACAGGCTTCTACCCGGACCAGGCTGAATGGGAAGGAGGTGCACAGTGGGGTCAGC
ACAGACCCGCAGCCGCCAACCACTTCCGCTGTCAAGTCCAGATACTGCCTGAGCAGCCGCTGAGGGTTCTGGCCAAACCTGTCACCCAGA
ACCCCGCAACCATTCCGCTGTCAAGTCCAGATACTGCCTGAGCAGCCGCTGAGGGTTCTGGCCAAACCTGTCACCCAGAT
CGTCAGCGCCGAGGCCGCACCTTGTATGCCGTGCTGGTCAGTGCCCTGGTCCTGCTGGTCAAGAAAAGGATTCCAGAGGCTAG
TTGCTAGGAAGGCACCTTGTATGCCGTGCTGGTCAGTGCCCTGGTCCTGCTGATGGCAATGGTCAAGAGAAAAGGATTCCAGAGGCTAG

SEQ ID NO:6
TCRβ chain, Clone 830 amino acid sequence

MGPQLLGYVVLCLLGAGPLEAQVTQNPRYLITVTGKKLTVTCSQNMNHEYMSWYRQDPGLGLRQIYYSMNVEVTDKGDVPEGYKVSRKEKRNFP
                                                CDR1                      CDR2
LILESPSPNQTSLYFCASSLGGAYEQYFGPGTRLTVTEDLKNVFPPEVAVFEPSEAEISHTQKATLVCLATGFYPDHVELSWWVNGKEVHSGVS
TDPQPLKEQPALNDSRYCLSSRLRVSATFWQNPRNHFRCQVQFYGLSENDEWTQDRAKPVTQIVSAEAWGRADCGFTSESYQQGVLSATILYEI
        CDR3
LLGKATLYAVLVSALVLMAMVKRKDSRG

Fig. 15

SEQ ID NO:7

TCRα chain, Clone T53 nucleotide sequence

ATGATGAAGTGTCCACAGGCTTTACTAGCTATCTTTTGGCTTCTACTGAGCTGGGTGAGCAGTGAAGACAAGGTGGTACAAAGCCCTCTATCT
CTGGTTGTCCACGAGGGAGAGACACTGTAACTCTCAATTGCAGTTATGAAGTGACTAACTTTCGAAGCCTACTATGGTACAAGCAGGAAAGAAA
GCTCCCACATTTCTATTTATGCTAACTTCAAGTGGAATTGAAAAGAAGTCAGGAAGAGACTAAGTAGCATATTAGATAAGAAAGAACTTTTCAGC

CDR1

ATCCTGAACATCACAGCCACCCAGACCGGAGACTCGGCCGTCTACCTCTGTGCTGTGATAACTGGTGGTACTAGCTATGGAAAGCTGACATTT

CDR2                                                              CDR3

GGAGAAGGGACCATCTTGACTGTCCATCCAAATATCCAGAACCCCTGACCTGTCCGTGTACCAGCTGAGAGACTCTAAATCCAGTGACAAGTCT
GTCTGCCTATTCACCGATTTTGATTCTCAAACAAATGTGTCACAAAGTCTGATGTCTATATCACAGACAAACTGTGCTAGACATG
AGGTCTATGGACTTCAAGAGACAAGTCAACAGTGCTGTGGCCTGAGCAACAAATCTGACTTTGCATGTGCAAAACGCCTTCAACAACAGCATTATTCCA
GAAGACACCTTCTTCCCCAGCCAGAAAGTTCCTGTGATGTCAAGCTGGTCGAGAAAAGCTTTGAAACAGATACAGAAACCTAAACTTTCAAAAC
CTGTCAGTGATTGGGGTTCCGAATCCTCCTGAAATCCCAGCTGA

SEQ ID NO:8

TCRα chain, Clone T53 amino acid sequence

MMKCPQALLAIFWLLLSWVSSEDKVVQSPLSIVVHEGDTVTLNCSYEVTNFRSLIWYKQEKKAPTFLFMLTSSGIEKKSGRLSSILDKKELFS

CDR1                                                                     CDR2

ILNITATQTGISAVYLCAVITGGTSYGKLTFGQGTILTVHPNIQMPDPAVYQLRDSKSSDKSVCLFTDFDSQTNVSQSKDSDVYITDKTVLD

CDR3

RSMDFKSNSAVAWSNKSDFACANAFNNSIIPEDTFFPSPESSCDVKLVEKSFETDTNLNFQNLSVIGFRILLLKVAGFNLLMTLRLMSS

Fig. 16

SEQ ID NO:9

TCRα chain, Clone A262 nucleotide sequence

ATGATGAAGTGTCCACAGGCTTTACTAGCTATCTTTTGGCTTCTACTGAGCTGGGTGAGCAGTGAAGACAAGGTGGTACAAAGCCCTCTATCT
CTGGTTGTCCACGAGGGAGACACACTGTAACTCTCAATTGCAGTTATGAAGTGACTAACTTTCGAAGCTACTATGGTACAAGCAGGAAAAGAAA
GCTCCCACATTTCTATTTATGCTAACTTCAAGTGGAATTGAAAAGAAGTCAGGAAGACTAAGTAGCATATTAGATAAGAAAGAACTTTTCAGC
                              CDR1
                                         CDR2
ATCCTGAACATCACAGCCACCCAGACCGGAGACTCAGCTCAGCCACTTATCTCTGTGCTGTGCAGAATGCTGGTGGTACTAGCTATGGAAAGCTGACA
                                                                             CDR3
TTTGGACAAGGGACCATCTTGACTGTCCATCCAAATATCCAGAACCCTGACTGTCCAGCTGAGAGACTCTAAATCCAGTGACAAG
TCTCTGTGCCTATTCACCGATTTTGATTCTCAAAACAAATGTGTCACAAAGTAAGGATTCTGATGTGTATATCACAGACAAAACTGTGCTAGAC
ATGAGGTCTGATGGAGTTCAAGAGCAACAGTGCTGTGGCCTGGAGCAAAATCTGACTTTGCATGTCAAACGCCTTCAACAACAGCAGTATT
CCAGAAGACACCTTCTTCCCCAGCCAGAAGTTCCTGTGATGTCAAGCTGGTCGTGAAAAAGCTTTGAAACAGATACGAACCTAAACTTTCAA
AACCTGTCAGTGATGATTGGGTTCCGAATCCTCCTCCTGAAAGTGGCCGGGGTTTAATCTGCTCATGACGCTGCTGTGGTCCAGCTGA

SEQ ID NO:10

TCRα chain, Clone A262 amino acid sequence

MMKCPQALLAIFWLLLSMVSSEDKVVQSPLSLVVHEGDTVTLNCSYEVTNFRSLLWYKQEKKAPTFLFMLTSSGIEKKSGRLSSILDKKELFS
                                                                    CDR1                CDR2
ILNITATQTGDSATYLCAVQNAGGTSYGKLTFGQGTILTVHPNIQNPDAVYQLRDSKSSDKSVCLFTDFDSQTNVSQSKDSDVYITDKTVLD
                       CDR3
MRSMDFKSNSAVAWSNKSDFACANAFNNSIIPEDTFFPSPESSCDVKLIVEKSFETDTNLNFQNLSVIGFRILLLKVAGFNLLMTLRLMSS

Fig. 17

SEQ ID NO:11
TCRα chain, Clone T243 nucleotide sequence

ATGATGAAGTGTCCACAGGCTTTACTAGCTATCTTTTGGCTTCTACTGAGCTGGGTGAGCAGTGAAGACAAGGTGGTACAAAGCCCTCTATCT
CTGGTTGTCCACGAGGGAGACACTGTAACTCCTCAATTGCAGTTATGAAGTGACTAACTTTGACTACTTTCGAAGCCTACTATGGTACAAGCAGGAAAGAAA
                                                                      <u>CDR1</u>
GCTCCCACATTTCTATTTATGCTAACTTCAAGTGGAATTGAAAAGAAGTCAGGAAGACTAAGTAGCATATTAGATAAGAAAGAACTTTTCAGC
                                <u>CDR2</u>
ATCCTGAACATCACACGCCACCCAGAGACTCGGCCGTCTACCT<u>CTGTGCTGTGCTTACCCAAACTGGGGCAAACAACCTCTCTTTGGG</u>
                                              <u>CDR3</u>
ACTGGAACGAGAGACTCACCGTTATTCCCTATATCCAGAACCCTGACCCTGAGAGACTCTAAATCCAGTGAGACAAGTCTGTC
TGCCTATTCACCGATTTTGATTCTCAAACAAATGTGTCAAAACAAATCTGTATATCACAGACACAAAACTGTGCTAGACATGAGG
TCTATGGACTTCAAGAGCAACAGTGCTGTGGCCCTGAGCAACAAATCTGACTTTGCAAACGCCTTCAACAACAGCCTAAACTTATTCCAGAA
GACACCTTCTTCCCCAGCCAGAATCCCCCTCCCCTGAAAGTTCCTGTGATGTCAAGCTGGTCGAGAAAGTTTGAAACAGATGACGAACCTAAACCTGA
TCAGTGATTGGGGTTCCGAATCTGCTACTCATGACGCTGCGGCCTGTGGTCCAGCTGA

SEQ ID NO:12
TCRα chain, Clone T243 amino acid sequence

MMKCPQALLAIFWLLLSWVSSEDKVVQSPLSLVVHEGDTVTLNCSYEV<u>TNFRSLIWYKQEKKAPTF</u>LFMLTSSGIEKKSGRLSSILDKKELFS
                                                    <u>CDR1</u>
ILNITATQTGDSAVYLCAVLTQTGANNLFFGTGTRLTVIPYIQNPDEAVYQLRDSKSSDKSVCLFTDFDSQTNVSQSKDSDVYITDKTVLDMR
                                <u>CDR2</u>
SMDFKSNSAVAWSNKSDFACANAFNNSIIPEDTFFPSPESSCDVKLIVEKSFETDTNLNFQNLSVIGFRILLLKVAGFNLLMTLRLWSS
               <u>CDR3</u>

Fig. 18

SEQ ID NO:13

TCRα chain, Clone T262 nucleotide sequence

ATGGAGAAAATGTTGGAGTGTGCATTCATAGTTCTTGTGGCTTTCATTGTGCTTCAGCTTGGCTGGTTGAGTGGAGAAGACCAGGTTGAGTGGAGAGTCCGAGGCC
CTGAGACTCCAGGAGGGAGAGAGTCAGTAGCAGTCTCAACTGCCAGTTACACAGTCCAGTGGGTTCTGCAACTGGAGGCTGTGCTTCTGGTATAGGCAAGATCCTGGG
                                                                                        CDR1
AAAGGCCCTGAATTCCTCTTCACCCTGTATTCAGCTGGGAAGAGAAAAGGCTAAAAGCCACACATTAACAGACAAAGAAGGAAAGCTTT
              CDR2
CTGCACATCACAGCCCCTAAACCTGAAGACTCAGCCACTTATCTCTGTGCTGTGCAGGCCCTTAAGGAATAATGCTGGCAACAACCGTAAGCTG
                                                                CDR3
ATTTGGGGATTGGGAACAAGCCTGGCAGTAAATCCGAATATCCAGAGAACCCTGACCTTGCCGTGTGAGAGACTCTAAATCCAGTGAC
AAGTCTGTCTGCCTATTCCACCGATTTTGATTCTCAAAACAAATGTGTCACAAAGTAAGGATTCTGATGTGTATATCACAGACAAAACTGTGCTA
GACATGAGGTCTATGGACTTCAAGAGCAACAGTGCTGTGGCCTGTGGAGCAAATCTGACTTTGCATGTGCAAACGCCTTCAACAACAGCATT
ATTCCAGAAGACACCTTCTTCCCCAGCCAGAAAGTTCCTGTGATGTCAAGTCTGGTCGAGAAAAAGCTTTGAAACAACAGCTAAACTTT
CAAAACCTGTCAGTGATTGGGTTCCGAATTCCTCCTGAAATCCCTGAATCCCTGAAAGTGGCCGGGGTTTAATCTGCTCATGACGCTGCTGGTCCAGCTGA

SEQ ID NO:14

TCRα chain, Clone T262 amino acid sequence

MEKMLECAFIVLMLQLGWLSGEDQVTQSPEALRLQEGESSSLNCSYTVSGLRGLFWYRQDPGKGPEFLFTLYSAGEEKEKERLKATLTKKESF
                                                CDR1
LHITAPKPEDSATYLCAVQALRNNAGNNRKLIWGLGTSLAVNPNIQMPDPAVYQLRDSKSSDKSVCLFTDFDSQTNVSQSKDSDVYITDKTVL
                                CDR2
DMRSMDFKSNSAVAMSNKSDFACANAFNNSIIPEDTFFPSPESSCDVKLVEKSFETDTNLNFQNLSVIGFRILLLKVAGFNLLMTLRLMSS
              CDR3

Fig. 19

SEQ ID NO:15

TCRβ chain, Clone TAK1 nucleotide sequence

ATGATGCGGCCCATCGTGTGCTGGTGCTGCTGTTTGCCACATCTGCCCTGGCCGGGGTGACCCAGACCCCTAGATACCTGATCAAGACCAGAGGC
CAGCAGGTCACACTGAGCTGCAGCCCTATCAGCGGCCACAGAAGCGTGTCCTGGTATCAGCAGACAGACCCAGGCCAGGGCCTGCAGTTCCTGTTC
GAGTACTTCAGCGAGACACAGCGGAAACAAGGCAACTTCCCCGGCAGATTCAGCGGCAGACAGTTCAGCAACAGCCGGCAGCGAGATGAACGTG
    CDR1
                                                                        CDR2
TCCACCCTGGAACTGGGCGACAGCGCCCTGTACCTGTGTGCCTCTTCTCTGGGCCGTGTTCGGCCGAGATCAGCCACCCAG
                                  CDR3
ACCAGACTGACCGTGCTGGAAGATCTGAAGAACGTGTTCCCCCAGAGGTGGCCGTGTTCGAGCCTTCTGAGGCCAAAGAGGTGCACAGCGGCGTC
AAAGCCACCCTCGTGTGTCTGGCCACCGGCTTCTACCCCGACCACGTGGAACTGTCTTGGTGGGTCAACGGGACTGAGCAGCAGCCTTCTGGACTGTCCGCCACCTTCTGG
AGCAACGGAAGCGGACTGAGCAGCAGCCCGCCCTGAAACGTGCAGCCTGCAGGTGCAGGTTCTAGATGCCAGAACCACTTCAGATGCCAGGTGCAGTTGCAGATGCCTTACCGGAGAGCCTGTGACC
CAGAACCCCCGGAAGACACCACTTCAGATGCCAGGTGCAGGTTCTACGGCCTTTACCAGCAGAGCAGCACTCAGCAGCAGGGCGTCTGAGCGCCCATCCTGTAC
CAGATCGTGTCTGCCGAGGCTTGGGGCAGGCCACCCTGTATGCCATGGTCCTGGTGCTCAGCCCCTGGTCAGCCCCTGATGGTGCTGAAGGGCTATGGTCAAGCGGAAGGACAGCCGGCGCTGA
GAGATCCTGCTGGGCAAGGCCACAGGCCACCCTGTATGCCATGGTCCTGGTGCTCAGCCCCTGGTCAGCCCCTGATGGT

SEQ ID NO:16

TCRβ chain, Clone TAK1 amino acid sequence

MMRPIVLVLLFATSALAGVTQTPRYLIKTRGQQVTLSCSPISGHRSVSWYQQTPGQGLQFLFEYFSETQRNKGNFPGRFSGRQFSNSRSEMNV
                                         CDR1                                       CDR2
STLELGDSALYLCASSLGWRETYNEQFFGPGTRLTVLEDLKNVFPPEVAVFEPSEAEISHTQKATLVCLATGFYPDHVELSWWVNGKEVHSGV
           CDR3
STDPQPLKEQPALNDSRYCLSSRLRVSATFWQNPRNHFRCQVQFYGLSENDEWTQDRAKPVTQIVSAEAWGRADCGFTSESYQQGVLSATILY
EILLGKATLYAVLVSALVLMAMVKRKDSRG

| TCRα or TCRβ without stop codon | Furin recognition sequence | SGSG linker | F2A | ΔNGFR |

Antitumor TCR αβ Chains vs. α or β
Hemi-Chain Gene Therapy

|  | αβ chains | α or β hemi-chain |
|---|---|---|
| No. of genes transduced | Two | One |
| TCR clonality | Monoclonal | Highly polyclonal |
| TCR affinity | Fixed (high) | Highly broad (Ultra high ~ low) |
| GVHD risk | 1 | ≪1/2 |

SEQ ID NO:93
TCRβ chain, Clone 8H nucleotide sequence

ATGGGCCCCCAGCTCCTTGGCTATGTGGTCCTTTGCCTTCTAGGAGCAGGCCCCCTGGAAGCCCAAGTGACCCAAAACCCAGAGATACCTCATC
ACAGTGACTGGAAAGAAGTTAACAGTTGACTTGTTCTCAGAATATGAAGTCCTGGTATCGACAAGACCCAGGGCTGGGCTTA
AGGCAGATCTACTATTCAATGAATGTTGAGGTGACTGATAAGGGAGATGTTCCTGAAGGGTACAAAGTCTCTCGAAAAGAGAAGAGGAATTTC
<u>CDR1</u>
CCCCTGATCCTGGAGTCGCCCCAGCCCCAACCAGACCCTCTCTGTACTTCTGTGCCAGCAGTCCCTGGGGCCATGAGCAGTACTTCGGGCCG
<u>CDR2</u>
GGCACCAGGCTCACGGTTCACGGTCACAGGCCAAAAACCTGAAAAACGTGTTCCCACCCGACCTGCCTGTCTGTGTTTGAGCCATCAGAAGCAGAGATCTCCACACC
CAAAAGGCCACACTGGTGTGCCTGGCCACAGGCTTCTACCCCGACCACGTGGAGCTGAGTGCTGGGAAGGAGGTGCACAGTGGG
GTCAGCACAGACCCCCGCAGCCCCTCACTTCCGCTGTGTCAAGTCCAGATCTGCTTCAAGTCGGCTGCTTCACCTCGACAGACGTC
TGGCAGATCGTCAGCGCGTCAGGGCCTGGGGTCTTACGGGGCTTCACCTGCGAGTCGTGCCTGATGGCCATGGTCAAGAGAAAGGATTCCAGAGGC
ACCCAGATCTTGCTAGGGAAGGCCACCTTGCTATGCCGTGCTCGTGTATGCCCTGCGGTCAGTGCCTGATGGCCATGGTCAAGAGAAAGGATTCCAGAGGC
TATGAGATCTTGCTAGGGAAGGCCACCTTGCTATGCCGTGCTCGTGTATGCCCTGCGGTCAGTGCCTGATGGCCATGGTCAAGAGAAAGGATTCCAGAGGC
<u>CDR3 (novel)</u>
TAG SEQ ID NO:94
TCRβ chain, Clone 8H amino acid sequence MGPQLLGYVVLCLLGAGPLEAQVTQNPRYLITVTGKKLTVTCSQMMNHEYMSWYRQDPGLGLRQIYYSMNVEVTDKGDVPEGYKVSRKEKRNF
<u>CDR1</u>
PLILESPSPNQTSLYFCASSPLGAMEQYFGPGTRLTVTEDLKNVPPEVAVFEPSEAEISHTQKATLVCLATGFYPDHVELSWWVNGKEVHSG
<u>CDR2</u>
VSTDPQPLKEQPALNDSRYCLSSRLRVSATFWQNPRNHFRCQVQFYGLSENDEWTQDRAKPVTQIVSAEAWGRADCGFTSESYQQGVLSATIL
<u>CDR3 (novel)</u>
YEILLGKATIYAVLVSALVLMAMVKRKDSRGZ

Fig. 29

SEQ ID NO:95
TCRβ chain, Clone 7Q nucleotide sequence

ATGGGCCCCAGTCCTCCTTGGCTATGTGGTCCTTTGCCTTCTAGGAGCAGGCCCCCTGGAAGCCCAAGTGACCCAGAACCCAAGATACCTCATC
ACAGTGACTGGAAAGAAGTTAACAGTGACTTGTTCTCAGAATATGAACCATGAGTATATGTCCTGGTATCGACAAGACCCAGGGCTGGGCTTA
AGGCAGATCTACTATTCAATGAATGTTGAGGTGACTGATAAGGGAGATGTTCCTGAAGGGTACAAAGTCTCTCGAAAAGAAGAGGAATTTC
<u>CDR1</u>
<u>CDR2</u>
CCCCTGATCCTGGAGTCGCCCAGCCCAGAGACCCTCTCTGTACTTCTCTGTGCCAGCAGTCCCTACATGAATGAACTGAAGCTTTCTTTGGA
<u>CDR3 (novel)</u>
CAAGGCACAGACTCACACAGTTGTAGAGGAACCTGAACAAGGTGTTCCCCTGAGCCATCAGAAGCAGAGATCTCCCAC
ACCCAAAAGGCCACACTGGTCTGTGTGCAGCCGCCCCTCAAGGAGCAGCCCTGTCAAGTCCAGTTCTACGGCTTTACCTCGGTTGAAGGGTCTCGCCAGT
GGGGTCAGCACGGACCCCGAGAACCCCGTCAGCGCCGAGATCTCACGGCTTTACCTCGGTGAGGGTCTCGGCCACC
TTCTGGCAGAACCCCGTCAGCGCCGAGAACCTCAGTCCGTGTCAAGTTCCGTGTCAAGTCGACGAGTGGACCAAGGTCCTGTCTGCCAAACCC
GTCACCCAGATCGTCAGCGCCGAGGCTGGGGGTAGAGCAGGACTGTGGCTTTACCTCGGTGTCCTAGCAGCCAGGGGTCCTGTCTGCCACATC
CTCTATGAGATCCTGCTAGGGAAGGCCACCCTGTATGCTGTGCTGGTCAGCGCCCTTGTGTTGATGGCCATGGTCAAGAGAAAGGATTTCTGA SEQ ID NO:96
TCRβ chain, Clone 7Q amino acid sequence MGPQLLGYVVLCLLGAGPLEAQVTQNPRYLITVTGKKLTVTCSQNMNHEYMSWYRQDPGLGLRQIYY<u>SMNVEVTDKGDVPEGYKVSRK</u>
<u>CDR1</u>
<u>CDR2</u>
EKRNFPLIIESPSPNQTSLYFCA<u>SSPYMNELKLSLD</u>SRYCLSSRLRVSATFWQNPRNHFRCQVQFYGLSENDEMTQDRAKPVTQIVSAEAWGRADCGF
<u>CDR3 (novel)</u>
WVNGKEVHSGVSTDPQPLKEQPALNDSRYCLSSRLRVSATFWQNPRNHFRCQVQFYGLSENDEMTQDRAKPVTQIVSAEAWGRADCGF
TSVSYQQGVLSATILYEILLGKATLYAVLVSALVLMAMVKRKDF

Fig. 30

SEQ ID NO:97
TCRβ chain, Clone 9J nucleotide sequence

ATGGGCTCCAGGCTGCTCTGTTGGGTGCTGCTGTGTCTCCTGGGAGCAGGCCAGTAAAGGCTGGAGTCACTCAAACTCCAAGATATCTGATC
AAAACGAGAGGACAGCAAGTGACACTGAGCTGCTCCCCTATCTCTGGGCATAGGAGTGTATCCTGGTACCAACAGACCCCAGGACAGGGCCTT
CAGTTCCTCCTCTTTGAATACTTCAGTGAGACACAGAGAAACAAAGGAAAACTTCCCTGGTCGATTCTCAGGGCGCCAGTTCTCTAACTCTCGCTCT
        CDR1
GAGATGAATGTGAGCACCTTGGAGCTGGGGGACTCGGCCCCTTTATCTTTGCCACAGCAGGGATGGCTACACCTTCGGTTCGGGG
            CDR2                                            CDR3 (novel)
ACCAGGTTAACCGTTGTAGAGGACCTGAAACAAGGTGTTCCCACCCGAGGTCGCTGTGTTTGAGCCATCAGAAGCAGAGAATCTCCCACACCAA
AAGGCCACACTGGTGTGCCTGGCCACAGCGTTCTTCCCTGACCACGTGGAGCTGAGTTGGTGGTGAGCTGAATGGGAGTGGGGTGCACAGTGGGGTC
AGCACGGACCCGCAGCCCTCAAGGAGCAGCCCGCCTCAATGACTCCAGATACTTCCTGAGCAGCCGCCTGAGGGTCTCGGCCACCTTCTGG
CAGAACCCCCGCAACCACTTCCGCTGTCAAGTACAGTTCTACGGGCTCTCGGAGAATGACGAGTGGACCCAGGATAGGGCCAAACCCGTCACC
CAGATCGTCAGCGCCGAGGCGCCGGCGCCACCCTGTCGCTGCTGCCTGTGCTGATGCGCCCCTTGTGTTGATGGCCATGGTCAAGAGAAAGGATTTCTGA SEQ ID NO:98
TCRβ chain, Clone 9J amino acid sequence MGSRLLCWVLLCLLGAGPVKAGVTQTPRYLIKTRGQQVTLSCSPISGHRSVSWYQQTPGQGLQFLFEYFSETQRNKGNFPGRFSGRQFSNSRS
                                                        CDR1                      CDR2
EMNVSTLELGDSALYLCASSWTGDGYTFGSGTRLTVVEDLNKVFPPEVAVFEPSEAEISHTQKATLVCLATGFFPDHVELSWWVNGKEVHSGV
                    CDR3 (novel)
STDPQPLKEQPALNDSRYCLSSRLRVSATFWQNPRNHFRCQVQFYGLSENDEWTQDRAKPVTQIVSAEAMGRADCGFTSVSYQQGVLSATILY
EILLGKATLYAVLVSALVLMAMVKRKDFZ

SEQUENCE LISTING

```
<160> NUMBER OF SEQ ID NOS: 124

<210> SEQ ID NO 1
<211> LENGTH: 810
<212> TYPE: DNA
<213> ORGANISM: Artificial Sequence
<220> FEATURE:
<223> OTHER INFORMATION: Synthetic Construct

<400> SEQUENCE: 1
atgatgcggc ccatcgtgct ggtgctgctg ttcgccacaa gcgccctggc ccagaaagag    60
gtggaacaga acagcggccc tctgagcgtg cccgagggcg ccattgccag cctgaactgc   120
acctacagcg accggggctc ccagagcttc ttctggtaca gacagtacag cggcaagagc   180
cccgagctga tcatgttcat ctacagcaac ggcgacaaag aggacggccg gttcaccgcc   240
cagctgaaca aggccagcca gtacgtgtcc ctgctgatcc gggacagcca gcccagcgac   300
agcgccacct acctgtgtgc cgtgtccatc ggcttcggca acgtgctgca ctgcggcagc   360
ggcacccagg tcatcgtgct gcccaacatc cagaacccg acccccgccgt gtaccagctg   420 cgggacagca agagcagcga caagagcgtg tgcctgttca ccgactttga cagccagacc   480
aacgtgtccc agagcaagga cagcgacgtg tacatcaccg ataagacagt gctggacatg   540
cggagcatgg acttcaagag caacagcgcc gtggcctggt ccaacaagag cgacttcgcc   600
tgcgccaacg ccttcaacaa cagcatcatc cccgaggaca cattcttccc aagccccgag   660
agcagctgcg acgtgaagct ggtggaaaag agcttcgaga cagacaccaa cctgaacttc   720
cagaacctga gcgtgatcgg cttcagaatc ctgctgctga aggtggccgg cttcaacctg   780
ctgatgaccc tgcggctgtg gtcctcgtga                                    810

<210> SEQ ID NO 2
<211> LENGTH: 269
<212> TYPE: PRT
```

<213> ORGANISM: Artificial Sequence
<220> FEATURE:
<223> OTHER INFORMATION: Synthetic Construct

<400> SEQUENCE: 2

```
Met Met Arg Pro Ile Val Leu Val Leu Leu Phe Ala Thr Ser Ala Leu
1               5                   10                  15

Ala Gln Lys Glu Val Glu Gln Asn Ser Gly Pro Leu Ser Val Pro Glu
            20                  25                  30

Gly Ala Ile Ala Ser Leu Asn Cys Thr Tyr Ser Asp Arg Gly Ser Gln
        35                  40                  45

Ser Phe Phe Trp Tyr Arg Gln Tyr Ser Gly Lys Ser Pro Glu Leu Ile
    50                  55                  60

Met Phe Ile Tyr Ser Asn Gly Asp Lys Glu Asp Gly Arg Phe Thr Ala
65                  70                  75                  80

Gln Leu Asn Lys Ala Ser Gln Tyr Val Ser Leu Leu Ile Arg Asp Ser
                85                  90                  95

Gln Pro Ser Asp Ser Ala Thr Tyr Leu Cys Ala Val Ser Ile Gly Phe
            100                 105                 110

Gly Asn Val Leu His Cys Gly Ser Gly Thr Gln Val Ile Val Leu Pro
        115                 120                 125

Asn Ile Gln Asn Pro Asp Pro Ala Val Tyr Gln Leu Arg Asp Ser Lys
    130                 135                 140

Ser Ser Asp Lys Ser Val Cys Leu Phe Thr Asp Phe Asp Ser Gln Thr
145                 150                 155                 160

Asn Val Ser Gln Ser Lys Asp Ser Asp Val Tyr Ile Thr Asp Lys Thr
                165                 170                 175

Val Leu Asp Met Arg Ser Met Asp Phe Lys Ser Asn Ser Ala Val Ala
            180                 185                 190

Trp Ser Asn Lys Ser Asp Phe Ala Cys Ala Asn Ala Phe Asn Asn Ser
        195                 200                 205

Ile Ile Pro Glu Asp Thr Phe Phe Pro Ser Pro Glu Ser Ser Cys Asp
    210                 215                 220

Val Lys Leu Val Glu Lys Ser Phe Glu Thr Asp Thr Asn Leu Asn Phe
225                 230                 235                 240

Gln Asn Leu Ser Val Ile Gly Phe Arg Ile Leu Leu Leu Lys Val Ala
                245                 250                 255

Gly Phe Asn Leu Leu Met Thr Leu Arg Leu Trp Ser Ser
            260                 265
```

<210> SEQ ID NO 3
<211> LENGTH: 927
<212> TYPE: DNA
<213> ORGANISM: Homo Sapien

<400> SEQUENCE: 3

| | | | | | |
|---|---|---|---|---|---|
| atgggcccccc | agctccttgg | ctatgtggtc | ctttgccttc | taggagcagg | ccccctggaa | 60 |
| gcccaagtga | cccagaaccc | aagataccttc | atcacagtga | ctggaaagaa | gttaacagtg | 120 |
| acttgttctc | agaatatgaa | ccatgagtat | atgtcctggt | atcgacaaga | cccagggctg | 180 |
| ggcttaaggc | agatctacta | ttcaatgaat | gttgaggtga | ctgataaggg | agatgttcct | 240 |
| gaagggtaca | agtctctcg | aaaagagaag | aggaatttcc | ccctgatcct | ggagtcgccc | 300 |
| agccccaacc | agacctctct | gtacttctgt | gccagcagtc | tactcgggga | ctatggctac | 360 |
| accttcggtt | cggggaccag | gttaaccgtt | gtagaggacc | tgaacaaggt | gttcccaccc | 420 |

-continued

```
gaggtcgctg tgtttgagcc atcagaagca gagatctccc acacccaaaa ggccacactg    480
gtgtgcctgg ccacaggctt cttccctgac cacgtggagc tgagctggtg ggtgaatggg    540
aaggaggtgc acagtggggt cagcacggac ccgcagcccc tcaaggagca gcccgccctc    600
aatgactcca gatactgcct gagcagccgc ctgagggtct cggccacctt ctggcagaac    660
ccccgcaacc acttccgctg tcaagtccag ttctacgggc tctcggagaa tgacgagtgg    720
acccaggata gggccaaacc cgtcacccag atcgtcagcg ccgaggcctg ggtagagca    780 gactgtggct ttacctcggt gtcctaccag caagggtcc tgtctgccac catcctctat    840
gagatcctgc tagggaaggc caccctgtat gctgtgctgg tcagcgccct tgtgttgatg    900
gccatggtca agagaaagga tttctga                                        927
```

<210> SEQ ID NO 4
<211> LENGTH: 308
<212> TYPE: PRT
<213> ORGANISM: Homo Sapien

<400> SEQUENCE: 4

```
Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
                20                  25                  30

Val Thr Gly Lys Lys Leu Thr Val Thr Cys Ser Gln Asn Met Asn His
            35                  40                  45

Glu Tyr Met Ser Trp Tyr Arg Gln Asp Pro Gly Leu Gly Leu Arg Gln
        50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Leu Leu Gly Asp Tyr Gly Tyr Thr Phe Gly Ser Gly Thr Arg Leu
        115                 120                 125

Thr Val Val Glu Asp Leu Asn Lys Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
        275                 280                 285
```

Leu Tyr Ala Val Leu Val Ser Ala Leu Val Leu Met Ala Met Val Lys
    290                 295                 300

Arg Lys Asp Phe
305

<210> SEQ ID NO 5
<211> LENGTH: 933
<212> TYPE: DNA
<213> ORGANISM: Homo Sapien

<400> SEQUENCE: 5

| | | | | | |
|---|---|---|---|---|---|
| atgggccccc | agctccttgg | ctatgtggtc | ctttgccttc | taggagcagg | ccccctggaa | 60 |
| gcccaagtga | cccagaaccc | aagatacctc | atcacagtga | ctggaaagaa | gttaacagtg | 120 |
| acttgttctc | agaatatgaa | ccatgagtat | atgtcctggt | atcgacaaga | cccagggctg | 180 |
| ggcttaaggc | agatctacta | ttcaatgaat | gttgaggtga | ctgataaggg | agatgttcct | 240 |
| gaagggtaca | agtctctcg | aaagagaag | aggaatttcc | ccctgatcct | ggagtcgccc | 300 |
| agccccaacc | agacctctct | gtacttctgt | gccagcagtt | taggggtgc | ctacgagcag | 360 |
| tacttcgggc | cgggcaccag | gctcacggtc | acagaggacc | tgaaaaacgt | gttcccaccc | 420 |
| gaggtcgctg | tgtttgagcc | atcagaagca | gagatctccc | acacccaaaa | ggccacactg | 480 |
| gtgtgcctgg | ccacaggctt | ctaccccgac | acgtggagc | tgagctggtg | ggtgaatggg | 540 |
| aaggaggtgc | acagtggggt | cagcacagac | ccgcagcccc | tcaaggagca | gcccgccctc | 600 |
| aatgactcca | gatactgcct | gagcagccgc | ctgagggtct | cggccacctt | ctggcagaac | 660 |
| ccccgcaacc | acttccgctg | tcaagtccag | ttctacgggc | tctcggagaa | tgacgagtgg | 720 |
| acccaggata | gggccaaacc | tgtcacccag | atcgtcagcg | ccgaggcctg | ggtagagca | 780 |
| gactgtggct | tcacctccga | gtcttaccag | caagggtcc | tgtctgccac | catcctctat | 840 |
| gagatcttgc | tagggaaggc | caccttgtat | gccgtgctgg | tcagtgccct | cgtgctgatg | 900 |
| gcaatggtca | agagaaagga | ttccagaggc | tag | | | 933 |

<210> SEQ ID NO 6
<211> LENGTH: 310
<212> TYPE: PRT
<213> ORGANISM: Homo Sapien

<400> SEQUENCE: 6

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Leu Gly Gly Ala Tyr Glu Gln Tyr Phe Gly Pro Gly Thr Arg Leu
        115                 120                 125

Thr Val Thr Glu Asp Leu Lys Asn Val Phe Pro Pro Glu Val Ala Val
            130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
                180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
                260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 7
<211> LENGTH: 828
<212> TYPE: DNA
<213> ORGANISM: Homo Sapien

<400> SEQUENCE: 7
atgatgaagt gtccacaggc tttactagct atcttttggc ttctactgag ctgggtgagc        60
agtgaagaca aggtggtaca aagccctcta tctctggttg tccacgaggg agacactgta       120
actctcaatt gcagttatga agtgactaac tttcgaagcc tactatggta caagcaggaa       180
aagaaagctc ccacatttct atttatgcta acttcaagtg gaattgaaaa gaagtcagga       240
agactaagta gcatattaga taagaaagaa cttttcagca tcctgaacat acagccacc        300 cagaccggag actcggccgt ctacctctgt gctgtgataa ctggtggtac tagctatgga       360
aagctgacat ttggacaagg gaccatcttg actgtccatc aaatatcca gaaccctgac       420 cctgccgtgt accagctgag agactctaaa tccagtgaca agtctgtctg cctattcacc       480
gattttgatt ctcaaacaaa tgtgtcacaa gtaaggatt ctgatgtgta tatcacagac       540
aaaactgtgc tagacatgag gtctatggac ttcaagagca acagtgctgt ggcctggagc       600
aacaaatctg actttgcatg tgcaaacgcc ttcaacaaca gcattattcc agaagacacc       660
ttcttcccca gcccagaaag ttcctgtgat gtcaagctgg tcgagaaaag ctttgaaaca       720
gatacgaacc taaactttca aaacctgtca gtgattgggt tccgaatcct cctcctgaaa       780
gtggccgggt ttaatctgct catgacgctg cggctgtggt ccagctga                   828

<210> SEQ ID NO 8
<211> LENGTH: 275
<212> TYPE: PRT
<213> ORGANISM: Homo Sapien

<400> SEQUENCE: 8

```
Met Met Lys Cys Pro Gln Ala Leu Leu Ala Ile Phe Trp Leu Leu Leu
1               5                   10                  15

Ser Trp Val Ser Ser Glu Asp Lys Val Val Gln Ser Pro Leu Ser Leu
            20                  25                  30

Val Val His Glu Gly Asp Thr Val Thr Leu Asn Cys Ser Tyr Glu Val
            35                  40                  45

Thr Asn Phe Arg Ser Leu Leu Trp Tyr Lys Gln Glu Lys Lys Ala Pro
50                  55                  60

Thr Phe Leu Phe Met Leu Thr Ser Ser Gly Ile Glu Lys Lys Ser Gly
65                  70                  75                  80

Arg Leu Ser Ser Ile Leu Asp Lys Lys Glu Leu Phe Ser Ile Leu Asn
                85                  90                  95

Ile Thr Ala Thr Gln Thr Gly Asp Ser Ala Val Tyr Leu Cys Ala Val
            100                 105                 110

Ile Thr Gly Gly Thr Ser Tyr Gly Lys Leu Thr Phe Gly Gln Gly Thr
            115                 120                 125

Ile Leu Thr Val His Pro Asn Ile Gln Asn Pro Asp Pro Ala Val Tyr
130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
            195                 200                 205

Asn Ala Phe Asn Asn Ser Ile Ile Pro Glu Asp Thr Phe Phe Pro Ser
210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 9
<211> LENGTH: 831
<212> TYPE: DNA
<213> ORGANISM: Homo Sapien

<400> SEQUENCE: 9
atgatgaagt gtccacaggc tttactagct atcttttggc ttctactgag ctgggtgagc      60
agtgaagaca ggtggtaca aagccctcta tctctggttg tccacgaggg agacactgta     120
actctcaatt gcagttatga agtgactaac tttcgaagcc tactatggta caagcaggaa     180
aagaaagctc ccacatttct atttatgcta acttcaagtg gaattgaaaa gaagtcagga     240
agactaagta gcatattaga taagaaagaa cttttcagca tcctgaacat cacagccacc     300
cagaccggag actcagccac ttatctctgt gctgtgcaga tgctggtgg tactagctat     360 ggaaagctga catttggaca agggaccatc ttgactgtcc atccaaatat ccagaaccct     420
gaccctgccg tgtaccagct gagagactct aaatccagtg acaagtctgt ctgcctattc     480
```

```
accgattttg attctcaaac aaatgtgtca caaagtaagg attctgatgt gtatatcaca      540
gacaaaactg tgctagacat gaggtctatg gacttcaaga gcaacagtgc tgtggcctgg      600
agcaacaaat ctgactttgc atgtgcaaac gccttcaaca acagcattat tccagaagac      660
accttcttcc ccagcccaga aagttcctgt gatgtcaagc tggtcgagaa aagctttgaa      720
acagatacga acctaaactt tcaaaacctg tcagtgattg ggttccgaat cctcctcctg      780
aaagtggccg ggtttaatct gctcatgacg ctgcggctgt ggtccagctg a               831
```

<210> SEQ ID NO 10
<211> LENGTH: 276
<212> TYPE: PRT
<213> ORGANISM: Homo Sapien

<400> SEQUENCE: 10

```
Met Met Lys Cys Pro Gln Ala Leu Leu Ala Ile Phe Trp Leu Leu Leu
1               5                   10                  15

Ser Trp Val Ser Ser Glu Asp Lys Val Val Gln Ser Pro Leu Ser Leu
            20                  25                  30

Val Val His Glu Gly Asp Thr Val Thr Leu Asn Cys Ser Tyr Glu Val
        35                  40                  45

Thr Asn Phe Arg Ser Leu Leu Trp Tyr Lys Gln Glu Lys Lys Ala Pro
    50                  55                  60

Thr Phe Leu Phe Met Leu Thr Ser Ser Gly Ile Glu Lys Lys Ser Gly
65                  70                  75                  80

Arg Leu Ser Ser Ile Leu Asp Lys Lys Glu Leu Phe Ser Ile Leu Asn
                85                  90                  95

Ile Thr Ala Thr Gln Thr Gly Asp Ser Ala Thr Tyr Leu Cys Ala Val
            100                 105                 110

Gln Asn Ala Gly Gly Thr Ser Tyr Gly Lys Leu Thr Phe Gly Gln Gly
        115                 120                 125

Thr Ile Leu Thr Val His Pro Asn Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275
```

<210> SEQ ID NO 11
<211> LENGTH: 825
<212> TYPE: DNA
<213> ORGANISM: Homo Sapien

<400> SEQUENCE: 11

```
atgatgaagt gtccacaggc tttactagct atctttggc ttctactgag ctgggtgagc        60
agtgaagaca aggtggtaca aagccctcta tctctggttg tccacgaggg agacactgta       120
actctcaatt gcagttatga agtgactaac tttcgaagcc tactatggta caagcaggaa       180
aagaaagctc ccacatttct atttatgcta acttcaagtg gaattgaaaa gaagtcagga       240
agactaagta gcatattaga taagaaagaa cttttcagca tcctgaacat acagccacc        300
cagaccggag actcggccgt ctacctctgt gctgtgctta cccaaactgg ggcaaacaac       360
ctcttctttg ggactggaac gagactcacc gttattccct atatccagaa ccctgaccct       420
gccgtgtacc agctgagaga ctctaaatcc agtgacaagt ctgtctgcct attcaccgat       480
tttgattctc aaacaaatgt gtcacaaagt aaggattctg atgtgtatat cacagacaaa       540
actgtgctag acatgaggtc tatggacttc aagagcaaca gtgctgtggc ctggagcaac       600
aaatctgact tgcatgtgc aaacgccttc aacaacagca ttattccaga agacaccttc        660
ttccccagcc agaaagttc ctgtgatgtc aagctggtcg agaaaagctt tgaaacagat        720
acgaacctaa actttcaaaa cctgtcagtg attgggttcc gaatcctcct cctgaaagtg       780
gccgggttta atctgctcat gacgctgcgg ctgtggtcca gctga                       825
```

<210> SEQ ID NO 12
<211> LENGTH: 274
<212> TYPE: PRT
<213> ORGANISM: Homo Sapien

<400> SEQUENCE: 12

```
Met Met Lys Cys Pro Gln Ala Leu Leu Ala Ile Phe Trp Leu Leu Leu
1               5                   10                  15

Ser Trp Val Ser Ser Glu Asp Lys Val Val Gln Ser Pro Leu Ser Leu
            20                  25                  30

Val Val His Glu Gly Asp Thr Val Thr Leu Asn Cys Ser Tyr Glu Val
        35                  40                  45

Thr Asn Phe Arg Ser Leu Leu Trp Tyr Lys Gln Glu Lys Lys Ala Pro
    50                  55                  60

Thr Phe Leu Phe Met Leu Thr Ser Ser Gly Ile Glu Lys Lys Ser Gly
65                  70                  75                  80

Arg Leu Ser Ser Ile Leu Asp Lys Lys Glu Leu Phe Ser Ile Leu Asn
                85                  90                  95

Ile Thr Ala Thr Gln Thr Gly Asp Ser Ala Val Tyr Leu Cys Ala Val
            100                 105                 110

Leu Thr Gln Thr Gly Ala Asn Asn Leu Phe Phe Gly Thr Gly Thr Arg
        115                 120                 125

Leu Thr Val Ile Pro Tyr Ile Gln Asn Pro Asp Pro Ala Val Tyr Gln
    130                 135                 140

Leu Arg Asp Ser Lys Ser Ser Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
```

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
            245                 250                 255

Leu Leu Lys Val Ala Gly Phe Asn Leu Met Thr Leu Arg Leu Trp
        260                 265                 270

Ser Ser

<210> SEQ ID NO 13
<211> LENGTH: 834
<212> TYPE: DNA
<213> ORGANISM: Homo Sapien

<400> SEQUENCE: 13
atggagaaaa tgttggagtg tgcattcata gtcttgtggc ttcagcttgg ctggttgagt      60
ggagaagacc aggtgacgca gagtcccgag gccctgagac tccaggaggg agagagtagc    120
agtctcaact gcagttacac agtcagcggt ttaagagggc tgttctggta taggcaagat    180
cctgggaaag gccctgaatt cctcttcacc ctgtattcag ctggggaaga aaaggagaaa    240
gaaaggctaa agccacatt aacaaagaag gaaagctttc tgcacatcac agcccctaaa    300
cctgaagact cagccactta tctctgtgct gtgcaggcct taaggaataa tgctggcaac    360
aaccgtaagc tgatttgggg attgggaaca agcctggcag taaatccgaa atccagaac    420 cctgaccctg ccgtgtacca gctgagagac tctaaatcca gtgacaagtc tgtctgccta    480
ttcaccgatt ttgattctca aacaaatgtg tcacaaagta aggattctga tgtgtatatc    540
acagacaaaa ctgtgctaga catgaggtct atgacttca agagcaacag tgctgtggcc    600
tggagcaaca atctgactt tgcatgtgca aacgccttca caacagcat tattccagaa    660 gacaccttct tccccagccc agaaagttcc tgtgatgtca agctggtcga gaaaagcttt    720
gaaacagata cgaacctaaa ctttcaaaac ctgtcagtga ttgggttccg aatcctcctc    780
ctgaaagtgg ccgggtttaa tctgctcatg acgctgcggc tgtggtccag ctga          834

<210> SEQ ID NO 14
<211> LENGTH: 277
<212> TYPE: PRT
<213> ORGANISM: Homo Sapien

<400> SEQUENCE: 14

Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Ser Leu Asn Cys Ser Tyr Thr Val
        35                  40                  45

Ser Gly Leu Arg Gly Leu Phe Trp Tyr Arg Gln Asp Pro Gly Lys Gly
    50                  55                  60

Pro Glu Phe Leu Phe Thr Leu Tyr Ser Ala Gly Glu Glu Lys Glu Lys
65                  70                  75                  80

Glu Arg Leu Lys Ala Thr Leu Thr Lys Lys Glu Ser Phe Leu His Ile
                85                  90                  95

Thr Ala Pro Lys Pro Glu Asp Ser Ala Thr Tyr Leu Cys Ala Val Gln
            100                 105                 110

Ala Leu Arg Asn Asn Ala Gly Asn Asn Arg Lys Leu Ile Trp Gly Leu

```
                115              120              125
Gly Thr Ser Leu Ala Val Asn Pro Asn Ile Gln Asn Pro Asp Pro Ala
            130              135              140

Val Tyr Gln Leu Arg Asp Ser Lys Ser Asp Lys Ser Val Cys Leu
145                 150                  155                 160

Phe Thr Asp Phe Asp Ser Gln Thr Asn Val Ser Gln Ser Lys Asp Ser
                165              170              175

Asp Val Tyr Ile Thr Asp Lys Thr Val Leu Asp Met Arg Ser Met Asp
            180              185              190

Phe Lys Ser Asn Ser Ala Val Ala Trp Ser Asn Lys Ser Asp Phe Ala
                195              200              205

Cys Ala Asn Ala Phe Asn Asn Ser Ile Ile Pro Glu Asp Thr Phe Phe
            210              215              220

Pro Ser Pro Glu Ser Ser Cys Asp Val Lys Leu Val Glu Lys Ser Phe
225                 230                  235                 240

Glu Thr Asp Thr Asn Leu Asn Phe Gln Asn Leu Ser Val Ile Gly Phe
                245              250              255

Arg Ile Leu Leu Leu Lys Val Ala Gly Phe Asn Leu Leu Met Thr Leu
            260              265              270

Arg Leu Trp Ser Ser
            275

<210> SEQ ID NO 15
<211> LENGTH: 930
<212> TYPE: DNA
<213> ORGANISM: Artificial Sequence
<220> FEATURE:
<223> OTHER INFORMATION: Synthetic Construct

<400> SEQUENCE: 15
atgatgcggc ccatcgtgct ggtgctgctg tttgccacat ctgccctggc cggcgtgacc     60 cagacccota gatacctgat caagaccaga ggccagcagg tcacactgag ctgcagccct    120
atcagcggcc acagaagcgt gtcctggtat cagcagaccc caggccaggg cctgcagttc    180
ctgttcgagt acttcagcga cacacagcgg aacaagggca acttccccgg cagattcagc    240
ggcagacagt tcagcaacag ccgcagcgag atgaacgtgt ccaccctgga actgggcgac    300
agcgccctgt acctgtgtgc ctcttctctg ggctggcggg aaacctacaa cgagcagttc    360
ttcggccctg gcaccagact gaccgtgctg aagatctga agaacgtgtt ccccccagag     420
gtggccgtgt cgagccttc tgaggccgag atcagccaca cccagaaagc caccctcgtg    480
tgtctggcca ccggcttcta ccccgaccac gtggaactgt cttggtgggt caacggcaaa    540
gaggtgcaca cgccgtcag caccgaccct cagcctctga agagcagcc cgccctgaac    600 gacagccggt actgtctgag cagcagactg agagtgtccg ccaccttctg gcagaacccc    660
cggaaccact tcagatgcca ggtgcagttc tacggcctga gcgagaacga cgagtggacc    720
caggacagag ccaagcctgt gacccagatc gtgtctgccg aggcttgggg cagagccgat    780
tgcggcttta ccagcgagag ctaccagcag ggcgtgctga gcgccaccat cctgtacgag    840
atcctgctgg gcaaggccac cctgtatgcc gtgctggtgt cagccctggt gctgatggct    900
atggtcaagc ggaaggacag ccgcggctga                                    930

<210> SEQ ID NO 16
<211> LENGTH: 309
<212> TYPE: PRT
<213> ORGANISM: Artificial Sequence
```

<220> FEATURE:
<223> OTHER INFORMATION: Synthetic Contruct

<400> SEQUENCE: 16

Met Met Arg Pro Ile Val Leu Val Leu Leu Phe Ala Thr Ser Ala Leu
1               5                   10                  15

Ala Gly Val Thr Gln Thr Pro Arg Tyr Leu Ile Lys Thr Arg Gly Gln
            20                  25                  30

Gln Val Thr Leu Ser Cys Ser Pro Ile Ser Gly His Arg Ser Val Ser
        35                  40                  45

Trp Tyr Gln Gln Thr Pro Gly Gln Gly Leu Gln Phe Leu Phe Glu Tyr
    50                  55                  60

Phe Ser Glu Thr Gln Arg Asn Lys Gly Asn Phe Pro Gly Arg Phe Ser
65                  70                  75                  80

Gly Arg Gln Phe Ser Asn Ser Arg Ser Glu Met Asn Val Ser Thr Leu
                85                  90                  95

Glu Leu Gly Asp Ser Ala Leu Tyr Leu Cys Ala Ser Ser Leu Gly Trp
            100                 105                 110

Arg Glu Thr Tyr Asn Glu Gln Phe Phe Gly Pro Gly Thr Arg Leu Thr
        115                 120                 125

Val Leu Glu Asp Leu Lys Asn Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Ser Arg Gly
305

<210> SEQ ID NO 17
<211> LENGTH: 18
<212> TYPE: DNA
<213> ORGANISM: Homo Sapien

<400> SEQUENCE: 17 gaccgggct cccagagc                                                    18

<210> SEQ ID NO 18
<211> LENGTH: 6
<212> TYPE: PRT

```
<213> ORGANISM: Homo Sapien

<400> SEQUENCE: 18

Asp Arg Gly Ser Gln Ser
1               5

<210> SEQ ID NO 19
<211> LENGTH: 15
<212> TYPE: DNA
<213> ORGANISM: Homo Sapien

<400> SEQUENCE: 19
atgaaccatg agtat                                                       15

<210> SEQ ID NO 20
<211> LENGTH: 5
<212> TYPE: PRT
<213> ORGANISM: Homo Sapien

<400> SEQUENCE: 20

Met Asn His Glu Tyr
1               5

<210> SEQ ID NO 21
<211> LENGTH: 15
<212> TYPE: DNA
<213> ORGANISM: Homo Sapien

<400> SEQUENCE: 21
atgaaccatg agtat                                                       15

<210> SEQ ID NO 22
<211> LENGTH: 5
<212> TYPE: PRT
<213> ORGANISM: Homo Sapien

<400> SEQUENCE: 22

Met Asn His Glu Tyr
1               5

<210> SEQ ID NO 23
<211> LENGTH: 18
<212> TYPE: DNA
<213> ORGANISM: Homo Sapien

<400> SEQUENCE: 23
gtgactaact ttcgaagc                                                    18

<210> SEQ ID NO 24
<211> LENGTH: 6
<212> TYPE: PRT
<213> ORGANISM: Homo Sapien

<400> SEQUENCE: 24

Val Thr Asn Phe Arg Ser
1               5

<210> SEQ ID NO 25
<211> LENGTH: 18
<212> TYPE: DNA
<213> ORGANISM: Homo Sapien

<400> SEQUENCE: 25
gtgactaact ttcgaagc                                                    18
```

<210> SEQ ID NO 26
<211> LENGTH: 6
<212> TYPE: PRT
<213> ORGANISM: Homo Sapien

<400> SEQUENCE: 26

Val Thr Asn Phe Arg Ser
1               5

<210> SEQ ID NO 27
<211> LENGTH: 18
<212> TYPE: DNA
<213> ORGANISM: Homo Sapien

<400> SEQUENCE: 27
gtgactaact ttcgaagc                                              18

<210> SEQ ID NO 28
<211> LENGTH: 6
<212> TYPE: PRT
<213> ORGANISM: Homo Sapien

<400> SEQUENCE: 28

Val Thr Asn Phe Arg Ser
1               5

<210> SEQ ID NO 29
<211> LENGTH: 18
<212> TYPE: DNA
<213> ORGANISM: Homo Sapien

<400> SEQUENCE: 29
gtcagcggtt taagaggg                                              18

<210> SEQ ID NO 30
<211> LENGTH: 6
<212> TYPE: PRT
<213> ORGANISM: Homo Sapien

<400> SEQUENCE: 30

Val Ser Gly Leu Arg Gly
1               5

<210> SEQ ID NO 31
<211> LENGTH: 15
<212> TYPE: DNA
<213> ORGANISM: Homo Sapien

<400> SEQUENCE: 31
agcggccaca gaagc                                                 15

<210> SEQ ID NO 32
<211> LENGTH: 5
<212> TYPE: PRT
<213> ORGANISM: Homo Sapien

<400> SEQUENCE: 32

Ser Gly His Arg Ser
1               5

<210> SEQ ID NO 33
<211> LENGTH: 18
<212> TYPE: DNA

<213> ORGANISM: Homo Sapien

<400> SEQUENCE: 33
atctacagca acggcgac					18

<210> SEQ ID NO 34
<211> LENGTH: 6
<212> TYPE: PRT
<213> ORGANISM: Homo Sapien

<400> SEQUENCE: 34

Ile Tyr Ser Asn Gly Asp
1               5

<210> SEQ ID NO 35
<211> LENGTH: 18
<212> TYPE: DNA
<213> ORGANISM: Homo sapien

<400> SEQUENCE: 35
tcaatgaatg ttgaggtg					18

<210> SEQ ID NO 36
<211> LENGTH: 6
<212> TYPE: PRT
<213> ORGANISM: Homo Sapien

<400> SEQUENCE: 36

Ser Met Asn Val Glu Val
1               5

<210> SEQ ID NO 37
<211> LENGTH: 18
<212> TYPE: DNA
<213> ORGANISM: Homo Sapien

<400> SEQUENCE: 37
tcaatgaatg ttgaggtg					18

<210> SEQ ID NO 38
<211> LENGTH: 6
<212> TYPE: PRT
<213> ORGANISM: Homo Sapien

<400> SEQUENCE: 38

Ser Met Asn Val Glu Val
1               5

<210> SEQ ID NO 39
<211> LENGTH: 21
<212> TYPE: DNA
<213> ORGANISM: Homo Sapien

<400> SEQUENCE: 39
ctaacttcaa gtggaattga a					21

<210> SEQ ID NO 40
<211> LENGTH: 7
<212> TYPE: PRT
<213> ORGANISM: Homo Sapien

<400> SEQUENCE: 40

Leu Thr Ser Ser Gly Ile Glu
1               5

<210> SEQ ID NO 41
<211> LENGTH: 21
<212> TYPE: DNA
<213> ORGANISM: Homo Sapien

<400> SEQUENCE: 41
ctaacttcaa gtggaattga a                                              21

<210> SEQ ID NO 42
<211> LENGTH: 7
<212> TYPE: PRT
<213> ORGANISM: Homo Sapien

<400> SEQUENCE: 42

Leu Thr Ser Ser Gly Ile Glu
1               5

<210> SEQ ID NO 43
<211> LENGTH: 21
<212> TYPE: DNA
<213> ORGANISM: Homo Sapien

<400> SEQUENCE: 43
ctaacttcaa gtggaattga a                                              21

<210> SEQ ID NO 44
<211> LENGTH: 7
<212> TYPE: PRT
<213> ORGANISM: Homo Sapien

<400> SEQUENCE: 44

Leu Thr Ser Ser Gly Ile Glu
1               5

<210> SEQ ID NO 45
<211> LENGTH: 21
<212> TYPE: DNA
<213> ORGANISM: Homo Sapien

<400> SEQUENCE: 45
ctgtattcag ctggggaaga a                                              21

<210> SEQ ID NO 46
<211> LENGTH: 7
<212> TYPE: PRT
<213> ORGANISM: Homo Sapien

<400> SEQUENCE: 46

Leu Tyr Ser Ala Gly Glu Glu
1               5

<210> SEQ ID NO 47
<211> LENGTH: 18
<212> TYPE: DNA
<213> ORGANISM: Homo Sapien

<400> SEQUENCE: 47
tacttcagcg agacacag                                                  18

<210> SEQ ID NO 48
<211> LENGTH: 6
<212> TYPE: PRT
<213> ORGANISM: Homo Sapien

<400> SEQUENCE: 48

Tyr Phe Ser Glu Thr Gln
1               5

<210> SEQ ID NO 49
<211> LENGTH: 39
<212> TYPE: DNA
<213> ORGANISM: Homo Sapien

<400> SEQUENCE: 49
tgtgccgtgt ccatcggctt cggcaacgtg ctgcactgc                    39

<210> SEQ ID NO 50
<211> LENGTH: 13
<212> TYPE: PRT
<213> ORGANISM: Homo Sapien

<400> SEQUENCE: 50

Cys Ala Val Ser Ile Gly Phe Gly Asn Val Leu His Cys
1               5                   10

<210> SEQ ID NO 51
<211> LENGTH: 39
<212> TYPE: DNA
<213> ORGANISM: Homo Sapien

<400> SEQUENCE: 51
tgtgccagca gtctactcgg ggactatggc tacaccttc                    39

<210> SEQ ID NO 52
<211> LENGTH: 13
<212> TYPE: PRT
<213> ORGANISM: Homo Sapien

<400> SEQUENCE: 52

Cys Ala Ser Ser Leu Leu Gly Asp Tyr Gly Tyr Thr Phe
1               5                   10

<210> SEQ ID NO 53
<211> LENGTH: 39
<212> TYPE: DNA
<213> ORGANISM: Homo Sapien

<400> SEQUENCE: 53
tgtgccagca gtttaggggg tgcctacgag cagtacttc                    39

<210> SEQ ID NO 54
<211> LENGTH: 13
<212> TYPE: PRT
<213> ORGANISM: Homo Sapien

<400> SEQUENCE: 54

Cys Ala Ser Ser Leu Gly Gly Ala Tyr Glu Gln Tyr Phe
1               5                   10

<210> SEQ ID NO 55
<211> LENGTH: 45
<212> TYPE: DNA
<213> ORGANISM: Homo Sapien

<400> SEQUENCE: 55
tgtgctgtga taactggtgg tactagctat ggaaagctga cattt              45

<210> SEQ ID NO 56
<211> LENGTH: 15
<212> TYPE: PRT
<213> ORGANISM: Homo Sapien

<400> SEQUENCE: 56

Cys Ala Val Ile Thr Gly Gly Thr Ser Tyr Gly Lys Leu Thr Phe
1               5                   10                  15

<210> SEQ ID NO 57
<211> LENGTH: 48
<212> TYPE: DNA
<213> ORGANISM: Homo Sapien

<400> SEQUENCE: 57
tgtgctgtgc agaatgctgg tggtactagc tatggaaagc tgacattt                48

<210> SEQ ID NO 58
<211> LENGTH: 16
<212> TYPE: PRT
<213> ORGANISM: Homo Sapien

<400> SEQUENCE: 58

Cys Ala Val Gln Asn Ala Gly Gly Thr Ser Tyr Gly Lys Leu Thr Phe
1               5                   10                  15

<210> SEQ ID NO 59
<211> LENGTH: 42
<212> TYPE: DNA
<213> ORGANISM: Homo Sapien

<400> SEQUENCE: 59
tgtgctgtgc ttacccaaac tggggcaaac aacctcttct tt                      42

<210> SEQ ID NO 60
<211> LENGTH: 14
<212> TYPE: PRT
<213> ORGANISM: Homo Sapien

<400> SEQUENCE: 60

Cys Ala Val Leu Thr Gln Thr Gly Ala Asn Asn Leu Phe Phe
1               5                   10

<210> SEQ ID NO 61
<211> LENGTH: 54
<212> TYPE: DNA
<213> ORGANISM: Homo Sapien

<400> SEQUENCE: 61
tgtgctgtgc aggccttaag gaataatgct ggcaacaacc gtaagctgat ttgg         54

<210> SEQ ID NO 62
<211> LENGTH: 18
<212> TYPE: PRT
<213> ORGANISM: Homo Sapien

<400> SEQUENCE: 62

Cys Ala Val Gln Ala Leu Arg Asn Asn Ala Gly Asn Asn Arg Lys Leu
1               5                   10                  15

Ile Trp

<210> SEQ ID NO 63
<211> LENGTH: 48

```
<212> TYPE: DNA
<213> ORGANISM: Homo Sapien

<400> SEQUENCE: 63
tgtgcctctt ctctgggctg gcgggaaacc tacaacgagc agttcttc                    48

<210> SEQ ID NO 64
<211> LENGTH: 16
<212> TYPE: PRT
<213> ORGANISM: Homo Sapien

<400> SEQUENCE: 64

Cys Ala Ser Ser Leu Gly Trp Arg Glu Thr Tyr Asn Glu Gln Phe Phe
1               5                   10                  15

<210> SEQ ID NO 65
<211> LENGTH: 12
<212> TYPE: DNA
<213> ORGANISM: Homo Sapien

<400> SEQUENCE: 65
agggccaaga ga                                                          12

<210> SEQ ID NO 66
<211> LENGTH: 4
<212> TYPE: PRT
<213> ORGANISM: Homo Sapien

<400> SEQUENCE: 66

Arg Ala Lys Arg
1

<210> SEQ ID NO 67
<211> LENGTH: 12
<212> TYPE: DNA
<213> ORGANISM: Homo Sapien

<400> SEQUENCE: 67
tctggatctg gc                                                          12

<210> SEQ ID NO 68
<211> LENGTH: 4
<212> TYPE: PRT
<213> ORGANISM: Homo Sapien

<400> SEQUENCE: 68

Ser Gly Ser Gly
1

<210> SEQ ID NO 69
<211> LENGTH: 72
<212> TYPE: DNA
<213> ORGANISM: Foot-and-mouth disease virus

<400> SEQUENCE: 69
gcccctgtga agcagaccct gaacttcgac ctgctgaagc tggccggcga cgtggaaagc      60
aaccctggcc cc                                                          72

<210> SEQ ID NO 70
<211> LENGTH: 24
<212> TYPE: PRT
<213> ORGANISM: Foot-and-mouth disease virus

<400> SEQUENCE: 70
```

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 71
<211> LENGTH: 804
<212> TYPE: DNA
<213> ORGANISM: Homo Sapien

<400> SEQUENCE: 71

```
atggacgggc cgcgcctgct gctgttgctg cttctggggg tgtcccttgg aggtgccaag      60
gaggcatgcc ccacaggcct gtacacacac agcggtgagt gctgcaaagc ctgcaacctg     120
ggcgagggtg tggcccagcc ttgtggagcc aaccagaccg tgtgtgagcc ctgcctggac     180
agcgtgacgt tctccgacgt ggtgagcgcg accgagccgt gcaagccgtg caccgagtgc     240
gtggggctcc agagcatgtc ggcgccatgc gtggaggccg acgacgccgt gtgccgctgc     300
gcctacggct actaccagga tgagacgact gggcgctgcg aggcgtgccg cgtgtgcgag     360
gcgggctcgg gcctcgtgtt ctcctgccag gacaagcaga acaccgtgtg cgaggagtgc     420
cccgacggca cgtattccga cgaggccaac cacgtggacc cgtgcctgcc ctgcaccgtg     480
tgcgaggaca ccgagcgcca gctccgcgag tgcacgcgct gggccgacgc cgagtgcgag     540
gagatccctg gccgttggat tacacggtcc acaccccag agggctcgga cagcacagcc     600
cccagcaccc aggagcctga ggcacctcca gaacaagacc tcatagccag cacggtggca     660
ggtgtggtga ccacagtgat gggcagctcc cagcccgtgg tgacccgagg caccaccgac     720
aacctcatcc ctgtctattg ctccatcctg gctgctgtgg ttgtgggtct tgtggcctac     780
atagccttca gaggtggaaa cagc                                            804
```

<210> SEQ ID NO 72
<211> LENGTH: 268
<212> TYPE: PRT
<213> ORGANISM: Homo Sapien

<400> SEQUENCE: 72

Met Asp Gly Pro Arg Leu Leu Leu Leu Leu Leu Gly Val Ser Leu
1               5                   10                  15

Gly Gly Ala Lys Glu Ala Cys Pro Thr Gly Leu Tyr Thr His Ser Gly
            20                  25                  30

Glu Cys Cys Lys Ala Cys Asn Leu Gly Glu Gly Val Ala Gln Pro Cys
        35                  40                  45

Gly Ala Asn Gln Thr Val Cys Glu Pro Cys Leu Asp Ser Val Thr Phe
    50                  55                  60

Ser Asp Val Val Ser Ala Thr Glu Pro Cys Lys Pro Cys Thr Glu Cys
65                  70                  75                  80

Val Gly Leu Gln Ser Met Ser Ala Pro Cys Val Glu Ala Asp Asp Ala
                85                  90                  95

Val Cys Arg Cys Ala Tyr Gly Tyr Tyr Gln Asp Glu Thr Thr Gly Arg
            100                 105                 110

Cys Glu Ala Cys Arg Val Cys Glu Ala Gly Ser Gly Leu Val Phe Ser
        115                 120                 125

Cys Gln Asp Lys Gln Asn Thr Val Cys Glu Glu Cys Pro Asp Gly Thr
    130                 135                 140

Tyr Ser Asp Glu Ala Asn His Val Asp Pro Cys Leu Pro Cys Thr Val

| | | | | | | | 145 | | | | | 150 | | | | | 155 | | | | | 160 |

Cys Glu Asp Thr Glu Arg Gln Leu Arg Glu Cys Thr Arg Trp Ala Asp
                165                    170                    175

Ala Glu Cys Glu Glu Ile Pro Gly Arg Trp Ile Thr Arg Ser Thr Pro
                180                    185                    190

Pro Glu Gly Ser Asp Ser Thr Ala Pro Ser Thr Gln Glu Pro Glu Ala
            195                    200                    205

Pro Pro Glu Gln Asp Leu Ile Ala Ser Thr Val Ala Gly Val Val Thr
210                    215                    220

Thr Val Met Gly Ser Ser Gln Pro Val Val Thr Arg Gly Thr Thr Asp
225                    230                    235                    240

Asn Leu Ile Pro Val Tyr Cys Ser Ile Leu Ala Ala Val Val Val Gly
                245                    250                    255

Leu Val Ala Tyr Ile Ala Phe Lys Arg Trp Asn Ser
            260                    265

<210> SEQ ID NO 73
<211> LENGTH: 9
<212> TYPE: PRT
<213> ORGANISM: Homo Sapien

<400> SEQUENCE: 73

Ala Ala Gly Ile Gly Ile Leu Thr Val
1               5

<210> SEQ ID NO 74
<211> LENGTH: 9
<212> TYPE: PRT
<213> ORGANISM: Homo Sapien

<400> SEQUENCE: 74

Cys Tyr Thr Trp Asn Gln Met Asn Leu
1               5

<210> SEQ ID NO 75
<211> LENGTH: 51
<212> TYPE: DNA
<213> ORGANISM: Artificial Sequence
<220> FEATURE:
<223> OTHER INFORMATION: Synthetic Construct

<400> SEQUENCE: 75
atcccagtgt ggtggtacgg gaattctgcc atgggccccc agctccttgg c        51

<210> SEQ ID NO 76
<211> LENGTH: 56
<212> TYPE: DNA
<213> ORGANISM: Artificial Sequence
<220> FEATURE:
<223> OTHER INFORMATION: Synthetic Construct

<400> SEQUENCE: 76
atcgtcgacc actgtgctgg cggccgctcg agttccaggg ctgccttcag aaatcc      56

<210> SEQ ID NO 77
<211> LENGTH: 59
<212> TYPE: DNA
<213> ORGANISM: Artificial Sequence
<220> FEATURE:
<223> OTHER INFORMATION: Synthetic Construct

<400> SEQUENCE: 77

```
gaccactgtg ctggcggccg ctcgagctag cctctggaat cctttctctt gaccattgc        59
```

<210> SEQ ID NO 78
<211> LENGTH: 24
<212> TYPE: DNA
<213> ORGANISM: Artificial Sequence
<220> FEATURE:
<223> OTHER INFORMATION: Synthetic Construct

<400> SEQUENCE: 78

```
ggagagttcc ctctgtttgg agag                                              24
```

<210> SEQ ID NO 79
<211> LENGTH: 43
<212> TYPE: DNA
<213> ORGANISM: Artificial Sequence
<220> FEATURE:
<223> OTHER INFORMATION: Synthetic Construct

<400> SEQUENCE: 79

```
gtgtggtggt acgggaattc aagcagtggt atcaacgcag agt                         43
```

<210> SEQ ID NO 80
<211> LENGTH: 43
<212> TYPE: DNA
<213> ORGANISM: Artificial Sequence
<220> FEATURE:
<223> OTHER INFORMATION: Synthetic Construct

<400> SEQUENCE: 80

```
accactgtgc tggcggccgc tcagctggac cacagccgca gcg                         43
```

<210> SEQ ID NO 81
<211> LENGTH: 15
<212> TYPE: PRT
<213> ORGANISM: Homo Sapien

<400> SEQUENCE: 81

```
Cys Ala Ser Ser Leu Leu Gly Gly Ser Thr Asp Thr Gln Tyr Phe
1               5                   10                  15
```

<210> SEQ ID NO 82
<211> LENGTH: 15
<212> TYPE: PRT
<213> ORGANISM: Homo Sapien

<400> SEQUENCE: 82

```
Cys Ala Ser Ser Pro Ile Asp Gly Leu Asn Thr Glu Ala Phe Phe
1               5                   10                  15
```

<210> SEQ ID NO 83
<211> LENGTH: 11
<212> TYPE: PRT
<213> ORGANISM: Homo Sapien

<400> SEQUENCE: 83

```
Cys Ala Ser Ser Phe Asn Asp Glu Gln Phe Phe
1               5                   10
```

<210> SEQ ID NO 84
<211> LENGTH: 15
<212> TYPE: PRT
<213> ORGANISM: Homo Sapien

<400> SEQUENCE: 84

```
Cys Ala Ser Ser Pro Ser Gln Gly Gly Asn Thr Glu Ala Phe Phe
1               5                   10                  15
```

<210> SEQ ID NO 85
<211> LENGTH: 14
<212> TYPE: PRT
<213> ORGANISM: Homo Sapien

<400> SEQUENCE: 85

```
Cys Ala Ser Ser Asp Ser Thr Ala Ser Ser Glu Gln Phe Phe
1               5                   10
```

<210> SEQ ID NO 86
<211> LENGTH: 14
<212> TYPE: PRT
<213> ORGANISM: Homo Sapien

<400> SEQUENCE: 86

```
Cys Ala Ser Ser Leu Ser Gly Ser Gly Asp Glu Gln Phe Phe
1               5                   10
```

<210> SEQ ID NO 87
<211> LENGTH: 13
<212> TYPE: PRT
<213> ORGANISM: Homo Sapien

<400> SEQUENCE: 87

```
Cys Ala Ser Ser Leu Ser Phe Gly Thr Glu Ala Phe Phe
1               5                   10
```

<210> SEQ ID NO 88
<211> LENGTH: 13
<212> TYPE: PRT
<213> ORGANISM: Homo Sapien

<400> SEQUENCE: 88

```
Cys Ala Ser Ser Leu His Gly Pro Gly Gly Tyr Thr Phe
1               5                   10
```

<210> SEQ ID NO 89
<211> LENGTH: 11
<212> TYPE: PRT
<213> ORGANISM: Homo Sapien

<400> SEQUENCE: 89

```
Cys Ala Ser Gly Pro Ser Tyr Glu Gln Tyr Phe
1               5                   10
```

<210> SEQ ID NO 90
<211> LENGTH: 10
<212> TYPE: PRT
<213> ORGANISM: Homo Sapien

<400> SEQUENCE: 90

```
Cys Ala Ser Gly Ser Tyr Glu Gln Tyr Phe
1               5                   10
```

<210> SEQ ID NO 91
<211> LENGTH: 16
<212> TYPE: PRT
<213> ORGANISM: Homo Sapien

<400> SEQUENCE: 91

```
Cys Ala Ser Ser Val Phe Gly Gly Asp Met Gly Glu Lys Leu Phe Phe
1               5                   10                  15
```

<210> SEQ ID NO 92
<211> LENGTH: 14
<212> TYPE: PRT
<213> ORGANISM: Homo Sapien

<400> SEQUENCE: 92

Cys Ala Val Gln Ala Val Asp Ser Asn Tyr Gln Leu Ile Trp
1               5                   10

<210> SEQ ID NO 93
<211> LENGTH: 933
<212> TYPE: DNA
<213> ORGANISM: Homo Sapien

<400> SEQUENCE: 93

| | | | | | |
|---|---|---|---|---|---|
| atgggccccc | agctccttgg | ctatgtggtc | ctttgccttc | taggagcagg | ccccctggaa | 60 |
| gcccaagtga | cccagaaccc | aagataccte | atcacagtga | ctggaaagaa | gttaacagtg | 120 |
| acttgttctc | agaatatgaa | ccatgagtat | atgtcctggt | atcgacaaga | cccagggctg | 180 |
| ggcttaaggc | agatctacta | ttcaatgaat | gttgaggtga | ctgataaggg | agatgttcct | 240 |
| gaagggtaca | aagtctctcg | aaaagagaag | aggaatttcc | ccctgatcct | ggagtcgccc | 300 |
| agccccaacc | agacctctct | gtacttctgt | gccagcagtc | cctgggggc | catggagcag | 360 |
| tacttcgggc | cgggcaccag | gctcacggtc | acagaggacc | tgaaaaacgt | gttcccaccc | 420 |
| gaggtcgctg | tgtttgagcc | atcagaagca | gagatctccc | acacccaaaa | ggccacactg | 480 |
| gtgtgcctgg | ccacaggctt | ctaccccgac | cacgtggagc | tgagctggtg | ggtgaatggg | 540 |
| aaggaggtgc | acagtggggt | cagcacagac | ccgcagcccc | tcaaggagca | gcccgccctc | 600 |
| aatgactcca | gatactgcct | gagcagccgc | ctgagggtct | cggccacctt | ctggcagaac | 660 |
| ccccgcaacc | acttccgctg | tcaagtccag | ttctacgggc | tctcggagaa | tgacgagtgg | 720 |
| acccaggata | gggccaaacc | cgtcacccag | atcgtcagcg | ccgaggcctg | ggtagagca | 780 |
| gactgtggct | tcacctccga | gtcttaccag | caaggggtcc | tgtctgccac | catcctctat | 840 |
| gagatcttgc | tagggaaggc | caccttgtat | gccgtgctgg | tcagtgccct | cgtgctgatg | 900 |
| gccatggtca | agagaaagga | ttccagaggc | tag | | | 933 |

<210> SEQ ID NO 94
<211> LENGTH: 311
<212> TYPE: PRT
<213> ORGANISM: Homo Sapien

<400> SEQUENCE: 94

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser

|     |     |     | 100 |     |     |     | 105 |     |     |     | 110 |     |
| --- | --- | --- | --- | --- | --- | --- | --- | --- | --- | --- | --- | --- |
| Ser | Pro | Leu | Gly | Ala | Met | Glu | Gln | Tyr | Phe | Gly | Pro | Gly | Thr | Arg | Leu |
|     |     |     | 115 |     |     |     | 120 |     |     |     | 125 |     |

Thr Val Thr Glu Asp Leu Lys Asn Val Phe Pro Glu Val Ala Val
        130             135             140

Phe Glu Pro Ser Glu Ala Glu Ile Ser His Thr Gln Lys Ala Thr Leu
145             150             155             160

Val Cys Leu Ala Thr Gly Phe Tyr Pro Asp His Val Glu Leu Ser Trp
                165             170             175

Trp Val Asn Gly Lys Glu Val His Ser Gly Val Ser Thr Asp Pro Gln
            180             185             190

Pro Leu Lys Glu Gln Pro Ala Leu Asn Asp Ser Arg Tyr Cys Leu Ser
        195             200             205

Ser Arg Leu Arg Val Ser Ala Thr Phe Trp Gln Asn Pro Arg Asn His
    210             215             220

Phe Arg Cys Gln Val Gln Phe Tyr Gly Leu Ser Glu Asn Asp Glu Trp
225             230             235             240

Thr Gln Asp Arg Ala Lys Pro Val Thr Gln Ile Val Ser Ala Glu Ala
                245             250             255

Trp Gly Arg Ala Asp Cys Gly Phe Thr Ser Glu Ser Tyr Gln Gln Gly
            260             265             270

Val Leu Ser Ala Thr Ile Leu Tyr Glu Ile Leu Leu Gly Lys Ala Thr
        275             280             285

Leu Tyr Ala Val Leu Val Ser Ala Leu Val Leu Met Ala Met Val Lys
290             295             300

Arg Lys Asp Ser Arg Gly Glx
305             310

<210> SEQ ID NO 95
<211> LENGTH: 930
<212> TYPE: DNA
<213> ORGANISM: Homo Sapien

<400> SEQUENCE: 95

```
atgggccccc agctccttgg ctatgtggtc ctttgccttc taggagcagg cccctggaa     60
gcccaagtga cccagaaccc aagatacctc atcacagtga ctggaaagaa gttaacagtg    120
acttgttctc agaatatgaa ccatgagtat atgtcctggt atcgacaaga cccagggctg    180
ggcttaaggc agatctacta ttcaatgaat gttgaggtga ctgataaggg agatgttcct    240
gaagggtaca agtctctcg aaaagagaag aggaatttcc ccctgatcct ggagtcgccc    300
agccccaacc agacctctct gtacttctgt gccagcagtc cctacatgat gaacactgaa    360
gctttctttg acaaggcac cagactcaca gttgtagagg acctgaacaa ggtgttccca    420
cccgaggtcg ctgtgtttga gccatcagaa gcagagatct cccacaccca aaaggccaca    480
ctggtgtgcc tggccacagg cttcttccct gaccacgtgg agctgagctg gtgggtgaat    540
gggaaggagg tgcacagtgg ggtcagcacg gacccgcagc cctcaaggaa gcagcccgcc    600
ctcaatgact ccagatactg cctgagcagc cgcctgaggg tctcggccac cttctggcag    660
aaccccgca accacttccg ctgtcaagtc cagttctacg gctctcggga atgacgag       720
tggacccagg atagggccaa accgtcacc cagatcgtca gcgccgaggc tgggggtaga    780
gcagactgtg gctttacctc ggtgtcctac cagcaagggg tcctgtctgc caccatcctc    840
tatgagatcc tgctagggaa ggccaccctg tatgctgtgc tggtcagcgc ccttgtgttg    900
```

```
atggccatgg tcaagagaaa ggatttctga                                        930
```

<210> SEQ ID NO 96
<211> LENGTH: 309
<212> TYPE: PRT
<213> ORGANISM: Homo Sapien

<400> SEQUENCE: 96

| | | | | | | | | | | | | | | | |
|---|---|---|---|---|---|---|---|---|---|---|---|---|---|---|---|
| Met | Gly | Pro | Gln | Leu | Leu | Gly | Tyr | Val | Val | Leu | Cys | Leu | Leu | Gly | Ala |
| 1 | | | | 5 | | | | | 10 | | | | | 15 | |
| Gly | Pro | Leu | Glu | Ala | Gln | Val | Thr | Gln | Asn | Pro | Arg | Tyr | Leu | Ile | Thr |
| | | | 20 | | | | | 25 | | | | | 30 | | |
| Val | Thr | Gly | Lys | Lys | Leu | Thr | Val | Thr | Cys | Ser | Gln | Asn | Met | Asn | His |
| | | | 35 | | | | | 40 | | | | | 45 | | |
| Glu | Tyr | Met | Ser | Trp | Tyr | Arg | Gln | Asp | Pro | Gly | Leu | Gly | Leu | Arg | Gln |
| | 50 | | | | | 55 | | | | | 60 | | | | |
| Ile | Tyr | Tyr | Ser | Met | Asn | Val | Glu | Val | Thr | Asp | Lys | Gly | Asp | Val | Pro |
| 65 | | | | | 70 | | | | | 75 | | | | | 80 |
| Glu | Gly | Tyr | Lys | Val | Ser | Arg | Lys | Glu | Lys | Arg | Asn | Phe | Pro | Leu | Ile |
| | | | | 85 | | | | | 90 | | | | | 95 | |
| Leu | Glu | Ser | Pro | Ser | Pro | Asn | Gln | Thr | Ser | Leu | Tyr | Phe | Cys | Ala | Ser |
| | | | 100 | | | | | 105 | | | | | 110 | | |
| Ser | Pro | Tyr | Met | Met | Asn | Thr | Glu | Ala | Phe | Phe | Gly | Gln | Gly | Thr | Arg |
| | | | 115 | | | | | 120 | | | | | 125 | | |
| Leu | Thr | Val | Val | Glu | Asp | Leu | Asn | Lys | Val | Phe | Pro | Pro | Glu | Val | Ala |
| 130 | | | | | 135 | | | | | 140 | | | | | |
| Val | Phe | Glu | Pro | Ser | Glu | Ala | Glu | Ile | Ser | His | Thr | Gln | Lys | Ala | Thr |
| 145 | | | | | 150 | | | | | 155 | | | | | 160 |
| Leu | Val | Cys | Leu | Ala | Thr | Gly | Phe | Phe | Pro | Asp | His | Val | Glu | Leu | Ser |
| | | | | 165 | | | | | 170 | | | | | 175 | |
| Trp | Trp | Val | Asn | Gly | Lys | Glu | Val | His | Ser | Gly | Val | Ser | Thr | Asp | Pro |
| | | | 180 | | | | | 185 | | | | | 190 | | |
| Gln | Pro | Leu | Lys | Glu | Gln | Pro | Ala | Leu | Asn | Asp | Ser | Arg | Tyr | Cys | Leu |
| | | | 195 | | | | | 200 | | | | | 205 | | |
| Ser | Ser | Arg | Leu | Arg | Val | Ser | Ala | Thr | Phe | Trp | Gln | Asn | Pro | Arg | Asn |
| | 210 | | | | | 215 | | | | | 220 | | | | |
| His | Phe | Arg | Cys | Gln | Val | Gln | Phe | Tyr | Gly | Leu | Ser | Glu | Asn | Asp | Glu |
| 225 | | | | | 230 | | | | | 235 | | | | | 240 |
| Trp | Thr | Gln | Asp | Arg | Ala | Lys | Pro | Val | Thr | Gln | Ile | Val | Ser | Ala | Glu |
| | | | | 245 | | | | | 250 | | | | | 255 | |
| Ala | Trp | Gly | Arg | Ala | Asp | Cys | Gly | Phe | Thr | Ser | Val | Ser | Tyr | Gln | Gln |
| | | | 260 | | | | | 265 | | | | | 270 | | |
| Gly | Val | Leu | Ser | Ala | Thr | Ile | Leu | Tyr | Glu | Ile | Leu | Leu | Gly | Lys | Ala |
| | | | 275 | | | | | 280 | | | | | 285 | | |
| Thr | Leu | Tyr | Ala | Val | Leu | Val | Ser | Ala | Leu | Val | Leu | Met | Ala | Met | Val |
| | 290 | | | | | 295 | | | | | 300 | | | | |
| Lys | Arg | Lys | Asp | Phe | | | | | | | | | | | |
| 305 | | | | | | | | | | | | | | | |

<210> SEQ ID NO 97
<211> LENGTH: 924
<212> TYPE: DNA
<213> ORGANISM: Homo Sapien

<400> SEQUENCE: 97

```
atgggctcca ggctgctctg ttgggtgctg ctttgtctcc tgggagcagg cccagtaaag    60
```

```
gctggagtca ctcaaactcc aagatatctg atcaaaacga gaggacagca agtgacactg    120
agctgctccc ctatctctgg gcataggagt gtatcctggt accaacagac cccaggacag    180
ggccttcagt tcctctttga atacttcagt gagacacaga gaaacaaagg aaacttccct    240
ggtcgattct cagggcgcca gttctctaac tctcgctctg agatgaatgt gagcaccttg    300
gagctggggg actcggccct ttatctttgc gccagcagct ggacagggga tggctacacc    360
ttcggttcgg ggaccaggtt aaccgttgta gaggacctga acaaggtgtt cccacccgag    420
gtcgctgtgt ttgagccatc agaagcagag atctcccaca cccaaaaggc cacactggtg    480
tgcctggcca caggcttctt ccctgaccac gtggagctga ctggtgggt gaatgggaag    540
gaggtgcaca gtggggtcag cacggacccg cagcccctca aggagcagcc cgccctcaat    600
gactccagat actgcctgag cagccgcctg agggtctcgg ccaccttctg cagaaccccc    660
cgcaaccact tccgctgtca agtccagttc tacgggctct cggagaatga cgagtggacc    720
caggataggg ccaaacccgt cacccagatc gtcagcgccg aggcctgggg tagagcagac    780
tgtggcttta cctcggtgtc ctaccagcaa ggggtcctgt ctgccaccat cctctatgag    840
atcctgctag gaaggccac cctgtatgct gtgctggtca gcgcccttgt gttgatggcc    900
atggtcaaga gaaaggattt ctga    924
```

```
<210> SEQ ID NO 98
<211> LENGTH: 308
<212> TYPE: PRT
<213> ORGANISM: Homo Sapien

<400> SEQUENCE: 98
```

```
Met Gly Ser Arg Leu Leu Cys Trp Val Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
            35                  40                  45

Arg Ser Val Ser Trp Tyr Gln Gln Thr Pro Gly Gln Gly Leu Gln Phe
        50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Trp Thr Gly Asp Gly Tyr Thr Phe Gly Ser Gly Thr Arg Leu Thr
        115                 120                 125

Val Val Glu Asp Leu Asn Lys Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
```

```
                  210                 215                 220
Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
                260                 265                 270

Leu Ser Ala Thr Ile Leu Tyr Glu Ile Leu Leu Gly Lys Ala Thr Leu
            275                 280                 285

Tyr Ala Val Leu Val Ser Ala Leu Val Leu Met Ala Met Val Lys Arg
        290                 295                 300

Lys Asp Phe Glx
305

<210> SEQ ID NO 99
<211> LENGTH: 15
<212> TYPE: DNA
<213> ORGANISM: Homo Sapien

<400> SEQUENCE: 99
atgaaccatg agtat                                                    15

<210> SEQ ID NO 100
<211> LENGTH: 5
<212> TYPE: PRT
<213> ORGANISM: Homo Sapien

<400> SEQUENCE: 100

Met Asn His Glu Tyr
1               5

<210> SEQ ID NO 101
<211> LENGTH: 15
<212> TYPE: DNA
<213> ORGANISM: Homo Sapien

<400> SEQUENCE: 101
atgaaccatg agtat                                                    15

<210> SEQ ID NO 102
<211> LENGTH: 5
<212> TYPE: PRT
<213> ORGANISM: Homo Sapien

<400> SEQUENCE: 102

Met Asn His Glu Tyr
1               5

<210> SEQ ID NO 103
<211> LENGTH: 15
<212> TYPE: DNA
<213> ORGANISM: Homo Sapien

<400> SEQUENCE: 103
tctgggcata ggagt                                                    15

<210> SEQ ID NO 104
<211> LENGTH: 5
<212> TYPE: PRT
<213> ORGANISM: Homo Sapien

<400> SEQUENCE: 104
```

Ser Gly His Arg Ser
1               5

<210> SEQ ID NO 105
<211> LENGTH: 18
<212> TYPE: DNA
<213> ORGANISM: Homo Sapien

<400> SEQUENCE: 105
tcaatgaatg ttgaggtg                                                   18

<210> SEQ ID NO 106
<211> LENGTH: 6
<212> TYPE: PRT
<213> ORGANISM: Homo Sapien

<400> SEQUENCE: 106

Ser Met Asn Val Glu Val
1               5

<210> SEQ ID NO 107
<211> LENGTH: 18
<212> TYPE: DNA
<213> ORGANISM: Homo Sapien

<400> SEQUENCE: 107
tcaatgaatg ttgaggtg                                                   18

<210> SEQ ID NO 108
<211> LENGTH: 6
<212> TYPE: PRT
<213> ORGANISM: Homo Sapien

<400> SEQUENCE: 108

Ser Met Asn Val Glu Val
1               5

<210> SEQ ID NO 109
<211> LENGTH: 18
<212> TYPE: DNA
<213> ORGANISM: Homo Sapien

<400> SEQUENCE: 109
tacttcagtg agacacag                                                   18

<210> SEQ ID NO 110
<211> LENGTH: 6
<212> TYPE: PRT
<213> ORGANISM: Homo Sapien

<400> SEQUENCE: 110

Tyr Phe Ser Glu Thr Gln
1               5

<210> SEQ ID NO 111
<211> LENGTH: 39
<212> TYPE: DNA
<213> ORGANISM: Homo Sapien

<400> SEQUENCE: 111
tgtgccagca gtcccctggg ggccatggag cagtacttc                            39

<210> SEQ ID NO 112

```
<211> LENGTH: 13
<212> TYPE: PRT
<213> ORGANISM: Homo Sapien

<400> SEQUENCE: 112

Cys Ala Ser Ser Pro Leu Gly Ala Met Glu Gln Tyr Phe
1               5                   10

<210> SEQ ID NO 113
<211> LENGTH: 42
<212> TYPE: DNA
<213> ORGANISM: Homo Sapien

<400> SEQUENCE: 113
tgtgccagca gtccctacat gatgaacact gaagctttct tt                         42

<210> SEQ ID NO 114
<211> LENGTH: 14
<212> TYPE: PRT
<213> ORGANISM: Homo Sapien

<400> SEQUENCE: 114

Cys Ala Ser Ser Pro Tyr Met Met Asn Thr Glu Ala Phe Phe
1               5                   10

<210> SEQ ID NO 115
<211> LENGTH: 36
<212> TYPE: DNA
<213> ORGANISM: Homo Sapien

<400> SEQUENCE: 115
tgcgccagca gctggacagg ggatggctac accttc                                36

<210> SEQ ID NO 116
<211> LENGTH: 12
<212> TYPE: PRT
<213> ORGANISM: Homo Sapien

<400> SEQUENCE: 116

Cys Ala Ser Ser Trp Thr Gly Asp Gly Tyr Thr Phe
1               5                   10

<210> SEQ ID NO 117
<211> LENGTH: 12
<212> TYPE: PRT
<213> ORGANISM: Homo Sapien

<400> SEQUENCE: 117

Cys Ala Ser Ser His Gly Gly Asn Glu Gln Tyr Phe
1               5                   10

<210> SEQ ID NO 118
<211> LENGTH: 13
<212> TYPE: PRT
<213> ORGANISM: Homo Sapien

<400> SEQUENCE: 118

Cys Ala Ser Ser Arg Asp Phe Gly Asn Thr Ile Tyr Phe
1               5                   10

<210> SEQ ID NO 119
<211> LENGTH: 14
<212> TYPE: PRT
<213> ORGANISM: Homo Sapien
```

```
<400> SEQUENCE: 119

Cys Ala Ser Ser Leu Ala Met Gly Ala Thr Glu Ala Phe Phe
1               5                   10

<210> SEQ ID NO 120
<211> LENGTH: 11
<212> TYPE: PRT
<213> ORGANISM: Homo Sapien

<400> SEQUENCE: 120

Cys Ala Thr Gly Val Thr Asp Thr Gln Tyr Phe
1               5                   10

<210> SEQ ID NO 121
<211> LENGTH: 11
<212> TYPE: PRT
<213> ORGANISM: Homo Sapien

<400> SEQUENCE: 121

Cys Ala Ser Ser Glu Val Ala Trp Gln Phe Phe
1               5                   10

<210> SEQ ID NO 122
<211> LENGTH: 11
<212> TYPE: PRT
<213> ORGANISM: Homo Sapien

<400> SEQUENCE: 122

Cys Ala Ser Asp Glu Gly Phe Gly Tyr Thr Phe
1               5                   10

<210> SEQ ID NO 123
<211> LENGTH: 4
<212> TYPE: PRT
<213> ORGANISM: Homo Sapien
<220> FEATURE:
<221> NAME/KEY: MISC_FEATURE
<222> LOCATION: (2)..(2)
<223> OTHER INFORMATION: Xaa can be any naturally occuring amino acid
<220> FEATURE:
<221> NAME/KEY: MISC_FEATURE
<222> LOCATION: (3)..(3)
<223> OTHER INFORMATION: Xaa can be Lys or Arg

<400> SEQUENCE: 123

Arg Xaa Xaa Arg
1

<210> SEQ ID NO 124
<211> LENGTH: 4
<212> TYPE: PRT
<213> ORGANISM: Homo Sapien

<400> SEQUENCE: 124

Gly Gly Ser Gly
1
```

METHODS AND COMPOSITIONS FOR PRODUCING A CELL EXPRESSING A T CELL RECEPTOR

CROSS-REFERENCE TO RELATED APPLICATIONS

This application is a national phase entry of PCT/CA2015/000049, filed Jan. 28, 2015, which claims priority from U.S. Provisional patent application Ser. No. 61/933,048 filed Jan. 29, 2014 each of these applications being incorporated herein in their entirety by reference.

INCORPORATION OF SEQUENCE LISTING

A computer readable form of the Sequence Listing "10723-P45386US01_SequenceListing.txt" (61,841 bytes), submitted via EFS-WEB and created on Jul. 7, 2016, is herein incorporated by reference.

TECHNICAL FIELD

The present disclosure relates to methods and compositions for producing a recombinant cell expressing a T cell receptor (TCR) specific for a peptide of interest, methods and compositions for obtaining a nucleic acid or pair of TCR chain polypeptides and/or nucleic acids encoding a TCR, a cell population comprising the recombinant cell harboring the one or more nucleic acids encoding a TCR or TCR chain obtained by said method, and a method for treating a disorder comprising administering to the subject said cell population.

INTRODUCTION

Gene transfer of tumor reactive TCR has been shown to confer both high avidity and tumor reactivity to non-reactive peripheral blood mononuclear cells (PBMCs) and tumor infiltrating lymphocytes (TILs) (Johnson et al. 2006). These authors reported that generating TIL clones directly from melanoma patient tumor digests reveals a diversity of MART-1 reactive T cells with varying cellular avidities and that TCR transfer is sufficient to confer overall cellular avidity to donor PBMCs in an antigen specific manner. Further, nonreactive TIL can be made tumor reactive upon RNA electroporation with a high avidity MART-1 TCR. Recent clinical trials have demonstrated that adoptive transfer of T cells transduced with anti-tumor TCR can induce sustained objective clinical responses in patients with cancer (Kunert A et al., 2013, Hinrichs C S, et al., 2014).

Most of the tumor associated-antigens identified so far are self-antigens. Because of central and peripheral T cell tolerance, a majority of TCRs cloned from peripheral T cells possess low affinity, which is not sufficient to recognize tumor cells expressing self-antigens as tumor-associated antigens. Methods for identifying or generating high affinity TCRs include bacteriophage display mutation and selection technology (Li et al., 2005) and amino acid substitution in TCR CDRs (Robbins et al., 2008). TCR variants identified using these methods can possess affinities that range 1 million fold between the wild-type receptor and that of the tightest binding TCR.

SUMMARY OF THE DISCLOSURE

The present disclosure relates to in an aspect a method for producing a recombinant cell expressing a T cell receptor (TCR) specific for a peptide of interest, which comprises the step of transducing a cell population with a nucleic acid which encodes either one of two polypeptide chains constituting a TCR expressed and previously isolated from a T cell recognizing said peptide of interest, wherein said cell population comprises a cell which is able to express a TCR or differentiate into a cell expressing a TCR. In an embodiment, the method comprises the step of culturing the transduced cell population with an antigen presenting cell presenting the peptide of interest. In another embodiment, the method further comprises the step of selecting a cell expressing a TCR specific for a peptide of interest from the transduced cell population. In yet another embodiment; said cell population is a population of PBMCs or PBMCs activated with a CD3 ligand. In another embodiment, said nucleic acid transduced into said cell population encodes a TCR alpha chain or a TCR beta chain. In yet another embodiment, said nucleic acid transduced into said cell population encodes a TCR chain which predominantly contributes to peptide recognition by a TCR.

An aspect includes a method for generating a high affinity TCR specific for a peptide of interest comprising:
 a) transducing a cell population comprising cells able to express a TCR and/or differentiate into a cell expressing a TCR with a bait nucleic acid encoding a bait TCR polypeptide chain, wherein the bait TCR polypeptide chain can constitute a parent TCR with a counterchain TCR polypeptide chain that specifically binds said peptide of interest; and
 b) culturing under conditions that permit the bait TCR to be expressed.

In an embodiment, the method further comprises selecting a cell expressing a TCR comprising the bait TCR polypeptide chain and a prey TCR polypeptide chain that selectively binds said peptide of interest from the transduced cell population obtained in step (a) or (b).

In another embodiment, the method further comprises isolating a prey nucleic acid encoding the prey TCR polypeptide chain from the selected cell.

Another aspect includes a method for obtaining a TCR polypeptide chain that can form a TCR specific for a peptide of interest comprising:
 a) transducing a cell population comprising cells able to express a TCR and/or differentiate into cells expressing a TCR with a bait nucleic acid encoding a bait TCR polypeptide chain, wherein the bait TCR polypeptide chain can constitute a parent TCR with a counterchain TCR polypeptide chain that specifically binds said peptide of interest;
 b) optionally selecting a cell expressing a TCR comprising the bait TCR polypeptide chain and a prey TCR polypeptide chain that selectively binds said peptide of interest from the transduced cell population obtained in step (a); and
 c) isolating a prey nucleic acid encoding the prey TCR polypeptide chain from the selected cell.

In an embodiment, the bait TCR polypeptide chain is selected from a bait TCRalpha and/or bait TCRbeta polypeptide chain.

In an embodiment, the step of selecting the cell expressing a TCR comprising the bait TCR polypeptide chain and a prey TCR polypeptide chain that selectively binds said peptide of interest from the transduced cell population obtained in step (a) comprises isolating cells that express the transduced bait polypeptide and which bind the peptide of interest.

In an embodiment, the prey nucleic acid is isolated by cloning the prey nucleic acid.

TCRs comprise a CDR1, CDR2 and CDR3 region. In an embodiment, the prey TCR polypeptide CDR3 region comprises at least one amino acid modification relative to the CDR3 region in a control TCR polypeptide CDR3 region, optionally the CDR3 region of the cognate polypeptide chain (e.g. same chain type) in the parent TCR.

In an embodiment, the method is for determining a TCR polypeptide chain that forms a TCR with increased avidity and/or high affinity for a peptide of interest, wherein the method further comprises: i) introducing the isolated prey nucleic acid and the bait nucleic acid into a cell able to express a TCR or differentiate into a cell expressing a TCR; ii) measuring the avidity and/or affinity of the TCR comprising the prey TCR polypeptide chain and the bait TCR polypeptide chain; and iii) isolating a prey nucleic acid clone wherein the bait polypeptide chain and the prey TCR polypeptide chain constitute a TCR having increased avidity and/or affinity for the peptide of interest compared to a control TCR optionally the parent TCR.

In an embodiment, the bait polypeptide, optionally TCRalpha and/or bait TCRbeta polypeptide chain, was expressed in and previously isolated from a T cell recognizing said peptide of interest.

Also provided in another aspect is a method for producing a pair of nucleic acids encoding a TCR specific for a peptide of interest, which comprises the steps of:
  (a) transducing a cell population with a nucleic acid which encodes either one of two polypeptide chains constituting a TCR expressed and previously isolated from a T cell recognizing said peptide of interest, wherein said cell population comprising cells which are able to express a TCR or differentiate into cells expressing a TCR,
  (b) selecting a recombinant cell expressing the TCR specific for a peptide of interest from the transduced cell population obtained in step (a),
  (c) isolating a nucleic acid encoding a polypeptide which constitutes TCR with the polypeptide encoded by the nucleic acid transduced into said cell population from the cell selected in step (b), and
  (d) pairing the nucleic acid transduced into said cell population in step (a) with the nucleic acid isolated in step (c).

Another embodiment, also provides a method for producing a nucleic acid encoding a TCR polypeptide chain which in combination with a counterchain TCR polypeptide constitutes a TCR specific for a peptide of interest, the method comprising the steps of:
  a) transducing a cell population comprising cells which cells can express a TCR or differentiate into cells expressing a TCR with a bait nucleic acid which encodes a TCR polypeptide, optionally selected from a TCRalpha or a TCRbeta polypeptide chain, which in combination with a counterchain TCR polypeptide chain constitutes an expressed TCR, wherein the bait polypeptide was previously isolated from a T cell recognizing said peptide of interest,
  b) selecting a recombinant cell expressing the TCR specific for a peptide of interest from the transduced cell population obtained in step (a), and
  c) isolating a nucleic acid encoding a prey polypeptide which constitutes a TCR with the polypeptide encoded by the bait nucleic acid transduced into said cell population from the cell selected in step (b).

Another embodiment includes a method for producing a recombinant cell expressing a T cell receptor (TCR) specific for a peptide of interest, which comprises the step of transducing a cell population with a nucleic acid which encodes either TCR polypeptide chain (e.g. either TCR alpha or TCR beta or TCR gamma or TCR delta) constituting a TCR expressed and previously isolated from T cell recognizing said peptide of interest, wherein said cell population comprises a cell which is able to express a TCR or differentiate into cells expressing a TCR, and culturing said transduced cell population under conditions that permit the bait TCR polypeptide to be expressed (e.g. and a TCR to be formed).

In an embodiment, step (a) further comprises the step of culturing the transduced cell population with an antigen presenting cell presenting the peptide of interest. In another embodiment, the cell population is a population of peripheral blood mononuclear cells (PBMCs) or PBMCs activated with a CD3 ligand. In an embodiment, the nucleic acid transduced into said cell population in step (a) encodes a TCR alpha chain or a TCR beta chain.

In an embodiment, the method further comprises the step of selecting the cell expressing the TCR specific for a peptide of interest from the transduced cell population.

In an embodiment, said nucleic acid transduced into said cell population encodes a TCR alpha chain or a TCR beta chain.

In an embodiment, said nucleic acid transduced into said cell population encodes a TCR chain which predominantly contributes to peptide recognition by a TCR.

In an embodiment, the transduction is repeated a second, third, fourth, fifth or sixth time.

In an embodiment, the prey TCR can for example be isolated from a T cell, e.g. an endogenously expressed TCR chain.

In an embodiment, the isolated prey nucleic acid encoding the prey TCR polypeptide is transduced into a population of cells comprising a cell which is able to express a TCR or can differentiate into a cell expressing a TCR, optionally wherein the isolated prey nucleic acid is transduced in combination with a nucleic acid encoding a TCR polypeptide chain that in combination with the prey TCR polypeptide chain constitutes a TCR, optionally the bait TCR nucleic acid, to produce a transduced cell population comprising cells expressing a TCR specific for a peptide of interest.

In an embodiment, the cell population is transduced with an antisense molecule for suppressing expression of an endogenous TCR chain.

In an embodiment, the nucleic acid being transduced, optionally the bait nucleic acid, is codon optimized.

Also provided is a recombinant cell comprising a high affinity TCR specific for a peptide of interest, comprising a TCR prey nucleic acid described herein and/or obtained as described herein.

Also provided in another aspect is a cell population comprising a cell expressing a TCR specific for a peptide of interest comprising TCR prey polypeptide or nucleic acid described herein or obtained by a method described herein; optionally a cell population comprising a cell expressing a TCR specific for a peptide of interest which comprises a pair of nucleic acids described herein and/or obtained by a method described herein.

A further aspect includes a method for treating a disorder comprising the step of administering to the subject a therapeutically effective amount of a cell population or recombinant obtained as described herein.

In an embodiment, the method further comprises the step of activating the cell population with a cytokine and/or an antigen peptide prior to the administering step.

Another aspect is a nucleic acid encoding a TCR beta chain having an amino acid sequence represented by SEQ ID NO: 4, 6, 94, 96 or 98.

Yet another aspect is a nucleic acid encoding a TCR alpha chain having an amino acid sequence selected from the group consisting of SEQ ID NOs: 8, 10, 12 and 14.

Also provided in an embodiment, is an isolated and/or recombinantly engineered polypeptide comprising a sequence selected from SEQ ID NO: 4, 6, 8, 10, 12, 14, 52, 54, 56, 58, 60, 62, 81-86, 88-91, 94, 96, 98, 112, 114, 116-122 and/or a sequence having at least 85%, at least 90%, at least 95%, at least 96%, at least 97%, at least 98% or at least 99% sequence identity to a sequence selected from to a sequence selected from SEQ ID NOs: 4, 6, 8, 10, 12, 14, 52, 54, 56, 58, 60, 62, 81-86, 88-91, 94, 96, 98, 112, 114, 116-122 or a portion thereof such as a CDR region or a non-CDR region. In an embodiment the polypeptide comprises a sequence of any one of SEQ ID NOs:4, 6, 8, 10, 12, 14, 52, 54, 56, 58, 60, 62, 81-86, 88-91, 94, 96, 98, 112, 114, 116-122.

In an embodiment, the isolated and/or recombinantly engineered polypeptide is encoded by any one of SEQ ID NOs: 3, 5, 7, 9, 11, 13, 51, 53, 55, 57, 59, 61, 93, 95, 97, 111, 113, 115 and/or a nucleic acid sequence having at least 85%, at least 90%, at least 95%, at least 96%, at least 97%, at least 98% or at least 99% sequence identity to a sequence selected from to a sequence selected from SEQ ID NOs: 3, 5, 7, 9, 11, 13, 51, 53, 55, 57, 59, 61, 93, 95, 97, 111, 113, 115 and for example encoding a polypeptide selected from 4, 6, 8, 10, 12, 14, 52, 54, 56, 58, 60, 62, 81-91, 112, 114 and 116-122 or a portion thereof such as a CDR region or a non-CDR region.

In an embodiment, the isolated and/or recombinantly engineered nucleic acid comprises a sequence as shown in any one of SEQ ID NOs: 3, 5, 7, 9, 11, 13, 51, 53, 55, 57, 59, 61, 93, 95, 97, 111, 113 and 115.

Also provided in an embodiment, is an isolated and/or recombinantly engineered nucleic acid encoding a TCR chain comprising a CDR3 region amino acid sequence selected from SEQ ID NO: 52, 54, 56, 58, 60 62, 81 to 91, 112, 114 and 116-122.

In an embodiment, the isolated and/or recombinantly engineered nucleic acid described herein wherein the TCR beta chain comprises an amino acid sequence represented by SEQ ID NO: 4, 6, 94, 96 or 98.

Also provided in an embodiment is an isolated and/or recombinantly engineered TCRbeta chain wherein the CDR3 region comprises any one of SEQ ID NOs: 52, 54, 81 to 91, 112, 114, and 116 to 122.

Another embodiment includes an isolated TCRalpha chain wherein the CDR3 region comprises any one of SEQ ID NO: 56, 58, 60 and 62.

Another aspect includes an isolated and/or recombinantly engineered nucleic acid encoding a TCR alpha chain comprising a CDR3 region amino acid sequence selected from the group consisting of SEQ ID NOs: 56, 58, 60 and 62.

In an embodiment, the isolated and/or recombinantly engineered nucleic acid encodes a TCR alpha chain comprising an amino acid sequence selected from the group consisting of SEQ ID NO: 8, 10, 12 and 14.

Another embodiment includes an isolated and/or recombinantly engineered TCR comprising a TCRalpha chain and a TCRbeta chain wherein the TCRbeta chain comprises a CDR3 region comprising the sequence of any one of SEQ ID NO: 52, 54, 81 to 91, 112, 114 and 116 to 122 and/or the TCR alpha chain a CDR3 region comprising the sequence of any one of SEQ ID NO: 56, 58, 60 and 62.

Another embodiment includes an isolated and/or recombinantly engineered cell comprising the isolated nucleic acid and/or polypeptide described herein, the TCRbeta chain described herein the TCRalpha chain described herein, and/or the TCR described herein.

Another aspect includes a nucleic acid, polypeptide composition, optionally a pharmaceutical composition, recombinant cell or cell population comprising a prey nucleic acid or prey polypeptide described herein and/or produced using a method described herein for treating a disorder.

A further aspect includes a use of a nucleic acid, composition and/or cell population producing using a method described herein for treating a disorder.

and one A24− (bottom left) donors following 2 stimulations with A24-aAPC cells loaded with WT1$_{235-243}$ heteroclitic peptide is shown. IFN-γ ELISPOT using 2.0×10$^4$ CD8+ gene-modified T cells following 2 stimulations was performed in the presence or absence of indicated aAPC cells as target cells. ELISPOT assay was carried out in triplicate. These TAK1β-transduced CD8+ T cells derived from one A24+ (top right) and one A24− (bottom right) donors following 2 stimulations both produced IFN-γ against A24-aAPC cells that naturally processed and presented A24/WT1 on the cell surface. A24-aAPC cells loaded with 1 µg/mL HIV-1 env584-592 peptide or 1 µg/mL WT1235-243 heteroclitic peptide were used as negative and positive controls for WT1235-243 peptide specificity. All of experiments were carried out in triplicate and error bars show SD.

FIG. 10 is a bar chart showing a repertoire of TCRα clonotypes which can recognize A24/WT1 when paired with TAK1β. The Variable region and J region of a TCRα clonotype was denoted by IMGT nomenclature. The result is an aggregate of 3 HLA-A24+ and 1 HLA-A24− donors and 41 different TCRα clonotypes are shown. The J region (A) and the length of CDR3α amino acid sequences (B) in each TRAVs are summarized by stacked bar graph.

Figure 11:
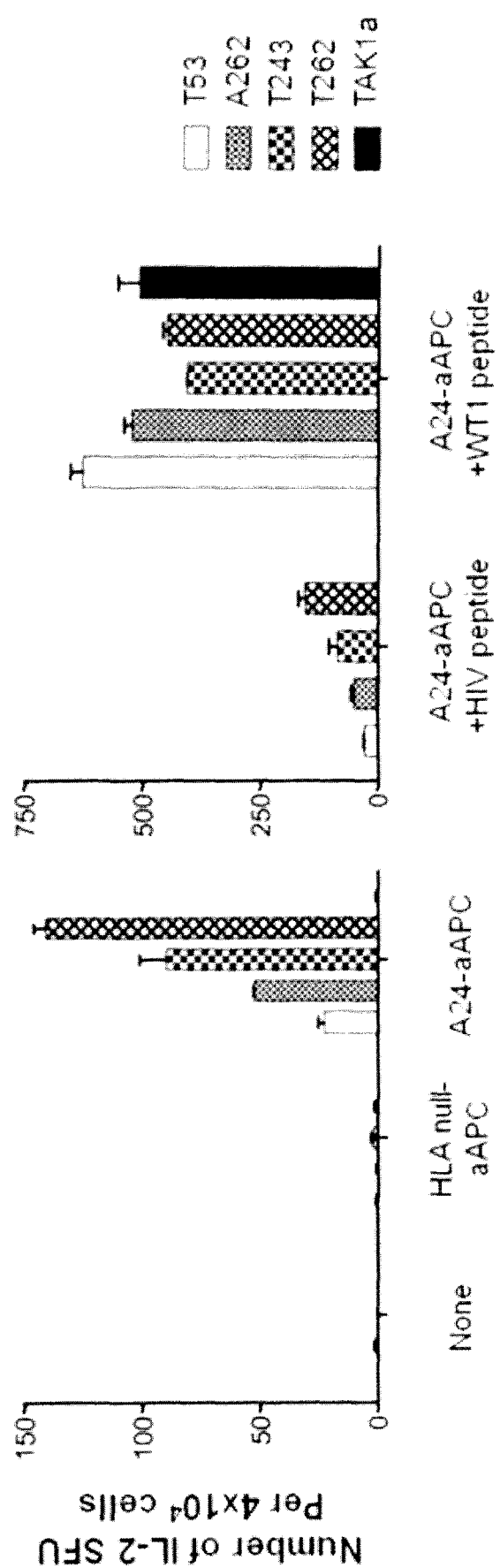

FIG. 11 is an ELISPOT assay showing that novel TCRα/TAK1β TCRs recognize WT1-derived peptide endogenously processed and presented by A24 with different avidity. Jurkat76 cells, which lack the expression of CD8αβ and intrinsic TCR, were retrovirally transduced with CD8αβ and TAK1β gene. Following transduction of these genes, Jurkat76/CD8αβ/TAK1β transfectant was additionally transduced with TCRα gene (clone: T53, A262, T243, T262) or parent TAK1α gene. All transfectants were >95% positive for CD3. IL-2 ELISPOT was done by incubating 4.0×104 Jurkat76/CD8αβ/TAK1β/TCRα cells in the presence or absence of aAPC cells. Jurkat76 transfectants (clone: T53, A262, T243, T262) produced IL-2 against A24-aAPC cells that naturally processed and presented A24/WT1 on the cell surface (left). A24-aAPC cells loaded with 1 µg/mL HIV-1 env584-592 peptide or WT1$_{235-243}$ heteroclitic peptide were used as negative and positive controls for WT1$_{235-243}$ peptide specificity (right). All of experiments were carried out in triplicate and error bars show SD.

FIG. 12 shows the sequences of nucleotide (top, SEQ ID NO: 1) and amino acid (bottom, SEQ ID NO: 2) of clone SIG35α TCR alpha chain. The CDR1, CDR2 and CDR 3 nucleotide and amino acid sequences of the cloned SIG35α alpha chain are represented by SEQ ID NOs: 17, 33, 49, 18, 34 and 50, respectively.

FIG. 13 shows the sequences of nucleotide (top, SEQ ID NO: 3) and amino acid (bottom, SEQ ID NO: 4) of clone 794 TCR beta chain. The CDR regions of the nucleotide and the amino acid are underlined. The CDR1, CDR2 and CDR 3 nucleotide and amino acid sequences of the cloned 794 TCR beta chain are represented by SEQ ID NOs: 19, 35, 51, 20, 36 and 52, respectively.

FIG. 14 shows the sequences of nucleotide (top, SEQ ID NO: 5) and amino acid (bottom, SEQ ID NO: 6) of clone 830 TCR beta chain. The CDR regions of the nucleotide and the amino acid are underlined. The CDR1, CDR2 and CDR3 nucleotide and amino acid sequences of the cloned 830 TCR beta chain are represented by SEQ ID NOs: 21, 37, 53, 22, 38 and 54, respectively.

FIG. 15 shows the sequences of nucleotide (top, SEQ ID NO: 7) and amino acid (bottom, SEQ ID NO: 8) of clone T53 TCR alpha chain. The CDR regions of the nucleotide and the amino acid are underlined. The CDR1, CDR2 and CDR 3 nucleotide and amino acid sequences of the cloned T53 TCR alpha chain are represented by SEQ ID NOs: 23, 39, 55, 24, 40 and 56, respectively.

FIG. 16 shows the sequences of nucleotide (top, SEQ ID NO: 9) and amino acid (bottom, SEQ ID NO: 10) of clone A262 TCR alpha chain. The CDR regions of the nucleotide and the amino acid are underlined. The CDR1, CDR2 and CDR 3 nucleotide and amino acid sequences of the cloned A262 TCR alpha chain are represented by SEQ ID NOs: 25, 41, 57, 26, 42 and 58, respectively.

FIG. 17 shows the sequences of nucleotide (top, SEQ ID NO: 11) and amino acid (bottom, SEQ ID NO: 12) of clone T243 TCR alpha chain. The CDR regions of the nucleotide and the amino acid are underlined. The CDR1, CDR2 and CDR 3 nucleotide and amino acid sequences of the cloned T243 TCR alpha chain are represented by SEQ ID NOs: 27, 43, 59, 28, 44 and 60, respectively.

FIG. 18 shows the sequences of nucleotide (top, SEQ ID NO: 13) and amino acid (bottom, SEQ ID NO: 14) of clone T262 TCR alpha chain. The CDR regions of the nucleotide and the amino acid are underlined. The CDR1, CDR2 and CDR 3 nucleotide and amino acid sequences of the cloned T262 TCR alpha chain are represented by SEQ ID NOs: 29, 45, 61, 30, 46 and 62, respectively.

FIG. 19 shows the sequences of nucleotide (top, SEQ ID NO: 15) and amino acid (bottom, SEQ ID NO: 16) of clone TAK1 TCR beta chain. The CDR1, CDR2 and CDR 3 nucleotide and amino acid sequences of the cloned TAK1 TCR beta chain are represented by SEQ ID NOs: 31, 47, 63, 32, 48 and 64, respectively.

Figures 20, 21:
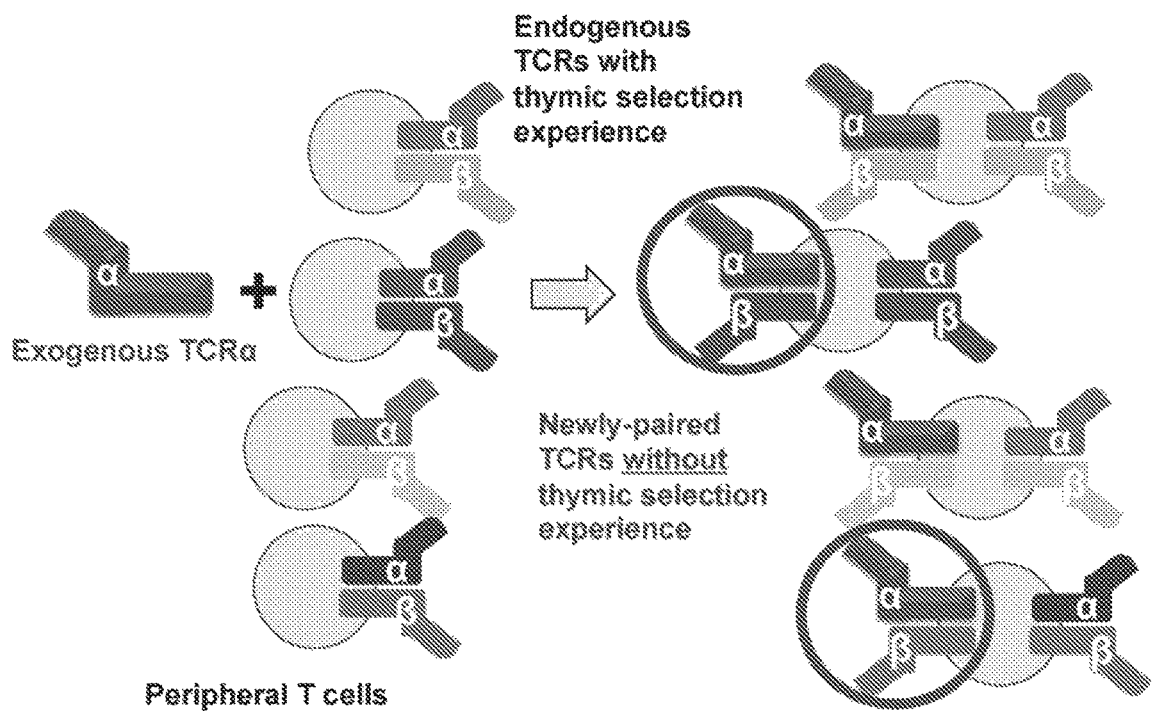

FIG. 20 illustrates that de novo TCRs generated by TCR single chain transduction are unselected by Thymus.

FIG. 21 is a schematic of a bait TCR construct.

FIG. 22 is a chart describing anti-tumor TCR gene therapy.

Figure 23:
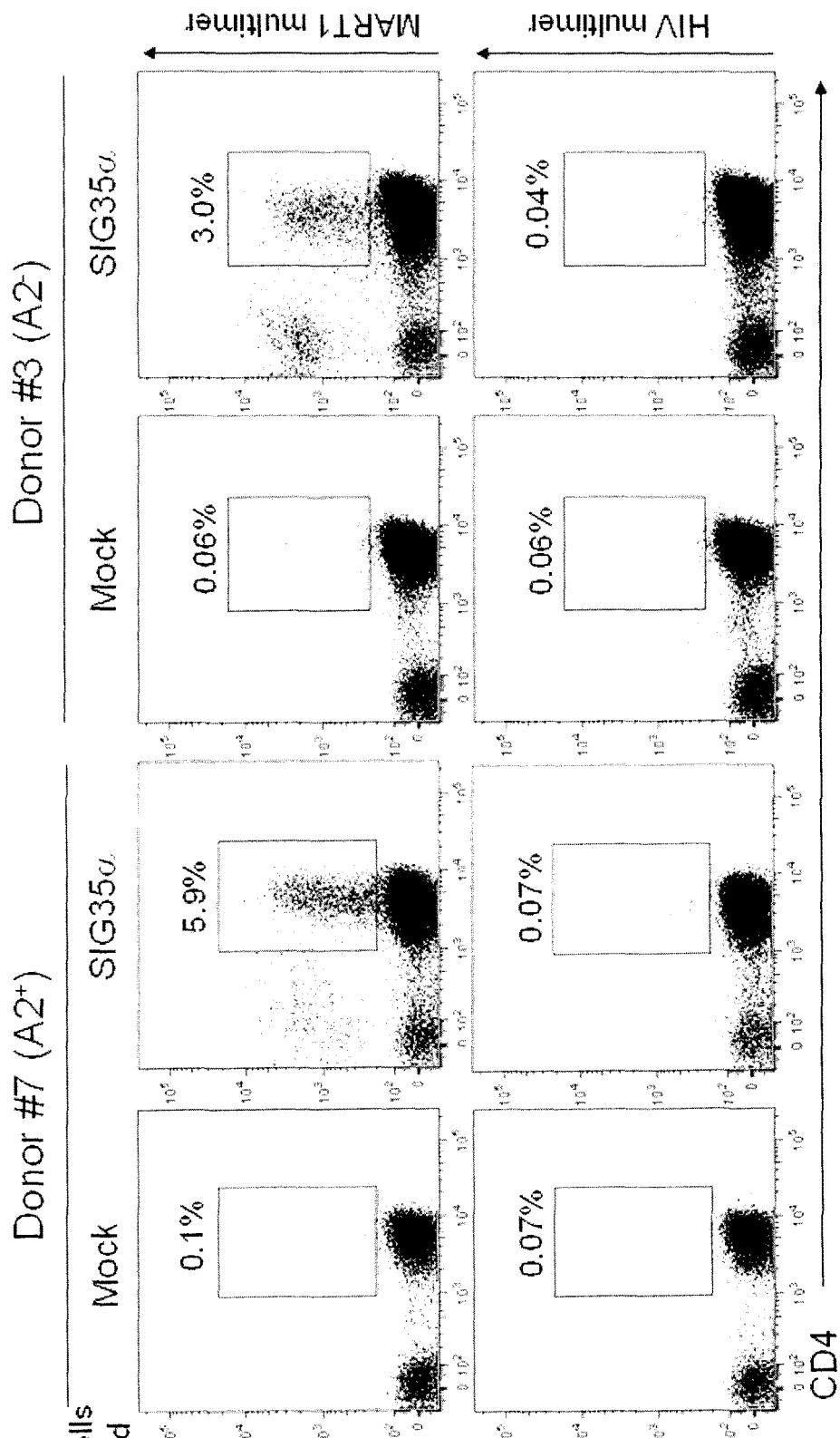

FIG. 23 is a flow cytometric analysis showing that both HLA-A2+ and A2− peripheral CD4+ T cells can recognize A2/MART1 when transduced with chain-centric SIG35α. Both HLA-A2+ and A2− peripheral CD4+ T cells become A2/MART1-reactive upon transduction of chain-centric SIG35α. Peripheral CD4+ T cells freshly isolated from one HLA-A2+ donors #7 and one A2− donors #3 and were retrovirally transduced with SIG35α or Mock. The transfectants were stimulated with IL-21-secreting mutA2-aAPC pulsed with 10 µg/ml MART1$_{27-35}$ peptide once a week. Between stimulations, IL-2 (10 IU/ml) and IL-15 (10 ng/ml) were added every 3 days. Data for A2/MART1 or A2/HIV multimer staining conducted after second stimulation are shown.

Figure 24:
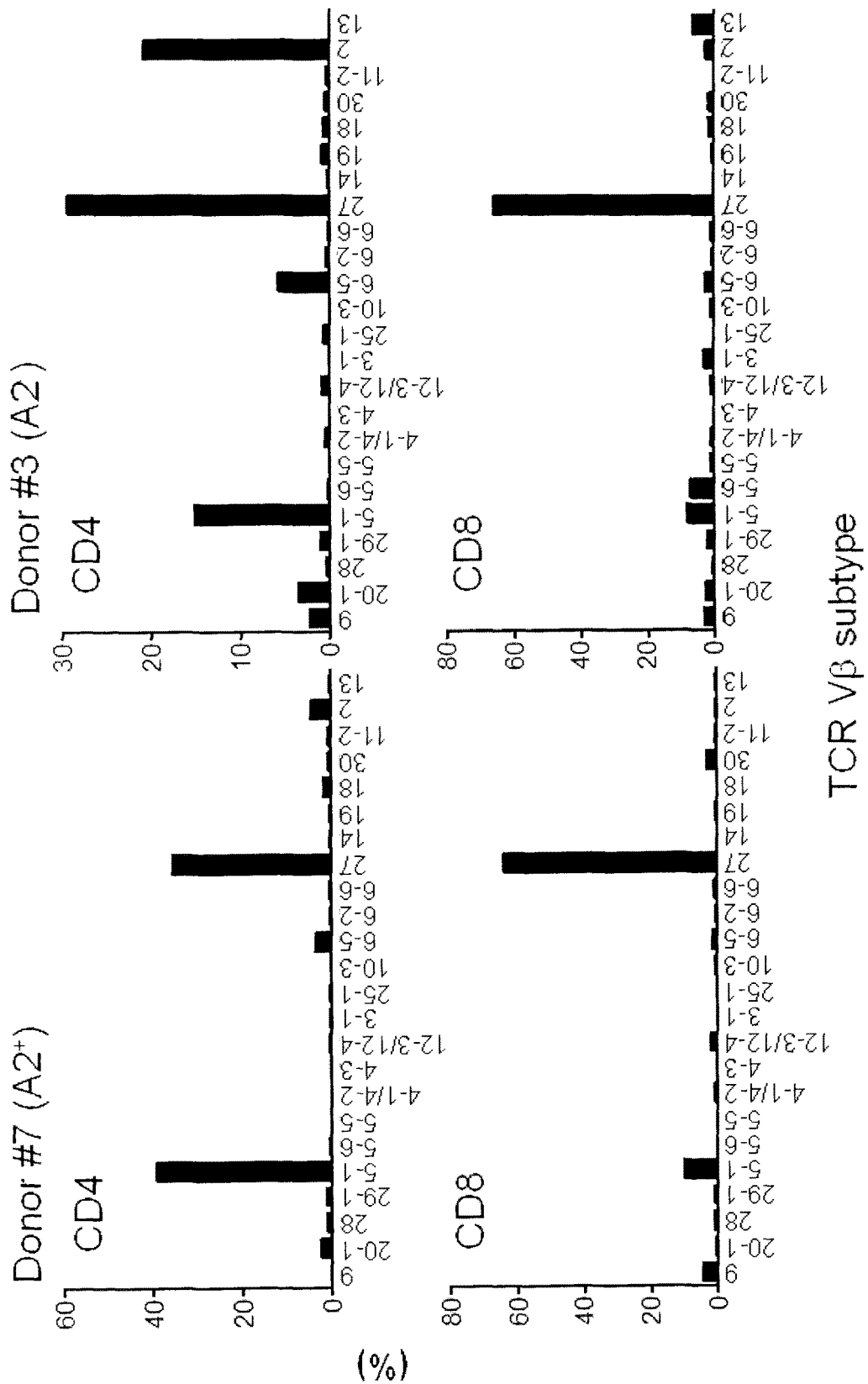

FIG. 24 is a bar chart demonstrating that SIG35α predominantly selects with TRBV5-1, 27 and 2 in CD4+ T cells to recognize A2/MART1. SIG35α-transduced CD4+ T cells and CD8+ T cells after second stimulation with mutA2-aAPC in an A2+ or an A2− donor were co-stained with A2/MART1 multimer, monoclonal antibodies (mAbs) for TCR Vβ subtypes and α-human CD4 mAb or α-human CD8 mAb. The percentage of A2/MART1 multimer+ CD4+ T cells or A2/MART1 multimer+ CD8+ T cells expressing each subtype is shown.

Figure 25:
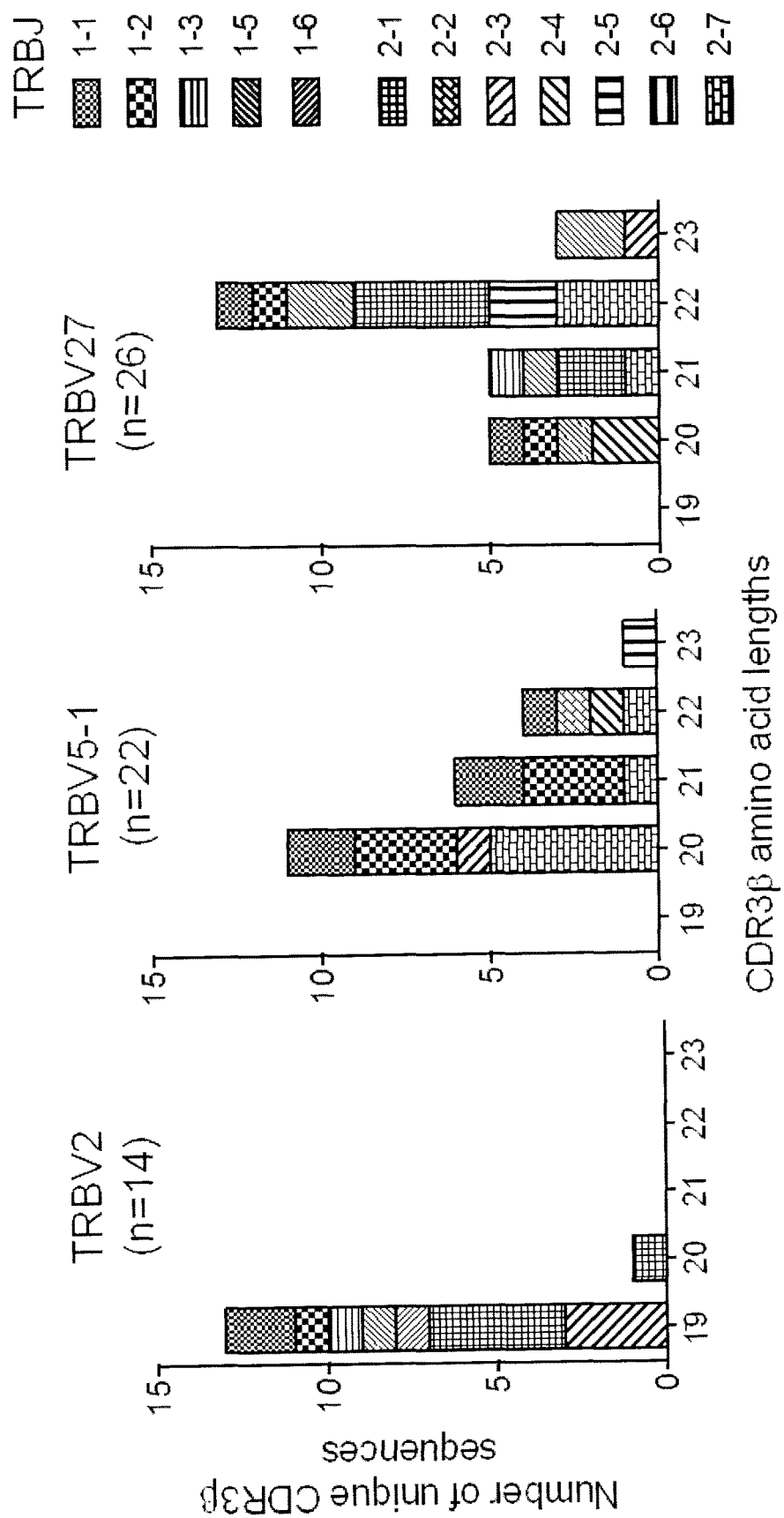

FIG. 25 is a bar chart demonstrating that TRBV2, 5-1 and 27 clonotypes that can compose A2/MART1 TCRs in conjunction with SIG35α are highly heterogeneous and unique. SIG35α-transduced CD4+ T cells in an A2+ or A2− donor were stimulated with 10 µg/ml MART1$_{27-35}$ peptide-pulsed mutA2-aAPC. A2/MART1 multimer+ CD4+ T cells were collected by flow cytometry cell sorting. TRBV2, 5-1 and 27 TCRβ chains isolated from the A2/MART1 multimer+ T cells were sequenced. Jβ gene segments and CDR3 lengths of isolated each TRBV chain are shown.

Figure 26:
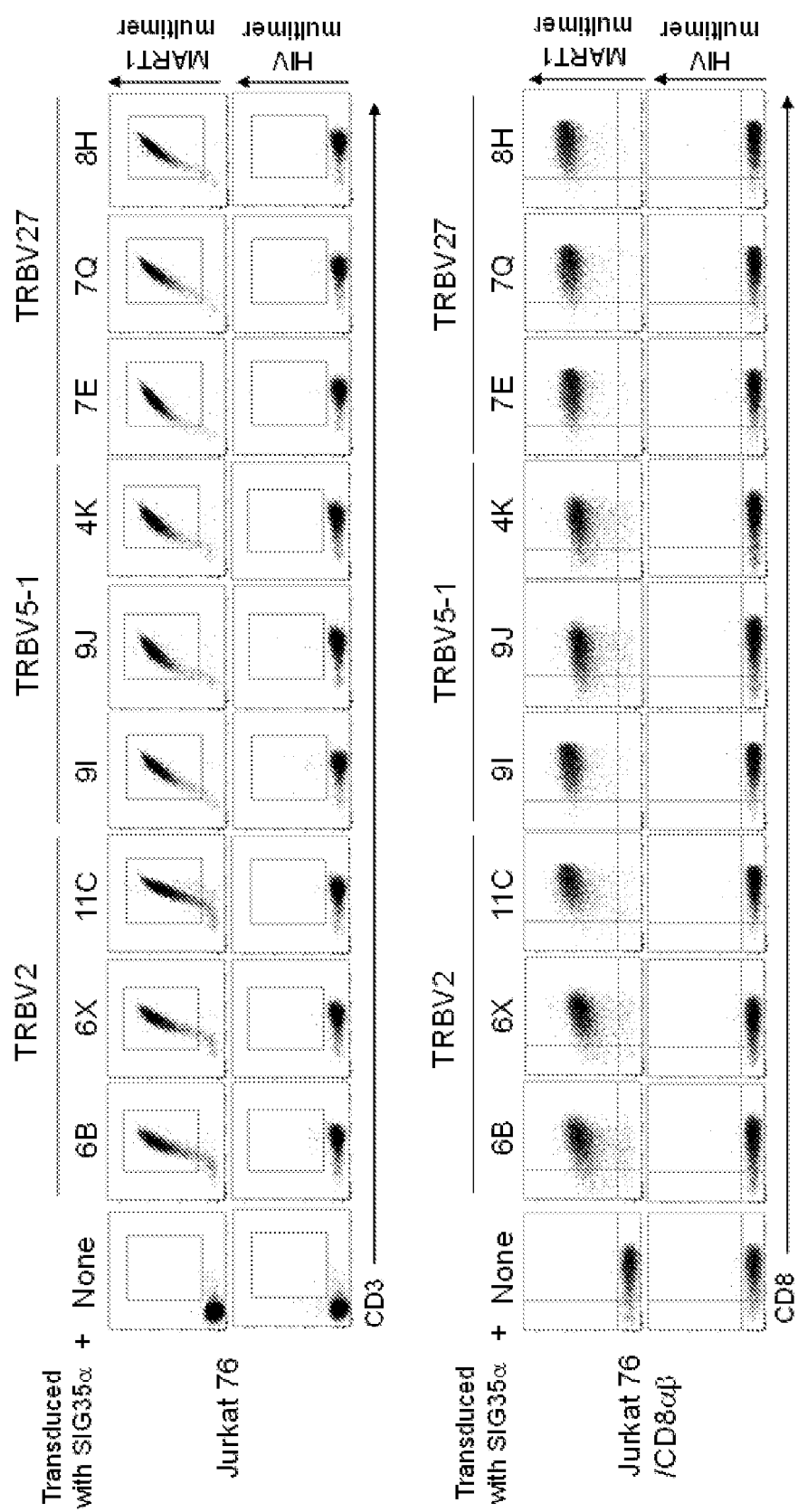

FIG. 26 is a flow cytometric analysis demonstrating that reconstituted CD4+ A2/MART1 TCRs recognize A2/MART1 in a CD8-independent manner. Jurkat 76 cells, which lack the expression of CD8αβ and endogenous TCRs, were retrovirally transduced with CD8αβ to produce Jurkat 76/CD8αβ. Jurkat 76 or Jurkat 76/CD8αβ cells were individually transduced with TRBV2, 5-1, or 27 TCRβ chains (clone: 6B, 6X, 11C, 9I, 9J, 4K, 7E, 7Q, or 8H), which was isolated from CD4+ A2/MART1 T cells, along with SIG35α chain. All Jurkat 76 or Jurkat 76/CD8αβ transfectants were stained with 2 µg/ml A2/MART1 or A2/HIV multimer along with anti-CD3 mAb or anti-CD8 mAb. Data for multimer staining of Jurkat 76 (top) or Jurkat 76/CD8αβ transfectants (bottom) are shown.

Figure 27:
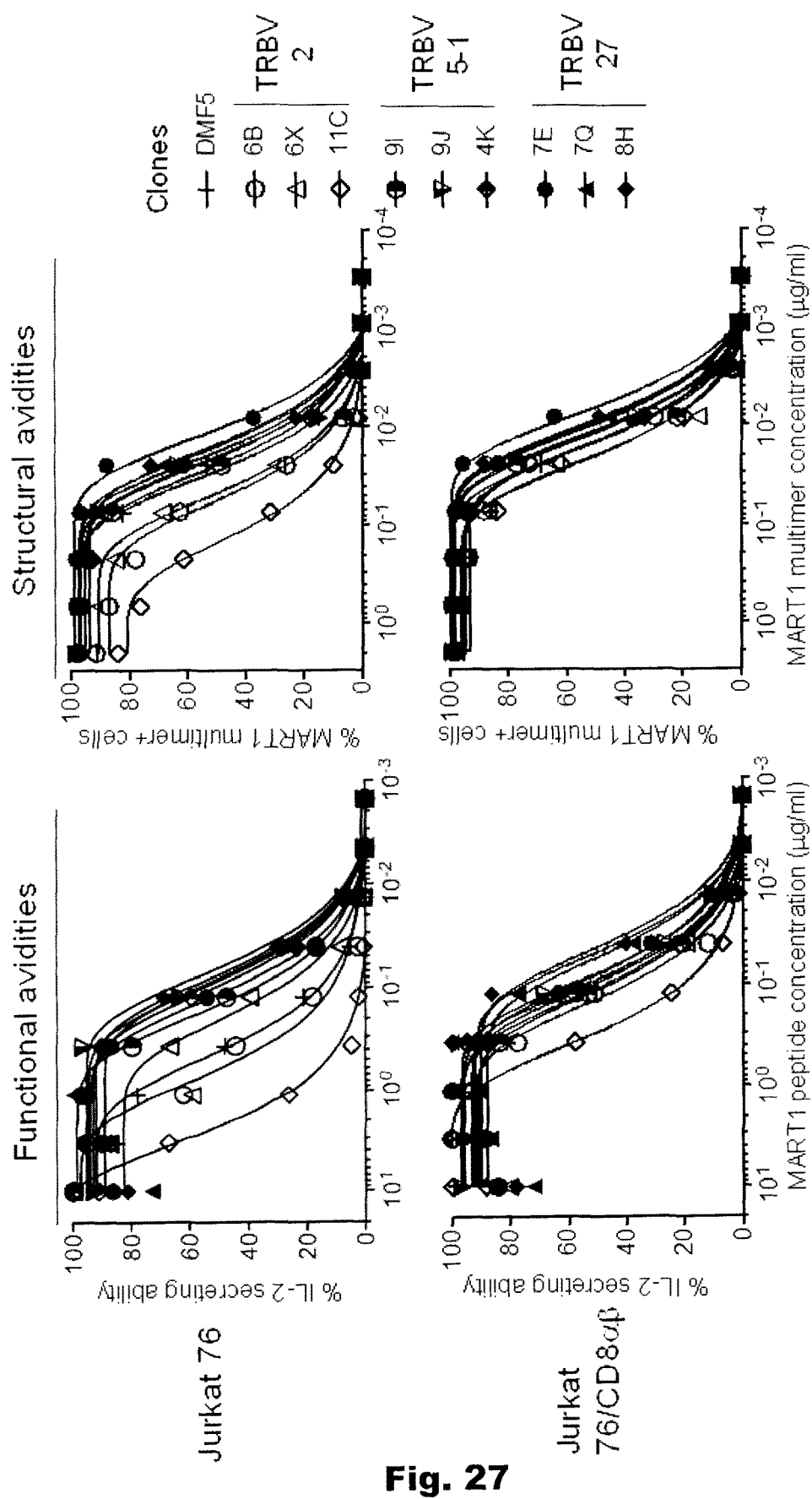

FIG. 27 is a series of charts demonstrating that reconstituted CD4+ A2/MART1 TCRs possess a broad range of functional and structural avidities. Functional avidities of Jurkat 76 or Jurkat 76/CD8αβ cells expressing 9 different A2/MART1 TCRβ chains paired with SIG35α and DMF5 are depicted as % IL-2 secreting abilities determined by IL-2 ELISPOT assays using T2 cells pulsed with graded concentrations of $MART1_{27-35}$ peptide as stimulator cells (left). Structural avidities of the same transfectants are shown as multimer staining percentages determined by staining with graded concentrations of A2/MART1 multimer (right).

FIG. 28 shows the sequences of nucleotide (top, SEQ ID NO: 93) and amino acid (bottom, SEQ ID NO: 94) of clone 8H TCR beta chain. The CDR regions of the nucleotide and the amino acid are underlined. The CDR1, CDR2 and CDR 3 nucleotide and amino acid sequences of the cloned 8H TCR beta chain are represented by SEQ ID NOs: 99, 105, 111, 100, 106 and 114, respectively.

FIG. 29 shows the sequences of nucleotide (top, SEQ ID NO: 95) and amino acid (bottom, SEQ ID NO: 96) of clone 7Q TCR beta chain. The CDR regions of the nucleotide and the amino acid are underlined. The CDR1, CDR2 and CDR 3 nucleotide and amino acid sequences of the cloned 7Q TCR beta chain are represented by SEQ ID NOs: 101, 107, 113, 102, 108 and 114, respectively.

FIG. 30 shows the sequences of nucleotide (top, SEQ ID NO: 97) and amino acid (bottom, SEQ ID NO: 98) of clone 9J TCR beta chain. The CDR regions of the nucleotide and the amino acid are underlined. The CDR1, CDR2 and CDR 3 nucleotide and amino acid sequences of the cloned 9J TCR beta chain are represented by SEQ ID NOs: 103, 109, 115, 104, 110 and 116, respectively.

DETAILED DESCRIPTION

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies. In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps. The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. The term "about" means plus or minus 0.1 to 50%, 5-50%, or 10-40%, preferably 10-20%, more preferably 10% or 15%, of the number to which reference is being made. Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

(1) Methods for Identifying a TCR Polypeptide Chain that can Constitute a TCR Specific for a Peptide of Interest and for Producing One or More Nucleic Acids Encoding a TCR Specific for a Peptide of Interest An aspect includes a method for generating a high affinity TCR specific for a peptide of interest comprising:
  a) transducing a cell population comprising cells able to express a TCR and/or differentiate into a cell expressing a TCR with a bait nucleic acid encoding a bait TCR polypeptide chain, wherein the bait TCR polypeptide chain can constitute a parent TCR with a counterchain TCR polypeptide chain that specifically binds said peptide of interest; and
  b) culturing under conditions that permit the bait TCR to be expressed.

In an embodiment, the method further comprises selecting a cell expressing a TCR comprising the bait TCR polypeptide chain and a prey TCR polypeptide chain that selectively binds said peptide of interest from the transduced cell population obtained in step (a) or (b).

In another embodiment, the method further comprises isolating a prey nucleic acid encoding the prey TCR polypeptide chain from the selected cell.

In another aspect, the disclosure includes a method for identifying and/or obtaining a TCR polypeptide chain that can constitute a TCR specific for a peptide of interest or a cell comprising said TCR polypeptide further comprising:
  c) obtaining a recombinant cell expressing a TCR comprising the bait TCR polypeptide chain and a prey TCR polypeptide chain that selectively binds said peptide of interest from the transduced cell population obtained in step (a) or (b); and
  d) isolating a prey nucleic acid encoding the prey TCR polypeptide chain from the selected cell.

In another embodiment, the method further comprises step e) pairing the isolated prey nucleic acid isolated with the bait nucleic acid which when expressed provide a high affinity TCR.

As used herein, the term "TCR" refers to a molecule comprising a single fused TCR (e.g. fusing the TCR chains comprising the variable regions (CDR1/2/3) of TCRalpha and TCRbeta chains or the variable regions of TCRdelta and TCRgamma chains), including TCRalpha:TCRbeta, TCRbeta:TCRalpha, TCRdelta:TCRgamma and TCRgamma:TCRdelta fusions) and/or complex minimally comprising two molecules each comprising a TCR chain, each TCR chain minimally comprising a variable region, wherein each TCR chain is the counterchain of the other (e.g. TCRalpha and TCRbeta chains or TCRgamma and TCRdelta chains). As used herein "TCR" can refer to nucleic acid molecules that can encode the TCR polypeptide chains, e.g. TCR alpha and beta chain polypeptides, or single fused TCR and/or the TCR polypeptide chains e.g. TCR alpha and beta chain comprising polypeptides, fused or separate.

As used herein, the term "TCR chain" refers to 1) a nucleic acid encoding a TCR chain polypeptide and/or encoding a functional fragment thereof and/or 2) a TCR chain polypeptide and/or functional fragment thereof, selected for example from TCRα, TCRβ, TCRdelta and TCRgamma which can with a counterchain TCR chain constitute a TCR, the functional fragment minimally comprising CDR1, CDR2 and CDR3 regions. The TCR can comprise one or more mammalian, optionally human TCR chains, and/or hybrid TCR chains, for example a mouse:human hybrid chain, optionally wherein the TCR chain comprises human CDR1, CDR2 and CDR3 region and a mouse constant region and/or mouse CDR1, CDR2 and CDR3 regions and a human TCR constant region. A hybrid TCR comprising mouse CDR1/2/3 regions and a human constant region has been reported (Parkhurst et al. 2009, Theoret et al. 2008).

Peptides, typically about 9 amino acids long, are recognized by TCRs in the context of presentation by a human leukocyte antigen (HLA) (which is the human version of the major histocompatibility complex (MHC) (e.g. in a HLA:peptide complex). Some peptides are promiscuous and can be presented by more than one HLA type. Antigen presenting cells (APCs) (both authentic and artificial) present for example a peptide of interest to an effector cell, such as a T cell comprising a TCR that recognizes the peptide of interest, in the context of a HLA molecule. Artificial APCs (aAPCs) which can be used in methods for identifying a counterchain TCR, can express a single allele of HLA. For example as shown herein, aAPC used in the experiments described below comprise HLA-A2 for the MART1 peptide of interest and HLA-A24 for the WT1 peptide of interest.

The term "functional fragment thereof" in reference to a TCR chain means a molecule at least comprising a variable CDR3 region, optionally comprising CDR1, CDR2 and CDR3 regions that together can function to confer peptide of interest specificity. The functional fragment optionally comprises the extracellular portion (EC portion), optionally in combination with the membrane spanning portion of the TCR chain (e.g. intracellular portion is deleted). The functional fragment can for example be comprised in an agent such as a therapeutic agent. For example, the EC portion, optionally in combination with the membrane spanning portion of each TCR counterchain (e.g. TCRalpha and TCRbeta), can be fused to make a single chain TCR fusion which is then conjugated to an effector such as an antibody, optionally comprising a cytotoxic moiety. A TCR effector conjugate can be administered to a subject in need thereof.

In an embodiment, the bait TCR polypeptide chain is selected from a bait TCRalpha or bait TCRbeta polypeptide chain.

In another embodiment, the bait TCR polypeptide chain is selected from a bait TCRgamma or bait TCRdelta polypeptide chain.

The term "bait nucleic acid" as used herein means a nucleic acid encoding a TCR polypeptide chain—optionally alpha or beta, or delta or gamma—that has, in an embodiment, been previously isolated (e.g. identified and cloned) and/or for which the sequence of the CDR regions (e.g. CDR1, CDR2 and CDR3) have been previously determined. For example, for TCR chains wherein the sequence of the CDR regions have been determined, the bait nucleic acid can be cloned and/or constructed, optionally by combining recombinantly produced CDR region nucleic acids with a known constant region, and/or replacing CDR regions in a known TCR chain (e.g. known sequence).

The term "prey nucleic acid" as used herein means a nucleic acid that encodes a prey TCR polypeptide chain, optionally a TCRalpha or TCRbeta polypeptide chain, that can constitute a TCR with the bait TCR polypeptide chain, and is in some embodiments advantageously one that encodes a TCR polypeptide chain that in combination with a second TCR polypeptide chain optionally the bait TCR polypeptide chain, constitutes a TCR which has increased or decreased avidity and/or affinity for the peptide of interest, compared to a control TCR such as a parent TCR.

The transduced bait nucleic acid is expressed in the transduced or recombinant cell as a bait polypeptide TCR chain and pairs with a prey polypeptide TCR chain to make a TCR. Prey nucleic acids encoding the prey TCR polypeptide chains that in combination with the bait TCR polypeptide chain constitute a TCR that can recognize the peptide of interest (in the context of an HLA/peptide complex) can be selected e.g. they can be isolated for example in the context of the cell and/or the prey nucleic acid cloned.

The term "nucleic acid" as used herein refers to a sequence of nucleotide or nucleoside monomers consisting of naturally occurring bases, sugars, and intersugar (backbone) linkages, and includes single-stranded and double-stranded molecules, RNA and DNA, optionally wherein the DNA is non-naturally occurring cDNA, optionally codon optimized DNA. The term also includes modified or substituted oligomers comprising non-naturally occurring monomers or portions thereof, which function similarly. Such modified or substituted nucleic acids may be preferred over naturally occurring forms because of properties such as enhanced cellular uptake or increased stability in the presence of nucleases. The term also includes chimeric nucleic acids that contain two or more chemically distinct regions. For example, chimeric nucleic acids may contain at least one region of modified nucleotides that confer beneficial properties (e.g., increased nuclease resistance, increased uptake into cells), or two or more nucleic acids of the disclosure may be joined to form a chimeric nucleic acid.

The term "isolated nucleic acid" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived.

The isolated and/or recombinant nucleic acids and/or polypeptides can comprise one or more conservative substitutions.

The term "conservative substitutions" as used herein include nucleotide substitutions that do not result in changes in the amino acid sequence, as well as nucleotide substitutions that result in conservative amino acid substitutions, or amino acid substitutions which do not substantially affect the character of the polypeptide translated from said nucleotides.

Conservative substitutions of amino acid sequences include amino acid substitutions or deletions that do not substantially affect the character of the variant polypeptide relative to the starting peptide. For example, polypeptide character is not substantially affected if the substitutions or deletions do not preclude specific binding of the variant peptide to a specific binding partner of the starting peptide. Included in this definition are glycosylated and other variants and derivatives that will be apparent to those skilled in the art and are considered to fall within the scope of this invention. Also included in this definition are amino acid insertions, substitutions, deletions and truncations that do not substantially affect the polypeptide character relative to the starting peptide.

In an embodiment, the substitution includes a molecule in the following list:

Alanine A D-Ala, Gly, beta-Ala, L-Cys, D-Cys
Arginine R D-Arg, Lys, D-Lys, homo-Arg, D-homo-Arg, Met, Ile, D-Met, D-Ile, Orn, D-Orn
Asparagine N D-Asn, Asp, D-Asp, Glu, D-Glu, Gln, D-Gln
Aspartic Acid D D-Asp, D-Asn, Asn, Glu, D-Glu, Gln, D-Gln
Cysteine C D-Cys, S-Me-Cys, Met, D-Met, Thr, D-Thr
Glutamine Q D-Gln, Asn, D-Asn, Glu, D-Glu, Asp, D-Asp
Glutamic E D-Glu, D-Asp, Asp, Asn, D-Asn, Gln, Acid D-Gln
Glycine G Ala, D-Ala, Pro, D-Pro, β-Ala Asp
Isoleucine I D-Ile, Val, D-Val, Leu, D-Leu, Met D-Met
Leucine L D-Leu, Val, D-Val, Leu, D-Leu, Met, D-Met
Lysine K D-Lys, Arg, D-Arg, homo-Arg, D-homo-Arg, Met, D-Met, Ile, D-Ile, Orn, D-Orn
Methionine M D-Met, S-Me-Cys, Ile, D-Ile, Leu, D-Leu, Val, D-Val
Phenylalanine F D-Phe, Tyr, D-Thr, L-Dopa, His, D-His, Trp, D-Trp, Trans-3,4, or 5-phenylproline, cis-3,4, or 5-phenylproline
Proline P D-Pro, L-I-thioazolidine-4-carboxylic acid, D- or L-1 oxazolidine-4-carboxylic acid
Serine S D-Ser, Thr, D-Thr, allo-Thr, Met, D-Met, Met (O), D-Met(O), L-Cys, D-Cys
Threonine T D-Thr, Ser, D-Ser, allo-Thr, Met, D-Met, Met(O), D-Met(O), Val, D-Val
Tyrosine Y D-Tyr, Phe, D-Phe, L-Dopa, His, D-His
Valine V D-Val, Leu, D-I,eu Ile, D-Ile, Met, D-Met In an embodiment the following substitutions can be made: S and T; I, V, and L; and/or F and Y.

In an embodiment, the conservative substitution is selected from the following six groups which each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The step of obtaining the recombinant cell expressing a TCR comprising the bait TCR polypeptide chain and a prey TCR polypeptide chain that selectively binds said peptide of interest from the transduced cell population can comprise isolating one or more cells (e.g. one or more clones) that express the transduced bait polypeptide and which bind the peptide of interest.

As used herein "counterchain TCR chain" relates to a TCR chain that can associate with a stipulated TCR chain type to constitute a TCR. For example, in the context of a bait TCRalpha chain, the counterchain prey TCR chain would be a prey TCRbeta chain and vice versa. Similarly, in the context of a bait TCRgamma chain, the counterchain prey TCR chain would be a prey TCRdelta chain and vice versa.

In an embodiment, the obtaining step comprises removing non-transduced cells, cloning the prey nucleic acid, for example into a vector, and determining the avidity and/or affinity of reconstituted TCRs comprising the bait and prey nucleic acids for the peptide of interest. The avidity and/or affinity can be relative, such as relative to other cloned nucleic acids and/or a control or be absolute. For example, prey nucleic acids that in combination with a bait nucleic acid (or other same type TCR chain) constitute a TCR with a desired or preselected affinity/avidity can be isolated. For example the prey nucleic acid can be amplified and/or the previously selected clone can be replicated, using a method appropriate for the type of vector employed.

Alternatively, the recombinant cell expressing the prey nucleic acid can be propagated, and/or packaged.

In an embodiment, the prey nucleic acid is isolated, for example by cloning. The method of cloning the prey nucleic acid is not particularly limited and can comprise determining the TCR Vbeta repertoire of the selected cell and amplifying the prey nucleic acid to make a cDNA using a primer that is specific for the identified TCR Vbeta chain and a TCR beta constant region primer, as further described below. If the prey nucleic acid is a TCRalpha chain, the TCR Valpha repertoire of the selected cell can be determined as above. In addition, 5'RACE based methods can be employed. In an embodiment, two constant region reverse primers are used as described in the examples to enhance the specificity of PCR and specifically clone TCR genes.

Figure 1:
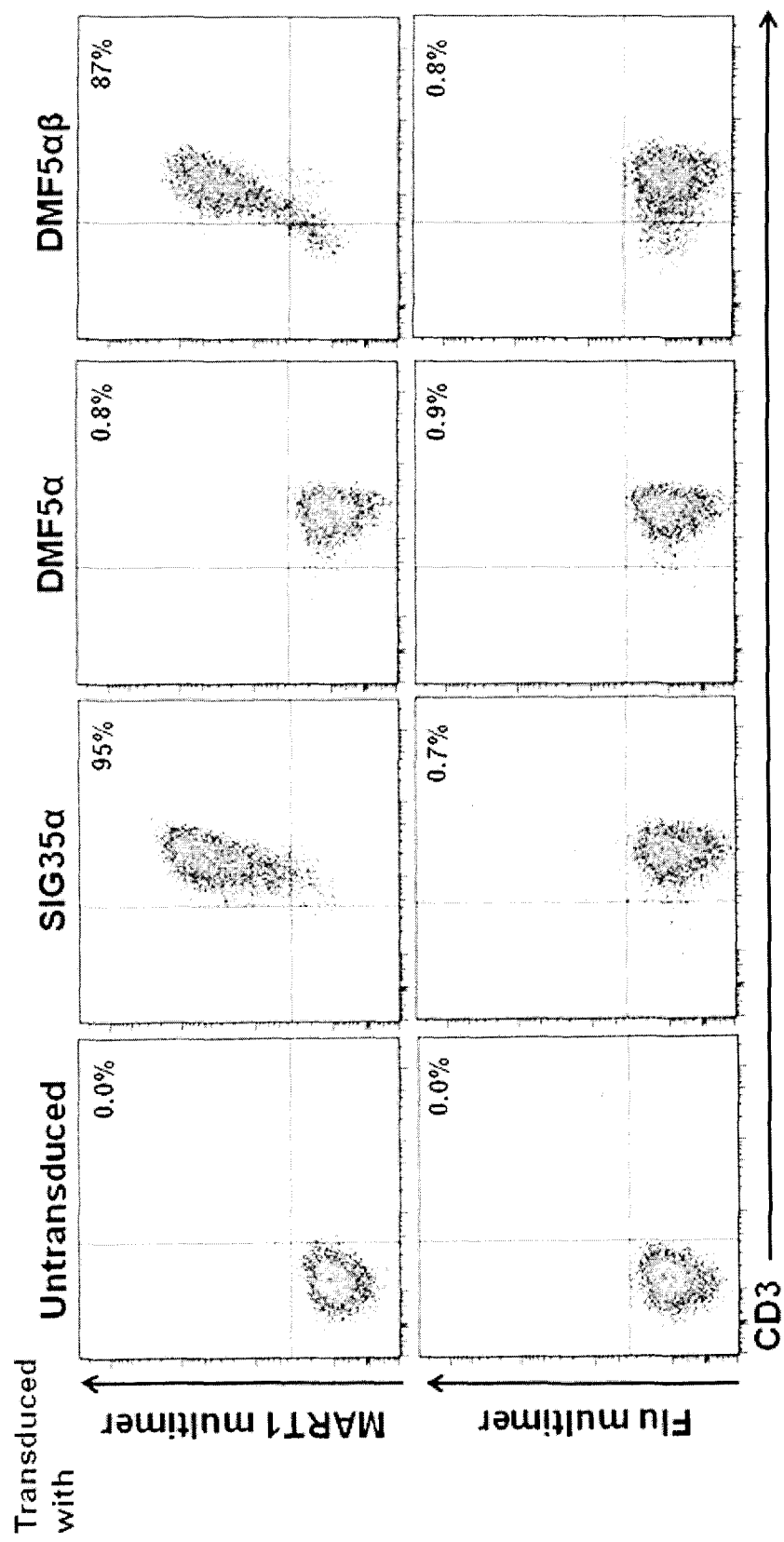
FIG. 1 is a flow cytometric analysis demonstrating that when paired with SupT1 TCRβ, SIG35α but not DMF5α recognizes A2/MART1. SupT1 cells, a TCRα-deficient human T cell line, were transduced with SIG35α, DMF5α, and DMF5αβ. Transfectants were stained with A2/MART1 or A2/Flu multimer and with α-human CD3 mAb.
Figure 2:
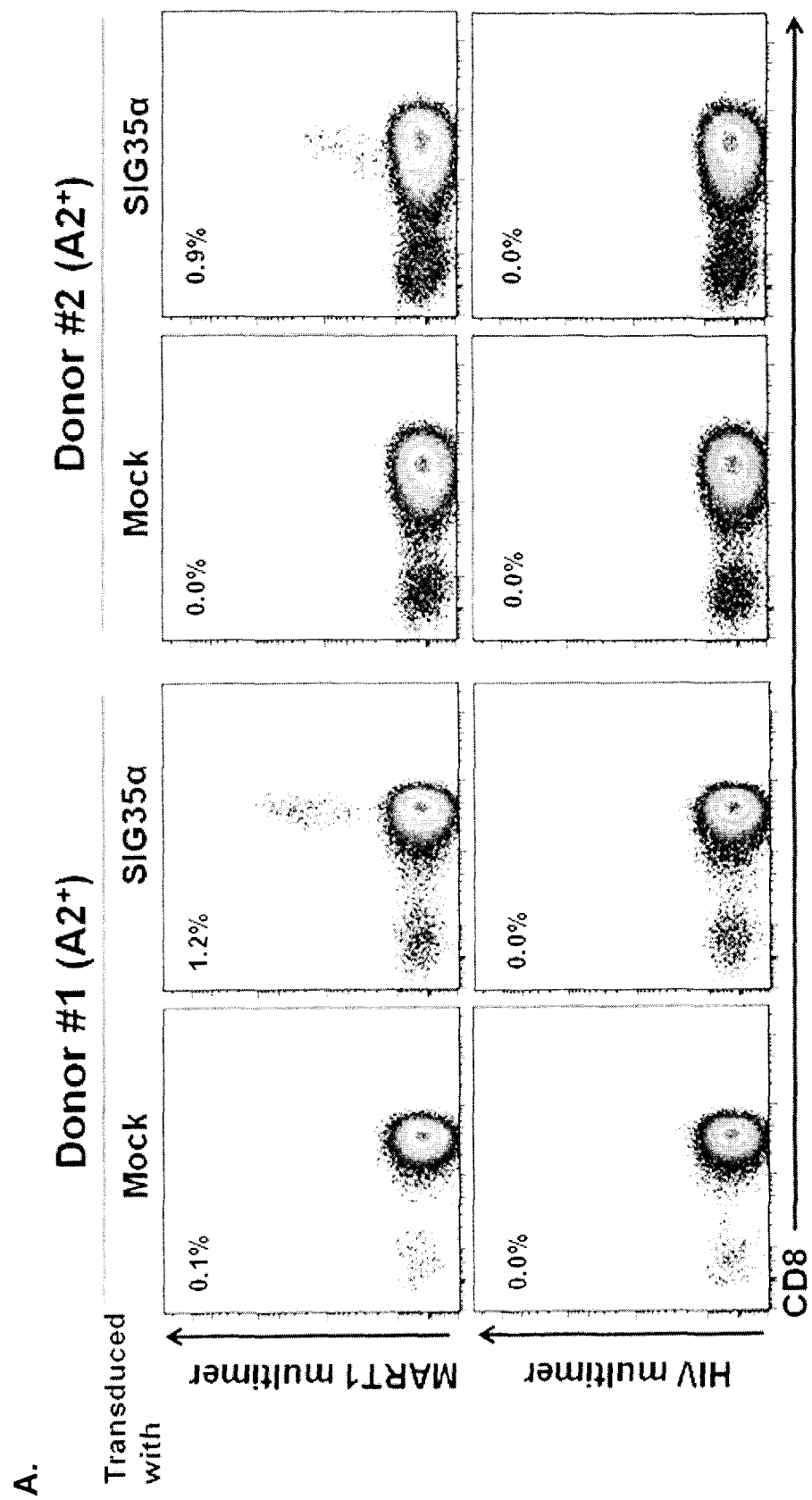
FIG. 2 is a flow cytometric analysis and ELISPOT assay demonstrating that thymic selection does not appear to affect TCR6 repertoire that can constitute A2/MART1 TCR with SIG35α. A) Peripheral T cells freshly isolated from 2 HLA-A2+ donors and 2 A2− donors were stimulated with 50 ng/mL α-human CD3 mAb (OKT3) in the presence of 100 IU/mL IL-2 and retrovirally transduced with truncated NGFR (ΔNGFR) gene (Mock), SIG35α/ΔNGFR gene. SIG35α and ΔNGFR gene was intervened by furin, sgsg and F2A sequence derived from foot and mouth disease virus. After 6 times of transduction, 2.0×105 transfectants were stained with 8 μg/mL A2/MART1 multimer or A2/HIV multimer in conjunction with α-human CD8 mAb and α-human NGFR mAb. ΔNGFR-positive cells were gated and multimer/CD8 positivity was analyzed; B) SIG35α-transduced A2+ peripheral CD8+ T cells recognize A2/MART1. HLA-A2+ peripheral CD8+ T cells were transduced with SIG35α or Mock. Before aAPC stimulation, A2/MART1 specificity was analyzed by multimer staining using A2/MART1 and A2/HIV multimer. A2/HIV multimer was used as a negative control. SIG35α-transduced A2− peripheral CD8+ T cells recognize A2/MART1. HLA-A2− peripheral CD8+ T cells were transduced with SIG35α or Mock. Before aAPC stimulation, A2/MART1 specificity was analyzed by multimer staining using A2/MART1 and A2/HIV multimer. A2/HIV multimer was used as a negative control; C) SIG35α-transduced peripheral T cells are highly avid for A2/MART1 recognition. SIG35α or Mock-transduced CD8+ T cells derived from an A2+ or A2− donor were subjected to IFN-γ ELISPOT analysis. SIG35α or Mock-transduced CD8+ T cells after first stimulation with 10 μg/mL MART1$_{27-35}$ peptide-pulsed wtA2-aAPC were used as responder cells. T2 cells pulsed with 10 μg/mL MART1$_{27-35}$ peptide or HIV pol476-484 peptide were used as stimulator cells (left). HIV pol476-484 peptide was used as a negative control peptide. The A2+/MART1+ melanoma line, Malme-3M and the A2+/MART1− melanoma line, A375 were used as stimulator cells (right). All of experiments were carried out in triplicate and error bars show SD; D) SIG35α-transduced A2/MART1 CD8+ T cells expand upon wtA2-aAPC-based stimulation. SIG35α-transduced CD8+ T cells in an A2+ or A2− donor were stimulated with 10 μg/mL MART1$_{27-35}$ peptide-pulsed wtA2-aAPC once a week. Between stimulations, T cells were supplemented with IL-2 (10 IU/mL) and IL-15 (10 ng/mL) every 3 days. A2/MART1 multimer staining done after 1st and 2nd stimulation is shown; E) SIG35α-transduced A2/MART1 CD8+ T cells expand upon mutA2-aAPC-based stimulation. SIG35α-transduced CD8+ T cells in an A2+ or A2− donor were stimulated with 10 μg/mL MART1$_{27-35}$ peptide-pulsed IL-21-secreting mutA2-aAPC once a week. Between stimulations, T cells were supplemented with IL-2 (10 IU/mL) and IL-15 (10 ng/mL) every 3 days. A2/MART1 multimer staining done after second and third stimulation is shown.
Figure 2:
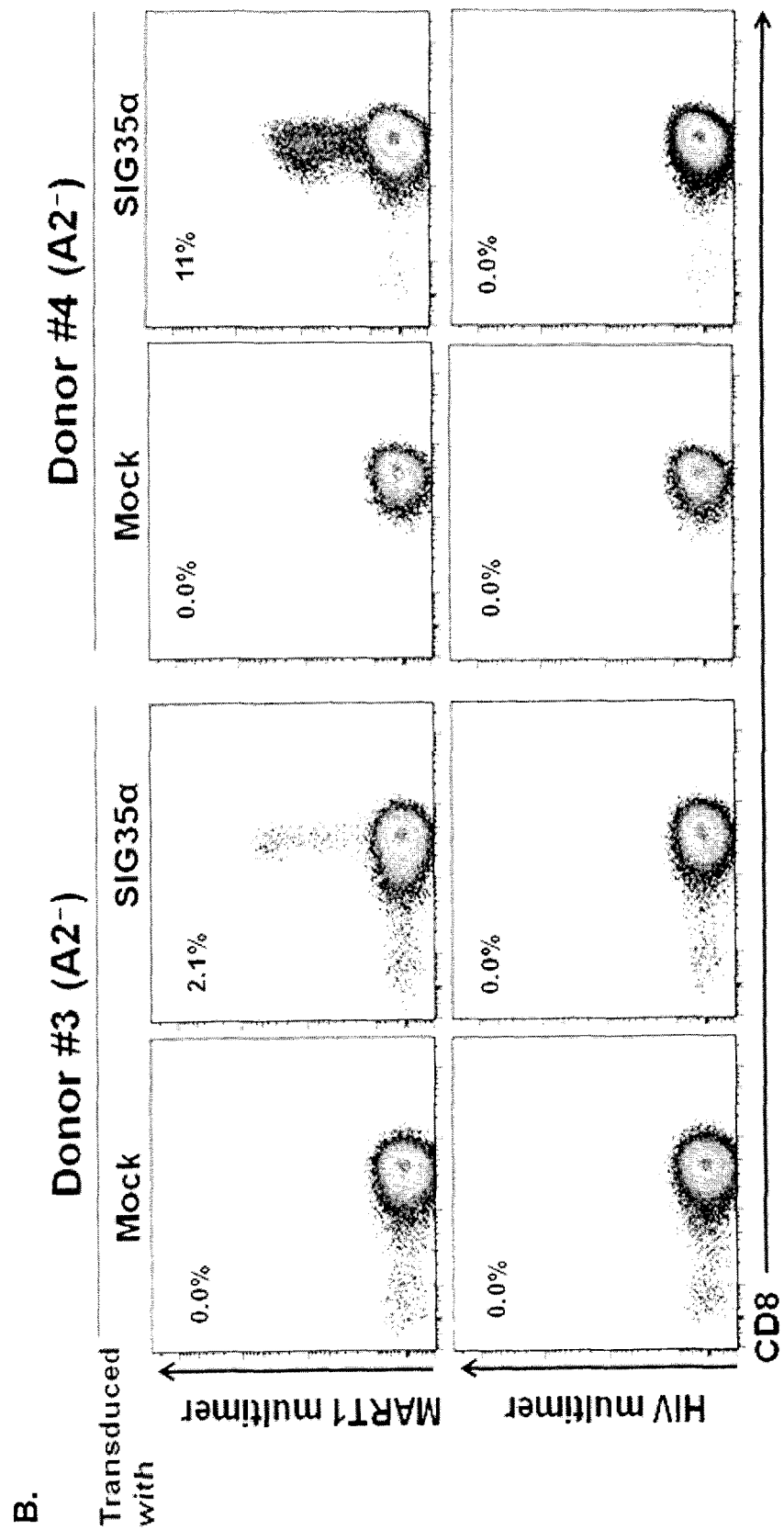
Figure 2:
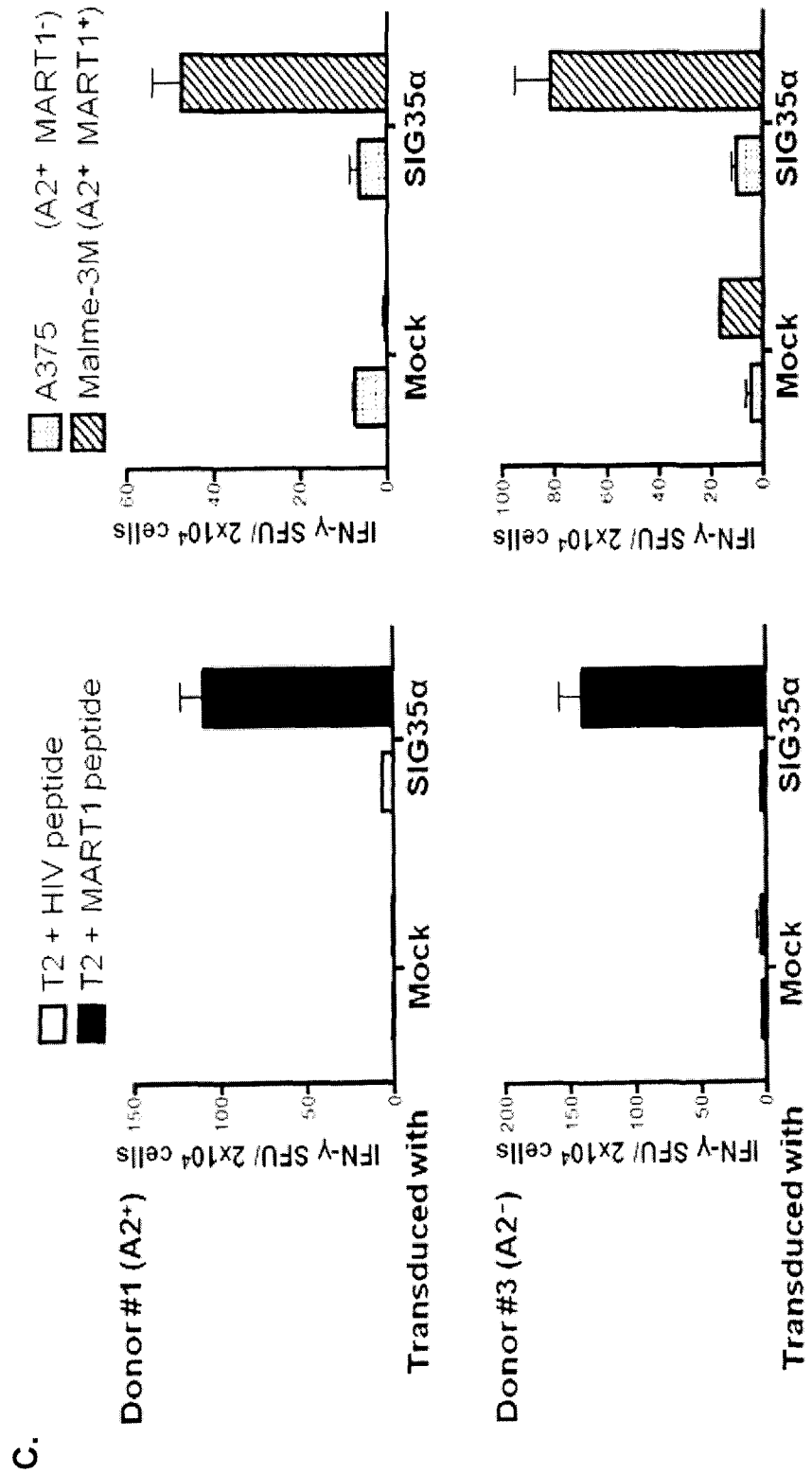
Figure 2:
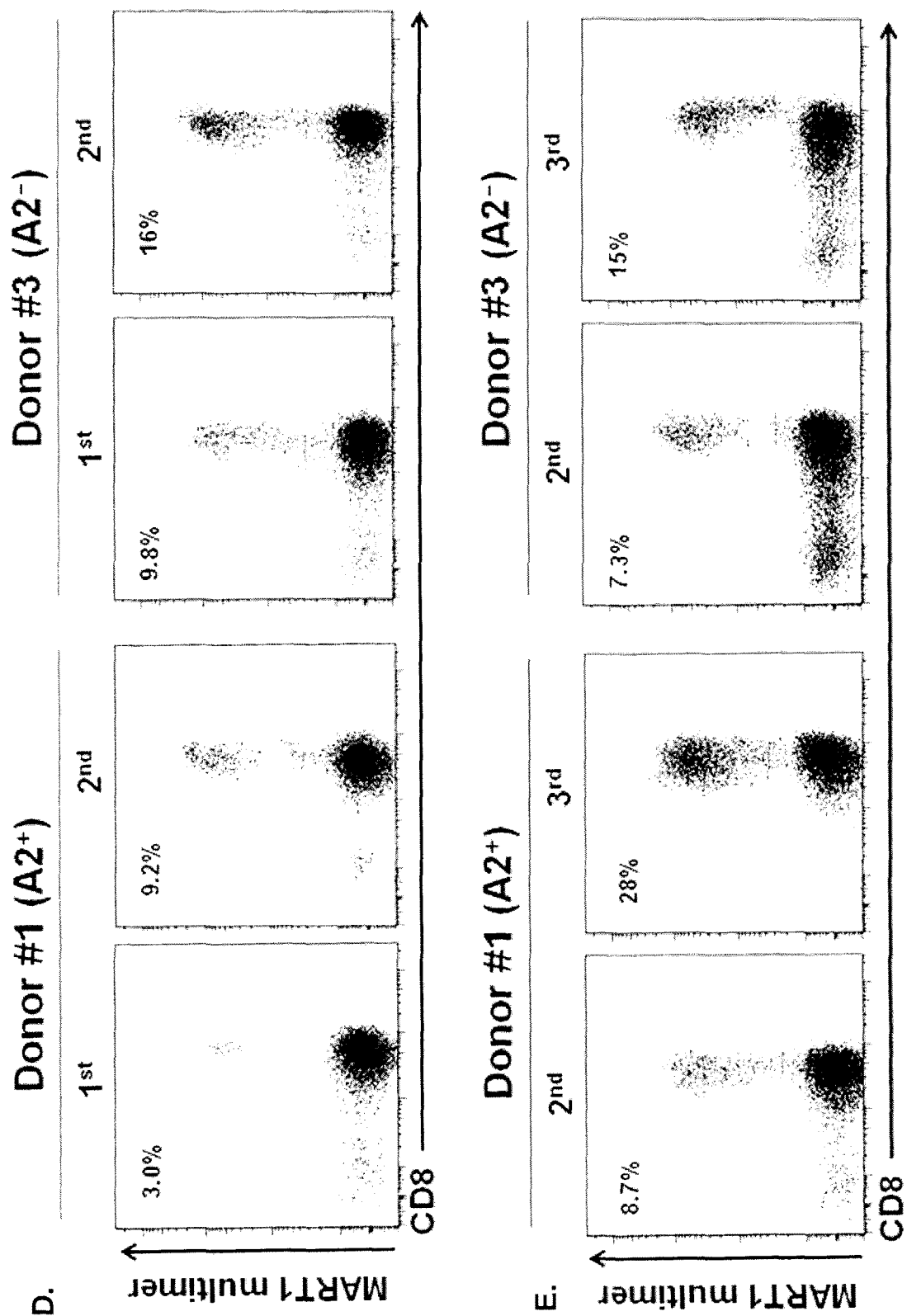
Figure 3:
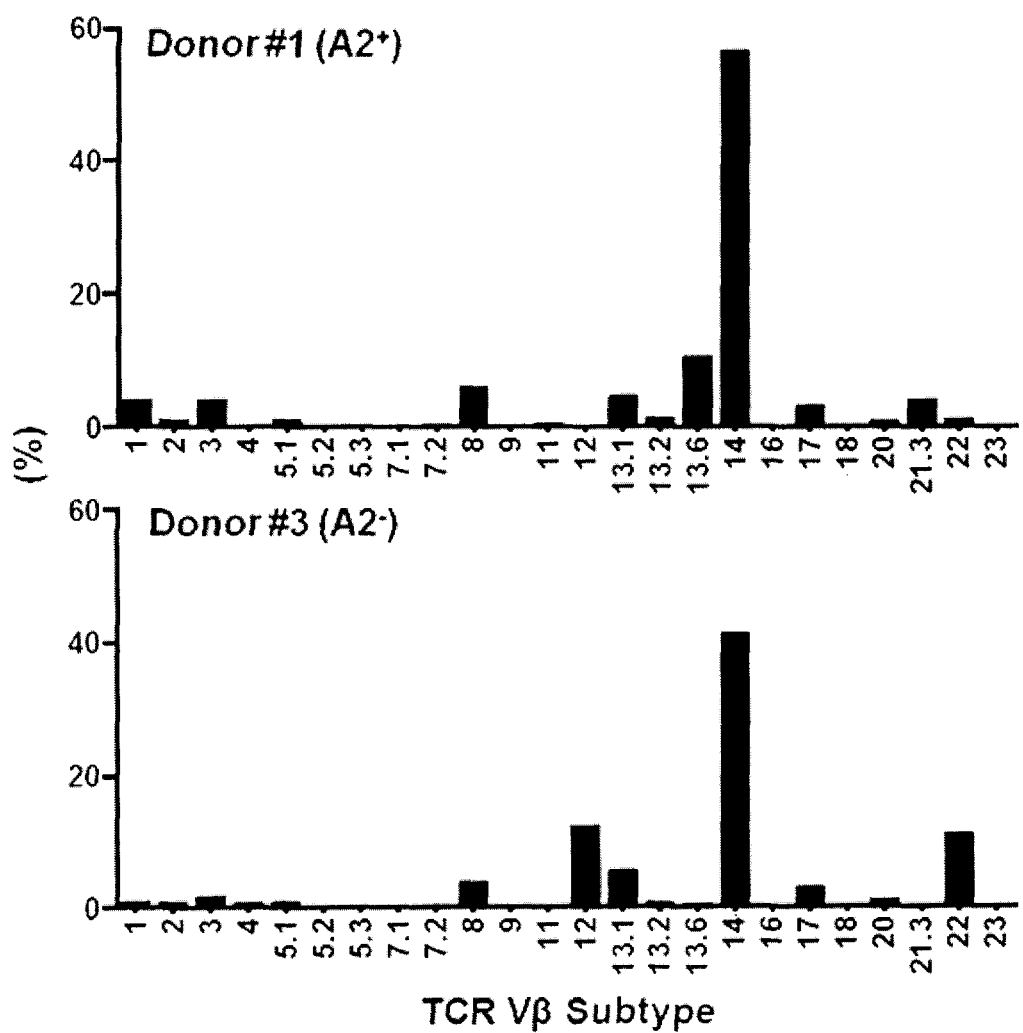
FIG. 3 is a bar chart and flow cytometric analysis demonstrating that SIG35α predominantly pairs with TCR Vβ14 to recognize A2/MART1. A) SIG35α-transduced CD8+ T cells before aAPC stimulation in an A2+ or A2− donor were co-stained with A2/MART1 multimer, monoclonal antibodies (mAbs) for TCR Vβ subtypes and α-human CD8 mAb. SIG35α predominantly pairs with TCR Vβ14 to recognize A2/MART1 in both A2+ and A2− donors. The percentage of A2/MART1 multimer+ CD8+ T cells expressing each subtype is shown. B) "Many" TCR Vβ14 clonotypes can recognize A2/MART1 when paired with SIG35α. The percentage of A2/MART1 multimer+ cells in CD8+ Vβ14+ T cells transduced with SIG35α is shown. The nomenclature used is the one from Wei et al., 1994.
Figure 3:
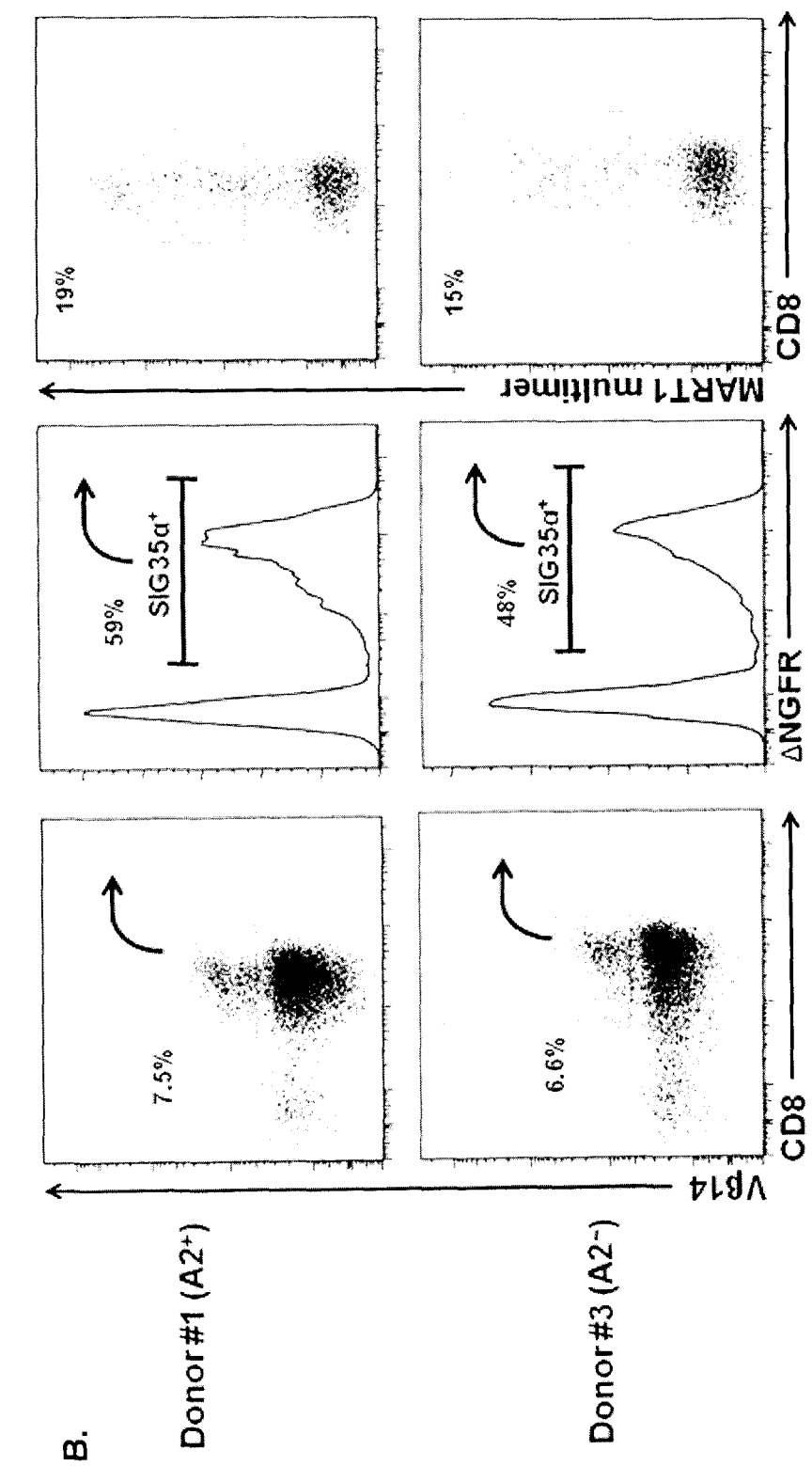
Figure 4:
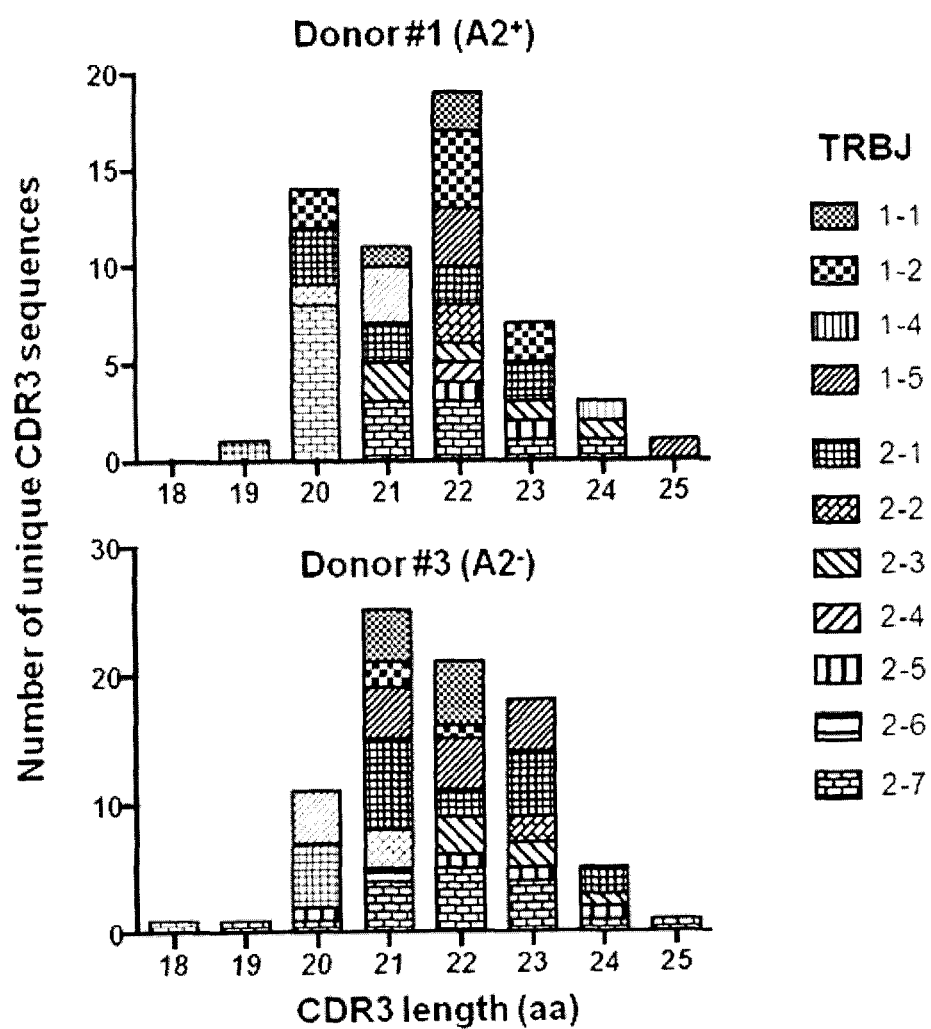
FIG. 4 is a bar chart identifying TCR beta variable gene 27 (TRBV27) clonotypes that can compose A2/MART1 TCR in conjunction with SIG35α are highly heterogeneous and unique. SIG35α-transduced CD8+ T cells in an A2+ or A2− donor were stimulated with 10 μg/mL MART1$_{27-35}$ peptide-pulsed wtA2-aAPC. A2/MART1 multimer+CD8+ T cells were sorted by flow cytometry cell sorting. TCR TRBV27 chains isolated from sorted T cells were sequenced. Jβ gene segments and CDR3 length of isolated TCR TRBV27 chains are shown.
Figure 5:
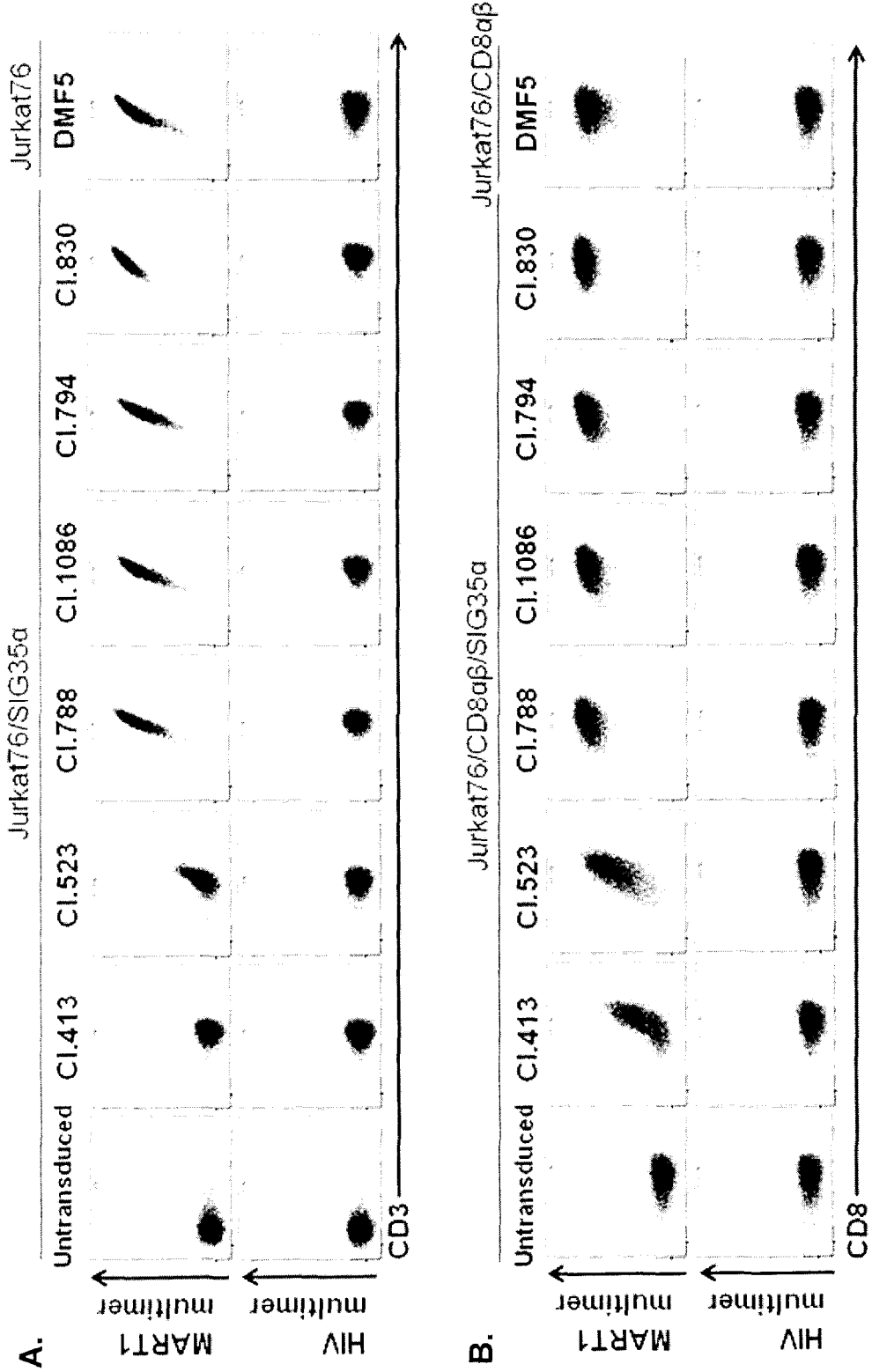
FIG. 5 is a cytometric analysis showing that the structural avidity range of A2/MART1 TCR consisting of SIG35α can be very broad in the absence or presence of CD8. A) Jurkat76 cells, which lack the expression of CD8αβ and intrinsic TCR, were retrovirally transduced with CD8αβ. Jurkat76 or Jurkat76/CD8αβ cells were stably transduced with individual TCRβ chains (clone: 413, 523, 788, 1086, 830, or 794) and TCRα SIG35α chain or DMF5 TCR. All transfectants were >95% positive for CD3. A2/HIV multimer was used as a negative control. Reconstituted A2/MART1 TCRs on Jurkat76 possess various structural avidities. Jurkat76 transfectants were stained with 2 μg/mL A2/MART1 multimer or A2/HIV multimer and α-human CD3 mAb. B) Reconstituted A2/MART1 TCRs on Jurkat76/CD8αβ possess various structural avidities. Jurkat76/CD8αβ transfectants were stained with 2 μg/mL A2/MART1 multimer or A2/HIV multimer and α-human CD8 mAb. C) Reconstituted A2/MART1 TCRs show a broad range of structural avidities. The structural avidity of Jurkat76 transfectants (left) and Jurkat76/CD8αβ transfectants (right) were assessed by multimer staining with graded concentrations of A2/MART1 multimer.
Figure 5:
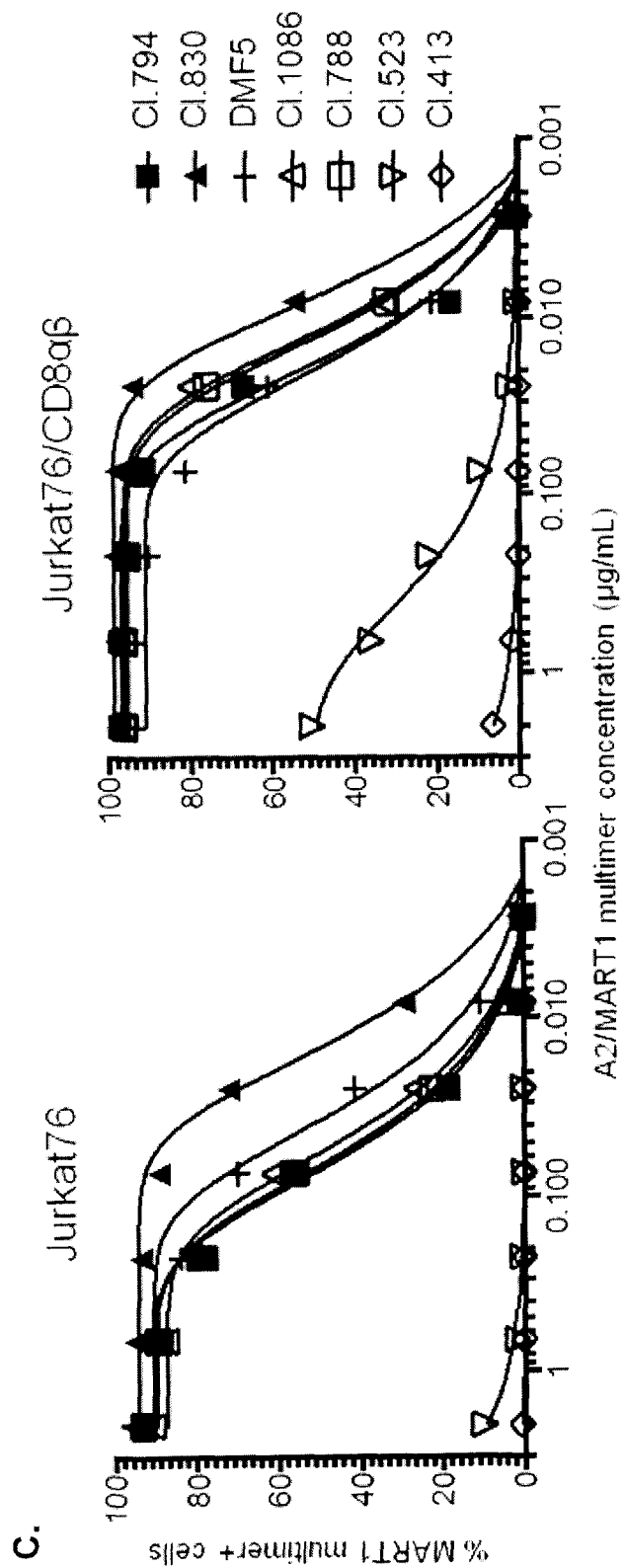
Figure 6:
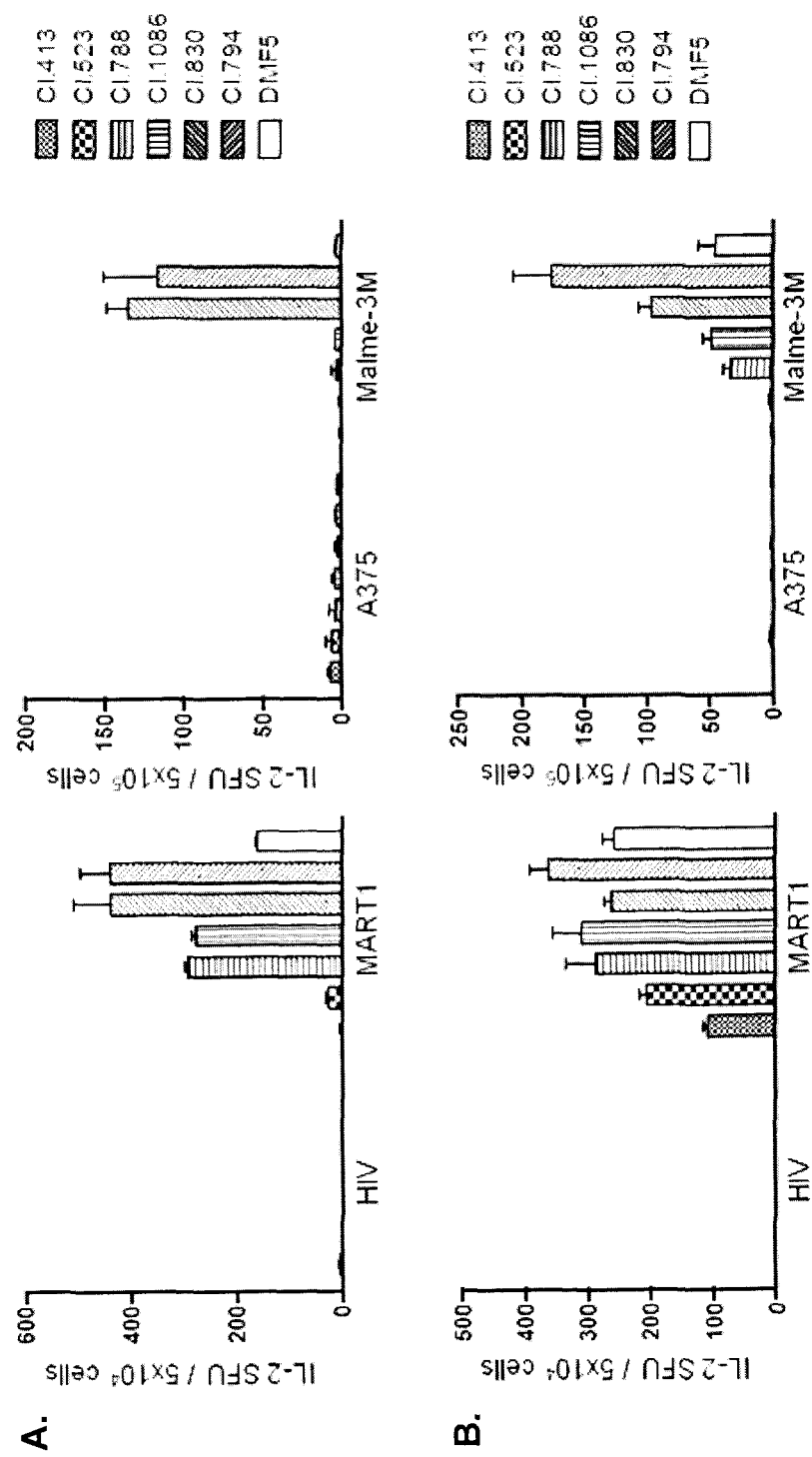
FIG. 6 is an ELISPOT assay showing that the functional avidity window of A2/MART1 TCR consisting of SIG35α can be very wide in the absence or presence of CD8. A) Jurkat76 or B) Jurkat76/CD8αβ cells were stably transduced with individual TCRβ chains (clone: 413, 523, 788, 1086, 830, or 794) and SIG35α chain or DMF5 TCR. All transfectants were >95% positive for CD3. Transfectants were subjected to IL-2 ELISPOT analysis. T2 cells pulsed with 10 μg/mL MART1$_{27-35}$ peptide or HIV pol476-484 peptide were used as stimulator cells (left). HIV pol476-484 peptide was used as a negative control peptide. The A2+/MART1+ melanoma line, Malme-3M and the A2+/MART1-melanoma line, A375 were used as stimulator cells (right). (A) Reconstituted A2/MART1 TCRs on Jurkat76 are highly avid for A2/MART1 recognition. IL-2 ELISPOT was performed in Jurkat76 transfectants using peptide-pulsed T2 cells (left) and tumor cell line targets (right). All experiments were carried out in triplicate and error bars show SD; (B) Reconstituted A2/MART1 TCRs on Jurkat76/CD8αβ are highly avid for A2/MART1 recognition. IL-2 ELISPOT was performed in Jurkat76/CD8αβ transfectants using peptide-pulsed T2 cells (left) and tumor cell line targets (right). All experiments were carried out in triplicate and error bars show SD; (C) Reconstituted A2/MART1 TCRs show various functional avidities. The functional avidity of Jurkat76 transfectants (left) and Jurkat76/CD8αβ transfectants (right) were assessed by IL-2 secreting using T2 cells pulsed with graded concentrations of MART1$_{27-35}$ peptide as stimulator cells.
Figure 6:
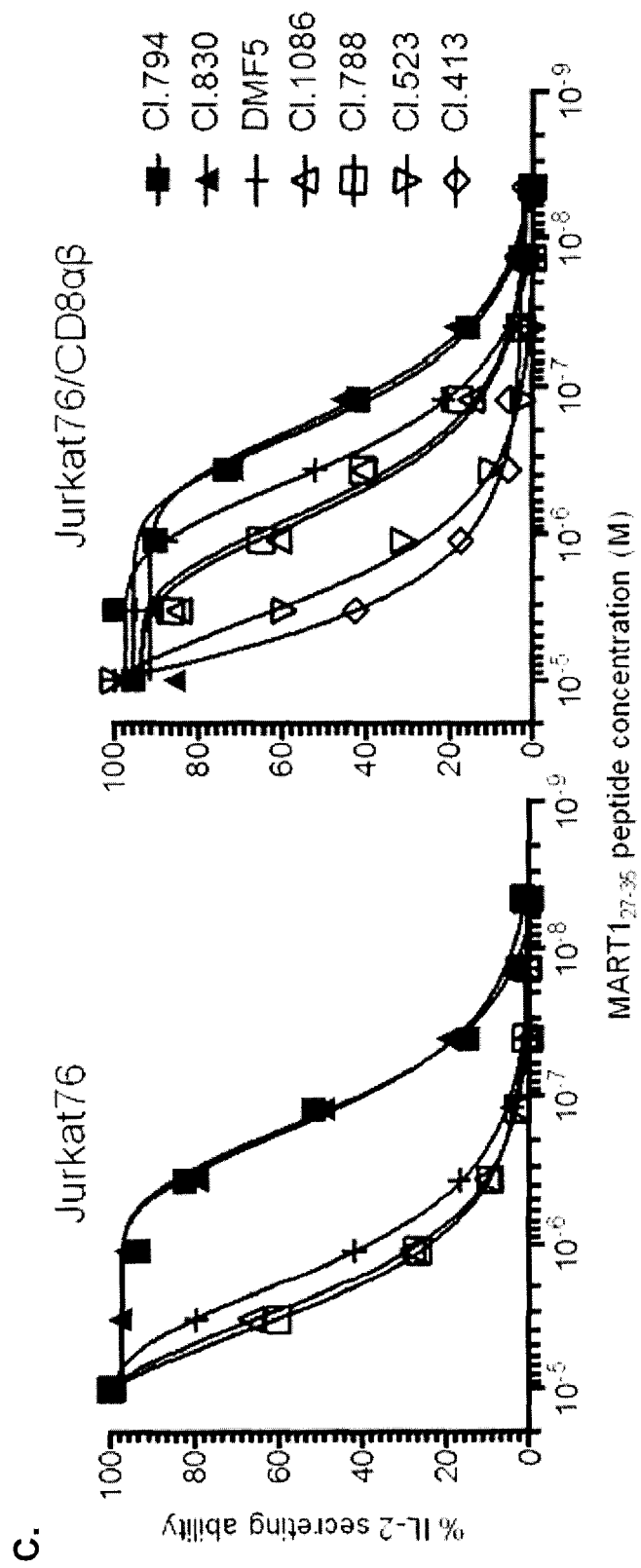
Figure 7:
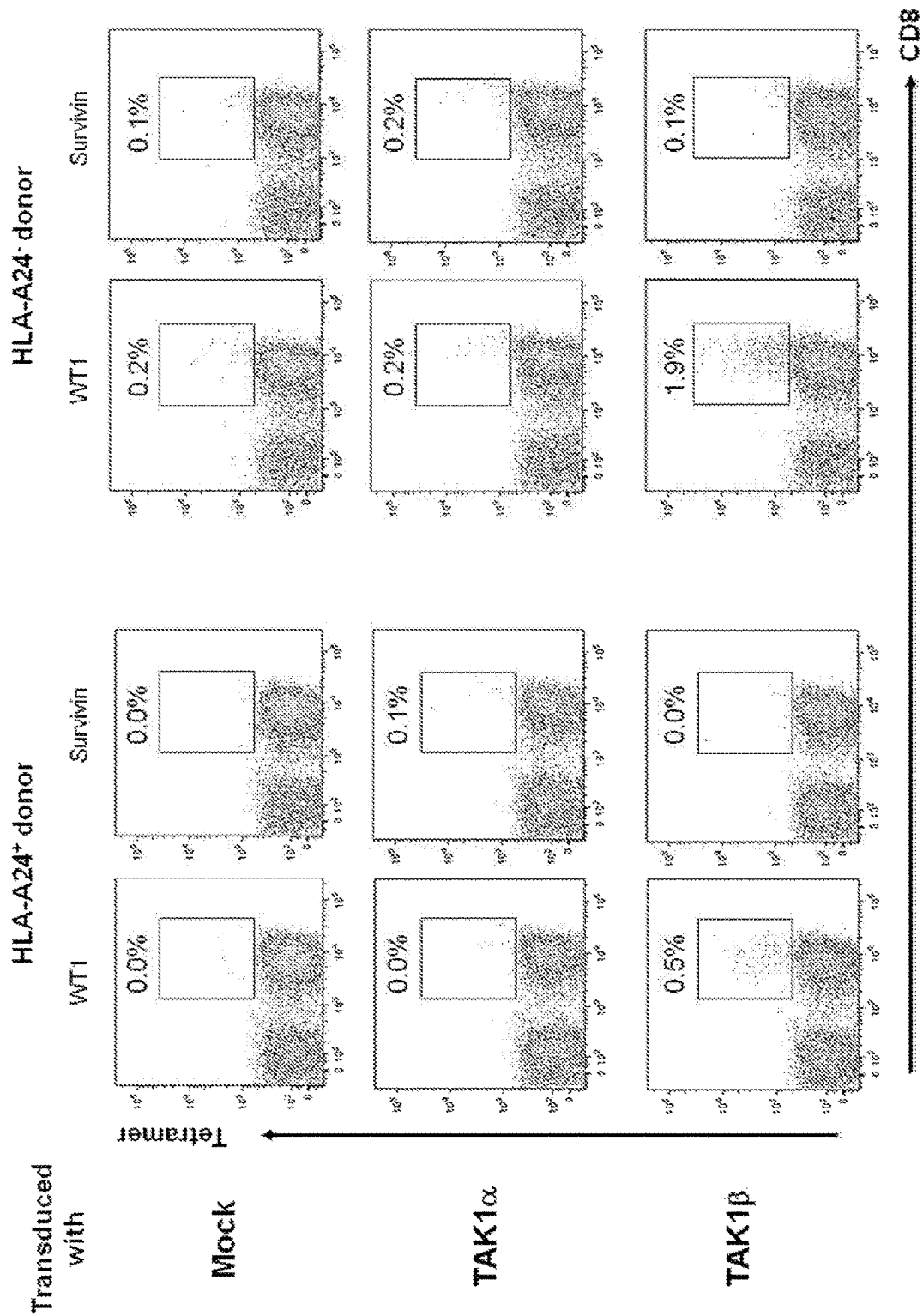
FIG. 7 is a flow cytometric analysis demonstrating TAK1β-centric recognition of A24/WT1. Peripheral T cells freshly isolated from 5 HLA-A*24:02 (A24)+ donors and 2 A24− donors were stimulated with 50 ng/mL α-human CD3 mAb (OKT3) in the presence of 100 IU/mL IL-2 and retrovirally transduced with truncated NGFR (ΔNGFR) gene (Mock), TAK1α/ΔNGFR or TAK1β/ΔNGFR gene. TAK1α or TAK1β gene and ΔNGFR gene was intervened by furin, sgsg and F2A sequence derived from foot and mouth disease virus. After 6 rounds of transduction, 2.0×10⁵ transfectants were stained with 50 μg/mL A24/WT1 heteroclitic peptide tetramer or A24/Survivin tetramer in conjunction with α-human CD8 mAb and α-human NGFR mAb. ΔNGFR-positive cells were gated and tetramer/CD8 positivity was analyzed. Representative tetramer-staining data of Mock (top), TAK1α (middle) and TAK1β (bottom)-transduced T cells obtained from one A24+ and one A24− donors out of 7 donors is shown.
Figure 8:
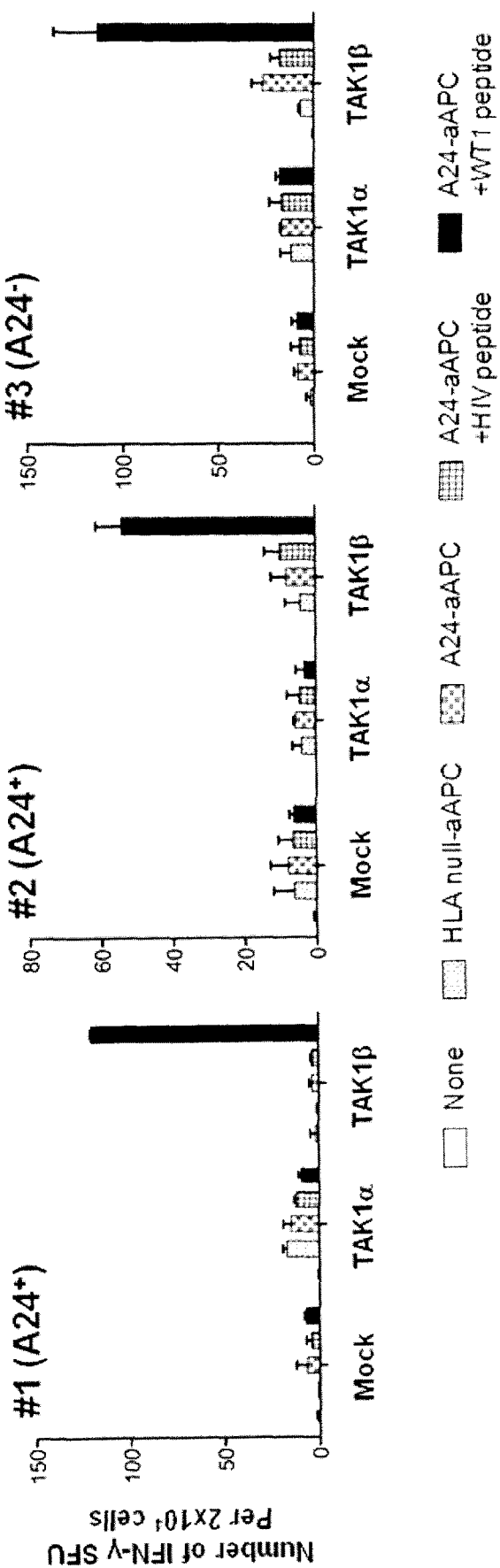
FIG. 8 is an ELISPOT assay demonstrating that TAK1β-transduced T cells stimulated with A24-aAPC expand and recognize A24/WT1 with reproducibility. CD8+ T cells derived from Mock, TAK1α and TAK1β-transduced T cells were isolated and stimulated with A24-aAPC cells loaded with 1 μg/mL WT1$_{235-243}$ heteroclitic peptide. Transduction efficiency in each gene-modified T cells was approximately 70%. Following 2 stimulations, TAK1β-transduced T cells derived from 7 out of 7 donors expanded. IFN-γ ELISPOT was conducted where 2.0×10⁴ gene-modified CD8+ T cells were co-cultured with HLA null-aAPC, A24-aAPC, A24-aAPC loaded with 1 μg/mL HIV-1 env584-592 peptide, A24-aAPC loaded with 1 μg/mL WT1$_{235-243}$ heteroclitic peptide or none of aAPC cells (indicated as each bar). TAK1β-transduced T cells derived from all 7 donors strongly produced IFN-γ against WT1 peptide pulsed A24-aAPC. Representative results from two A24+ and one A24− donors out of 7 donors are shown. All of experiments were carried out in triplicate and error bars show SD.
Figure 9:
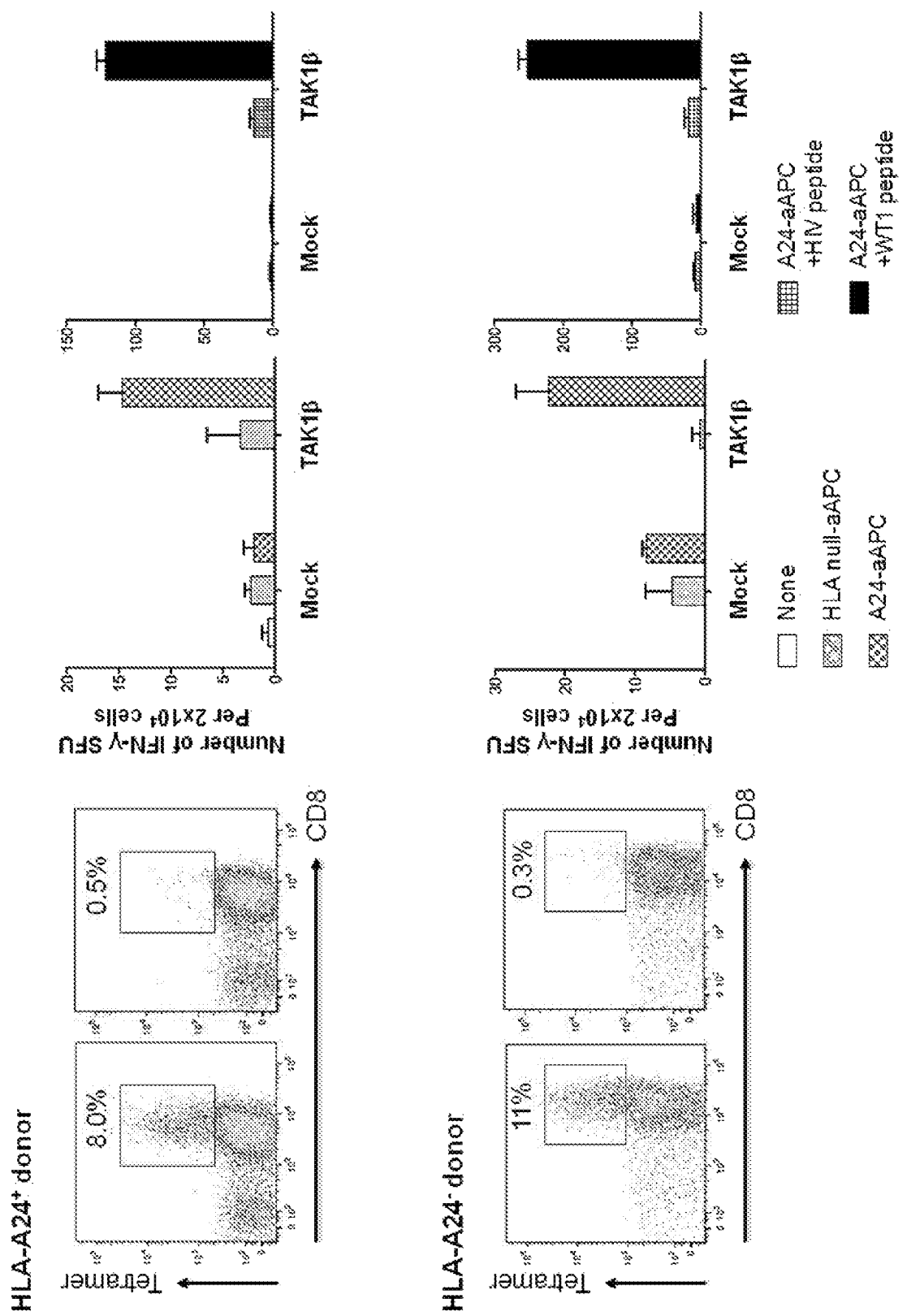
FIG. 9 is a flow cytometric analysis and ELISPOT assay showing that A24-aAPC stimulation of TAK1β-transduced T cells can enrich A24/WT1 T cells with high avidity. A representative result from 2 out of 7 donors is shown. TAK1β-transduced T cells were stained with 50 μg/mL A24/WT1 heteroclitic peptide tetramer or A24/Survivin tetramer in conjunction with α-human CD8 mAb and α-human NGFR mAb. ΔNGFR+ cells were gated and tetramer/CD8 positivity was analyzed. Tetramer-staining data of TAK1β-transduced T cells derived from one A24+ (top left)

It is demonstrated in FIG. 2, that thymic selection does not appear to affect the TCRβ repertoire that can constitute a peptide specific TCR with a prey TCRalpha nucleic acid (e.g. as demonstrated with SIG35α).

FIG. 20 shows a schematic of TCRs that can be obtained with single chain transduction (e.g. transduction of either the TCRalpha or the TCRbeta chain or a functional portion thereof. Single chain transduction (e.g. transduction of one TCR chain) produces a thymically unselected TCR repertoire with an unphysiological range of affinity, including TCRs with greater or lesser affinity/avidity for a specific peptide.

As shown in FIG. 22, single chain applications require transduction of for example an alpha or beta TCR polypeptide chain, which result in highly polyclonal TCR clonality, and highly broad TCR affinity/avidity.

For example, single chain gene transfer can generate high avidity antitumor T cells. As shown in Example 2, high affinity tumor-reactive TCRs from peripheral T cells were identified by generating a thymically unselected T cell repertoire. CD8+ T cells were transduced with a TCRalpha chain, SIG35alpha, and were able to recognize A2/MART1 peptide. Clonotypic TRBV27 TCRbeta chains were reconstituted with SIG35alpha on human TCRαβ-deficient T cells in the presence or absence of the CD8 co-receptor. Six transfectants, clones 8H, 7Q, 9J, 4K, 7E, 9I and 6X, presented higher avidity than the one expressing A2/MART1

TCR, DMF5. The transfectants also recognized A2+ MART1+ tumor cells in a CD8-independent manner (see Table 7).

Accordingly, the method allows for a variety of prey TCR chains to be identified which pair with the bait TCR chain to constitute a TCR with increased or decreased avidity and/or affinity compared to a control, optionally the parent TCR, or a preselected avidity and/or affinity.

In an embodiment, the prey TCR chain polypeptide which comprises a CDR3 region comprises at least one amino acid modification relative to the CDR3 region in a control TCR chain polypeptide CDR3 region, optionally the CDR3 region of the parent TCR chain. CDR3, which is the most hypervariable region of the TCR, can comprise from 6 to 20 amino acids and is a major determinant of peptide specificity. The at least one amino acid modification can for example be an amino acid change and or an increase or decrease in the number of amino acid residues in the region that constitutes the CDR3 region.

The isolated prey nucleic acid is in an embodiment, modified. Mutations in CDR3 can be introduced in an embodiment, to increase and/or decrease peptide affinity/avidity.

CDR1 and CDR2 are also determinates of peptide recognition (e.g. sequence and length) although to a lesser extent typically than CDR3. CDR1 for example can be swapped with other CDR1 regions. Other regions such as the constant region which are not directly involved in peptide recognition may tolerate changes that do not affect or only minimally affect peptide binding avidity and/or affinity. In an embodiment, the isolated prey nucleic acid is modified and comprises a prey CDR3 region in combination with a CDR2 and CDR1 region and a constant region, wherein the CDR1 and/or CDR2 region, and/or the constant region comprise one or more amino acid changes, optionally wherein the CDR1 region is swapped and/or wherein a portion of the constant region or other non-CDR region is deleted producing for example a truncated functional fragment.

In an embodiment, once a bait nucleic acid is isolated, a fused TCR and/or heterogeneous TCR can be constituted, optionally with the isolated prey TCR chain or a modified TCR prey chain and the bait TCR chain.

An isolated prey nucleic acid can also in an embodiment be used as a bait nucleic acid to identify a counterchain to the isolated prey nucleic acid, for example to provide a constituted TCR that comprises neither chain of the parent TCR.

In an embodiment, the bait polypeptide chain and the prey TCR polypeptide chain constitute a TCR with i) a high avidity and/or affinity (e.g. higher than a preselected standard); and/or ii) an increased avidity and/or affinity for the peptide of interest compared to the parent TCR.

In an embodiment, the obtaining step comprises testing, e.g. determining, the avidity and/or affinity of a constituted TCR (e.g. bait and cloned prey nucleic acid) for peptide binding avidity and/or affinity.

In an embodiment, the obtaining step comprises enriching for high avidity T cells, for example prior to cloning the prey TCR nucleic acids, optionally by stimulating T cells with an aAPC comprising a mutated HLA, optionally mutated HLA-A2. For example, mutated HLA-A2 abrogates binding to CD8 molecules without affecting affinity of the TCR/HLA interaction can be used to enrich for high avidity and/or affinity TCRs. It has been previously shown that artificial APC expressing mutated HLA-A2 can selectively expand high avidity antigen-specific T cells (Imataki et al., 2012).

In another embodiment, the obtaining step comprises one or more of isolating transduced/recombinant cells, cloning one or more prey TCR chain nucleic acids and expressing one of the cloned prey TCR chain nucleic acid in a cell to provide a heterogeneous TCR and testing the avidity and/or affinity of the heterogeneous TCR to the peptide of interest. In an embodiment a prey TCR chain nucleic acid which when constituted in a TCR imparts high avidity and/or affinity is isolated.

In an embodiment, the method is for identifying a TCR polypeptide chain that constitutes a TCR with a high avidity and/or affinity and/or an increased avidity and/or affinity for a peptide of interest, wherein the method further comprises introducing the cloned prey nucleic acid and the bait nucleic acid into a cell able to express a TCR or to differentiate into a cell able to express a TCR and measuring the avidity and/or affinity of the TCR comprising the prey TCR polypeptide chain and the bait TCR polypeptide chain; identifying a clone wherein the bait TCRalpha or TCRbeta polypeptide chain and the prey TCR polypeptide chain constitute a TCR having increased (or alternatively decreased) avidity and/or affinity for the peptide of interest compared to a control optionally the parent TCR.

In an embodiment, a cell expressing the heterogeneous TCR has an avidity sufficient to recognize a peptide of interest presented on a cell in the absence of exogenously pulsing the cells with peptide. For example in the case where the peptide of interest is a tumor antigen peptide the heterogeneous TCR can recognize a tumor cell presenting the tumor antigen in the absence of modification, e.g. without exogenously pulsing the tumor cell with the peptide of interest.

In an embodiment, the avidity and/or affinity of the heterogeneous TCR in increased at least 25%, at least 50%, at least 75%, at least 100%, at least 200%, at least 500% or more compared to a control such as the parent TCR.

In an embodiment, the avidity and/or affinity of the heterogeneous TCR in decreased at least 20%, at least 30%, at least 40%, at least 50%, at least 60%, at least 70%, at least 80% or more compared to a control such as the parent TCR.

In an embodiment, the increased avidity is an increased structural avidity and/or an increased functional avidity.

As used herein, the term "avidity" as used herein refers to a measure off multiple affinities, optionally the overall strength of binding, between an antigen with antigenic determinants (such as a peptide of interest), optionally presented by an antigen presenting cell, and a binding protein such an a TCR or antibody, optionally in the contest of a cell expressing the TCR or antibody, for example the overall strength of binding between a displayed peptide such as a tumor associated antigen and a TCR or the overall strength of binding between an aAPC displayed peptide such as a tumor associated antigen and a cell expressing a TCR. The term "functional avidity" as used herein is the concentration of an antigen (e.g. peptide) required to achieve 50% of maximal response in a functional assay. For each functional assay, the maximal response is determined. Functions measured include for example abilities to secrete cytokines such as IL-2 and IFN-gamma and to cytolyze. The maximal response is obtained when T cells are maximally stimulated. Therefore, maximal responses depend on the functional capabilities of given T cell(s) and can for example be expressed as EC50 in $\mu M$ or other molar units. The term "structural avidity" as used herein and which can be expressed as EC50 in $\mu g/mL$ or other concentration units, is the concentration of an antigen (e.g. a peptide multimer) required to achieve half maximal antigen staining (e.g.

multimer staining). Functional and structural avidity can for example be calculated with GraphPad prism 6 software.

The term "affinity" as used herein means the strength of a single interaction between for example a peptide (presented in the context of HLA) and a TCR. Affinity is measured for example where the peptide of interest is presented in a cell free context, for example where the HLA presented peptide is bound to a surface or bead.

As used herein "high avidity" means avidity sufficiently high to recognize target cells presenting a peptide of interest without any modification such as pulsing of exogenous peptides.

Functional avidity can be measured for example using an enzyme-linked immunospot (ELISPOT) assay and measuring for example, interferon-gamma (IFNgamma) and/or IL-2 production as described in the Examples, and/or a combination thereof. Structural avidity can be measured by staining, TCR expressing cells, optionally T cells using graded concentrations of HLA/peptide multimers. In some embodiments, avidity is assessed by flow cytometric analysis for specific TCR binding to fluorochrome-labeled multimeric synthetic HLA/peptide complexes, and/or functional assessment via transduction of peripheral blood lymphocytes and stimulating in vitro with peptide-pulsed, HLA-matched APC and screening for IFN-gamma production using standard enzyme-linked immunosorbent assay (ELISA) or ELLISPOT assays. In some embodiments, T cell avidity is detected via a dual stain cell sorting protocol that detects cells bound to the fluorescently labeled multimer in conjunction with an intracellular stain for IFN-gamma, indicating that the cell was activated by the recognition of the TCR-multimer complex.

In an embodiment, the bait TCR polypeptide chain, optionally the bait TCRalpha and/or bait TCRbeta polypeptide chain was expressed and previously isolated from a T cell recognizing said peptide of interest. In another embodiment, the bait polypeptide is constructed using known CDR1, CDR2 and CDR3 sequences.

An embodiment includes a method for producing a nucleic acid encoding a TCR polypeptide chain which in combination with a counterchain TCR polypeptide constitutes a TCR specific for a peptide of interest, the method comprising the steps of:
  (a) transducing a cell population comprising cells able to express a TCR or differentiate into cells expressing a TCR with a bait nucleic acid which encodes a TCR polypeptide chain selected from TCRalpha or TCRbeta polypeptide chains, which TCR polypeptide chain in combination with a counterchain TCR polypeptide chain constituted an expressed TCR, wherein the bait TCR polypeptide chain was previously isolated from a T cell recognizing said peptide of interest,
  (b) culturing the transduced cell population under conditions that permit the bait TCR polypeptide chain to be expressed;
  (c) obtaining one or more cells expressing the TCR specific for a peptide of interest from the transduced cell population obtained in step (b), and
  (d) isolating a prey nucleic acid encoding a prey TCR polypeptide chain which constitutes a TCR with the TCR polypeptide chain encoded by the bait nucleic acid transduced into said cell population from the cell obtained in step (c).

In another aspect, the present disclosure relates to a method for producing a pair of nucleic acids encoding a TCR specific for a peptide of interest, which comprises the steps of:

(a) transducing a cell population with a bait nucleic acid which encodes either one of TCRalpha or TCRbeta polypeptide chains constituting a TCR expressed and previously isolated from a T cell recognizing said peptide of interest, wherein said cell population comprising cells which are able to express a TCR or differentiate into cells expressing a TCR,
  (b) culturing the transduced cell population under conditions that permit the bait TCR polypeptide chain to be expressed;
  (c) selecting one or more cells expressing a TCR specific for a peptide of interest from the transduced cell population obtained in step (b),
  (d) isolating a prey nucleic acid encoding a TCR polypeptide chain which can constitute a TCR with the TCR polypeptide chain encoded by the bait nucleic acid from the one or more cells selected in step (c), and
  (e) pairing the bait nucleic acid transduced into said cell population in step (a) or a nucleic acid encoding a same chain TCR polypeptide chain with the prey nucleic acid isolated in step (d).

The steps for example of (a) (b) and (c) shown above of the method for producing a pair of nucleic acids of present disclosure can be carried out by the methodology described herein. The isolating step can be performed by common method for isolating TCR chain gene, for example, PCR using the primer complementary to a nucleic acid sequence encoding constant region of TCR peptide. If the prey nucleic acid has been cloned for example in step (c), the isolating step can comprise, selecting a clone prey nucleic acid with the desired avidity compared to the parental TCR, for example by propagating the vector comprising the prey nucleic acid and/or amplifying the prey nucleic acid from the selected cells.

The bait nucleic acid encoding the TCR polypeptide chain can be previously isolated from a cytotoxic T lymphocyte (CTL) and/or tumor infiltrating lymphocyte (TIL). In an embodiment, the CTL is isolated from a patient with a disorder such as cancers (e.g. leukemia, solid tumors and the like), hepatitis, infectious diseases caused by a virus (e.g. influenza virus, HIV or the like), a bacteria (e.g. *Mycobacterium tuberculosis*, MRSA, VRE or the like), a fungus (e.g. *Aspergillus, Candida, Cryptococcus* and the like) are indicated as examples.

Pairing can include cloning the bait and prey nucleic acids in a vector or separate vector and transducing the cell with the cloned prey and bait nucleic acids. It can also include combining the nucleic acids to encode a fused single chain TCR. The vector can be any kind of vector, for example for producing quantities of the cloned nucleic acids or for expression in a host cell.

Nucleic acids described herein including the nucleic acids paired may be used in various embodiments. Each of the nucleic acids may be combined and/or operatively linked with one or more elements controlling transcription or translation, or inserted into the vector, for example as described in (2). Particularly preferred embodiments include (i) a vector in which one or both of the isolated and/or paired nucleic acids are inserted, and (ii) a combination of vectors in which each of the paired nucleic acids is inserted. In the aspect of (i), the nucleic acids encoding the TCR polypeptide chains or other polypeptides may be transcribed and translated by separate promoters, respectively, or may be transcribed and translated by one promoter using an internal ribosome entry site (IRES) or a cleavage site between the polypeptide chains such as a furin cleavage site or a self-digesting foot and mouth disease virus F2A peptide (F2A).

The term "obtaining" and "producing" as used herein include at least one physical step and can include a selection assay, optionally FACS, chemical selection for example using a selection marker, TCR selection using antigen loaded antigen presenting cells and the like.

The term "operatively linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative linkage of DNA to a transcriptional control element refers to the physical and functional relationship between the DNA and promoter such that the transcription of such DNA is initiated from the promoter by an RNA polymerase that specifically recognizes, binds to and transcribes the DNA.

As used herein, the term "F2A" refers to the foot-and-mouth virus peptide and F2A like sequences that have been optimized that can mediate protein cleavage between to adjoined sequences. For example F2A peptide sequences can be cloned between nucleic acid molecules encoding a polypeptide allowing expression of multiple proteins from a single open reading frame. The F2A peptide is represented by SEQ ID NO: 70 and is encoded for example by a nucleic acid comprising SEQ ID NO: 69.

The term "furin cleavage site sequence" or "furin cleavage site" as used herein means a nucleic acid that encodes an amino acid sequence (or the encoded amino acid sequence) that is cleaved by a furin enzyme, including for example, amino acid RX(K/R)R (SEQ ID NO: 123), optionally RAKR (SEQ ID NO:66) which is encoded for example by the nucleic acid sequence comprising SEQ ID NO:65.

The term "furin" as used herein means a member of the subtilisin-like proprotein convertase family, having typically RX(K/R)R consensus motif (SEQ ID NO: 123) and includes without limitation all known furin molecules including naturally occurring variants and for example those deposited in Genbank with the accession numbers CAA27860 CAA27860.1, CAA37988.1, NP_062204.1, NP_003782.1, NP_001161382.1, which are specifically incorporated by reference. Furin is also known as Pace and PC1, PCSK3 SPC1.

In addition linker sequences can be added between discrete entities, e.g. the TCR chain and the marker, such as a sgsg sequence represented for example by SEQ ID NO: 68 which is encoded for example by a nucleic acid comprising SEQ ID NO:67.

As used herein, the term "sgsg" refers to a sequence of "Glycine" and "Serine" amino acids that can be used as a flexible spacer/linker, including for example Short Linkers such as (Gly-Gly-Ser-Gly) (SEQ ID NO: 124), Middle Linkers such as (Gly-Gly-Ser-Gly)×2, Long Linkers such as (Gly-Gly-Ser-Gly)×3. Other linkers include linkers described in the International Genetically Engineered Machine (iGEM) repository of Standard Biological parts.

In an embodiment the nucleic acid encoding the TCR polypeptide chain is combined with a nucleic acid encoding a selection marker polypeptide such as a nucleic acid encoding truncated NGFR polypeptide (ΔNGFR) represented by SEQ ID NO: 72 (e.g. encoded by a nucleic acid comprising SEQ ID NO:71) or any other useful marker e.g. for embodiments wherein the nucleic acid encoding the TCR polypeptide chain is transduced into a cell, suitable selectable markers include fluorescent proteins, such as EGFP and related molecules, and cell surface proteins not found in the cell to be transduced and preferably deleted of signaling activity, such as ΔNGFR, truncated EGFR, truncated CD19.

The selection marker can for example be fused to the TCR in a single ORF and/or comprised as a separate ORF in a vector. For example, the nucleic acid encoding the TCR polypeptide can be comprised in a vector further comprising the selectable marker.

Nucleic acid sequences encoding one or more cleavage sites, such as a furin cleavage site or F2A peptide, can be introduced between the nucleic acid encoding the TCR polypeptide chain and the nucleic acid encoding the selectable marker polypeptide, allowing for marker cleavage if desired.

A person skilled in the art in making a fusion construct, would recognize that the stop codons, for example, as found in the TCR chain sequences, would be deleted as shown for example in FIG. 21.

In an embodiment, the cell population transduction is repeated a second, third, fourth, fifth or sixth time, for example to increase the diversity of the prey TCR chain that can be baited.

(2) Cells Expressing a TCR Specific for a Peptide of Interest

In an aspect, the present disclosure relates to a method for producing a cell expressing a TCR specific for a peptide of interest, which comprises the step of transducing a cell population with a nucleic acid which encodes either one of two counterchain polypeptide chains (e.g. TCRalpha or beta) constituting a TCR, optionally where the nucleic acid was expressed and previously isolated from a T cell recognizing said peptide of interest, and wherein said cell population comprises a cell which is able to express a TCR or differentiate into a cell expressing a TCR. See for example FIG. 22. In an embodiment, the method further comprises introducing a nucleic acid encoding an additional TCR polypeptide chain, optionally the counterchain of an introduced or co-introduced TCR polypeptide chain (e.g. TCRalpha where TCR beta has been or is being co-introduced) or a different TCR polypeptide chain (e.g. TCRalpha and TCRdelta).

In an embodiment, the isolated prey nucleic acid encoding the prey TCR polypeptide chain is transduced into a population of cells comprising a cell which is able to express a TCR or can differentiate into a cell expressing a TCR, optionally wherein the isolated prey nucleic acid is transduced in combination with a nucleic acid encoding a TCR polypeptide chain that in combination with the prey TCR polypeptide chain constitutes a TCR, optionally the bait TCR nucleic acid, to produce a transduced cell population comprising cells expressing a TCR specific for a peptide of interest.

In an embodiment, an isolated bait nucleic acid encoding the bait TCR polypeptide chain is transduced into a population of cells comprising a cell which is able to express a TCR or can differentiate into a cell expressing a TCR, optionally wherein the isolated bait nucleic acid is transduced in combination with a nucleic acid encoding a TCR polypeptide chain that in combination with the bait TCR polypeptide chain constitutes a TCR, optionally the prey TCR nucleic acid, to produce a transduced cell population comprising cells expressing a TCR specific for a peptide of interest. The bait nucleic acid can in addition to encoding the bait polypeptide comprise one or more elements herein described. For example, the bait nucleic acid (and/or the prey nucleic acid for example when used to produce a TCR or recombinant cell) can comprise one or more elements described in [00155]. In the examples where TCR SIG35alpha and TAK1beta genes are used as bait, the bait nucleic acids comprise a sequence that encodes an insect-derived Fibroin light chain signal sequence at the N-terminus, which is efficiently cleaved. Accordingly in an embodiment, the bait nucleic acid (and/or a prey nucleic acid) comprises a non-native signal sequence such as an insect fibrion light chain signal sequence.

The cell population is in an embodiment selected for cells expressing the prey and/or bait nucleic acids.

The term "cell that can express a TCR" means as used herein any T cell including for example CD4+, CD8+ and double positive CD4+CD8+ cells and/or any cell that comprises the cellular machinery to express a TCR, either where the TCR is typically present endogenously in said cell type or where it is not endogenous and is introduced into the cell (e.g. by viral infection).

The term "cell that can differentiate into a cell expressing a TCR" means as used herein a cell can differentiate into a T cell such as a T cell precursor cell, a thymocyte, a hematopoietic stem cell, a bone-marrow cell, an embryonic stem cell or an induced pluripotent stem cell.

The bait nucleic acids which encode respective polypeptide chains (TCR chains) constituting the TCR specific for a peptide of interest can be identified and/or previously isolated, for example, as described above. As an example, an RNA is prepared from a T cell, for example, a CTL recognizing the peptide of interest by a conventional method, and then a cDNA is synthesized. Using the cDNA as a template, 5'-rapid amplification of cDNA end (RACE) is performed using an antisense primer complementary to a nucleic acid encoding the TCR constant region. 5'-RACE may be performed by a known method. For example, 5'-RACE can be performed using a commercially available kit such as SMART PCR cDNA Synthesis Kit (manufactured by Clontech). The nucleotide sequence of the DNA amplified by the aforementioned procedure is determined, the DNA encoding a TCR chain is selected. When the amino acid sequence of a polypeptide chain constituting a TCR is known, nucleic acids which encode the polypeptide chain can be synthesized chemically.

A "cDNA" is defined as copy-DNA or complementary-DNA, and is a product of a reverse transcription reaction from an mRNA transcript. "RT-PCR" refers to reverse transcription polymerase chain reaction and results in production of cDNAs that are complementary to the mRNA template(s).

In an aspect of the present disclosure, a cell is transduced with the nucleic acid encoding either a TCR alpha chain and/or a TCR beta chain. In the case that one TCR chain predominantly contributes to peptide recognition by the TCR, the nucleic acid encoding such TCR chain is preferably used in the present disclosure. A TCR centricity of the peptide recognition may be determined by crystal structure analysis.

Examples of the nucleic acid which encodes a TCR polypeptide chain include, but are not limited to, a nucleic acid including a variety of elements which enables the translation of a polypeptide encoded by the nucleic acid when said nucleic acid is introduced into a cell are added. For example, the nucleic acid which encodes the TCR polypeptide chain may include a promoter sequence (e.g., mammal-derived promoters such as phosphoglycerate kinase promoter, Xist promoter, β-actin promoter, RNA polymerase II promoter, etc., virus-derived promoters such as SV40 early promoter, cytomegalovirus promoter, thymidine kinase promoter of herpes simplex virus, LTR promoters of various retroviruses, etc.), a terminator sequence, an enhancer sequence, or other transcription control regions. Further, the nucleic acid may have a sequence which contributes to the translation of the TCR chain (Kozak sequence, etc.). Of course, the aforementioned elements are placed at functionally associated positions with each other so as to be suitable for the transcription of the nucleic acid to an RNA or the translation of a polypeptide. In the case where the nucleic acid is an RNA, elements relating to transcription control may not be added to the nucleic acid.

The nucleic acid which encodes a TCR polypeptide chain can be incorporated into a vector as described herein. In addition, the nucleic acid which is a DNA or an RNA can be also transduced directly into a cell to express the TCR polypeptide chain or chains.

The term "vector" as used herein is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g. promoter) for the expression of the inserted DNA. Common vectors include plasmid vectors, viral vectors such as retroviral vectors, lentiviral vectors, adeno-associated virus vectors, and adenoviral vectors.

A method of transducing a nucleic acid into a cell is not particularly limited, and can be a known method. For example, a method using an electroporation, a calcium phosphate, a cationic lipid or a liposome can be used. The nucleic acid can be easily introduced into a cell with high efficiency by using a commercially available transfection reagent.

As used herein, the term "transducing" or alternatively "transforming" which can be used interchangeably, refers to the introduction of a nucleic acid into a cell optionally via introduction into a cell's genome (e.g. using a retroviral method). The method of transducing a nucleic acid into a cell can include viral or non-viral methods such as electroporation, calcium phosphate, cationic lipid or liposome based methods, as well as gene gun, sonoporation, magnetofection, etc.) For example, the nucleic acid can be introduced into a cell with high efficiency by using a commercially available transfection reagent. A nucleic acid can be incorporated into a vector. The vector is not particularly limited, and a suitable vector may be selected and then used from known vectors such as a plasmid vector and a virus vector depending on the purpose.

A virus vector having the ability to infect a cell to introduce a foreign DNA into the cell is suitable in the present disclosure. In the present disclosure, known virus vectors such as a retrovirus vector (including lentivirus vector, pseudo-typed vector, etc.), an adenovirus vector, an adeno-associated virus vector, a herpesvirus vector, etc., can be used. A virus vector in which a nucleic acid encoding a TCR chain is inserted makes it possible to infect a target cell under the conditions suitable for each virus, and to transduce the nucleic acid into the cell. A retrovirus vector having the ability to incorporate an inserted foreign nucleic acid onto a chromosome is suitable for the present disclosure.

In an embodiment, the population of cells, such as a population of PBMC cells, is transduced 2×, 3×, 4×, 5×, 6× or more to increase the heterogeneity of endogenous TCR chains interacting with the transduced nucleic acid encoding a TCR polypeptide chain. A method of obtaining a T cell expressing a transduced TCR polypeptide chain at a high ratio to the endogenous TCR is known. In this method, the expression of the endogenous TCR chain which the T cell originally expresses is suppressed by antisense technology such as siRNA specifically targeted to the endogenous TCR chain (see WO 2008/153029). When the aforementioned method is applied to the present disclosure, a cell expressing a transduced TCR polypeptide chain or chains at a high ratio can be obtained by targeting an endogenous TCR RNA with a siRNA (or other means) that is different in sequence from the nucleic acid to be transduced. The nucleotide sequence to be transduced can be made based on the degeneracy of the genetic code so as it would not be knocked down by siRNA used. In an embodiment, the nucleotide sequence to be transduced (including for example the bait nucleic acid or a nucleic acid to be transduced in combination with a counterchain TCR chain nucleic acid) can be codon optimized.

Since a TCR plays an important role in recognition of an antigen by a T cell, a T cell transduced with a nucleic acid which encodes a TCR chain is one of the preferable aspect of the present disclosure. In this aspect, the nucleic acid may be transduced into a cell capable of differentiating into a cell which can express a TCR, thereafter, the cell may be differentiated into a T cell. Examples of the cell capable of differentiating into a cell which can express a TCR include a hematopoietic stem cell, a common lymphoid progenitor, and a T cell progenitor. In addition, it is not necessary that a cell used in an above transduction be fractionated into a single cell species. A cell population containing the cell, for example, a peripheral blood mononuclear cell (PBMC) population can be obtained from a subject into which a nucleic acid is transduced. In an embodiment, the transduction is repeated a second, third, fourth, fifth or sixth time. In addition, such cell population can be stimulated with CD3 ligand, lectin and the like to enhance the proliferation of T cells, for example prior to transduction, for example to increase the transduction efficiency.

The term "subject" includes all members of the animal kingdom, including human. In one embodiment, the subject is an animal. In another embodiment, the subject is a human.

In the present disclosure, CD3 ligand is not limited in particular as long as it is a substance having the feature of binding to CD3, but, for instance, it may be an anti-CD3 antibody, particularly preferably an anti-CD3 monoclonal antibody may be used. For instance, the monoclonal antibody OKT3 (Kuneg et al., 1979) is indicated as an example. There is no particular limitation on the concentration of CD3 ligand in the culture medium, but, for instance, when using an anti-CD3 monoclonal antibody, for instance, 0.001 to 100 μg/mL, and in particular 0.01 to 100 μg/mL concentrations are preferred.

Additionally, in the present disclosure, cells can also be co-stimulated by adding other co-stimulating factors such as CD28 ligand, as necessary.

The cell population containing the subject cell into which a nucleic acid is transduced may be collected from, for example, peripheral blood, bone marrow or umbilical blood of a human or a non-human mammal. If necessary, a T cell and/or a cell capable of differentiating into a T cell can be fractionated or enriched and then used in the present disclosure. When a nucleic acid is introduced in a cell for use for example in treating a cancer, the cell population can be collected from a patient to be treated, or a donor having an HLA type matched with or similar to that of the patient. Non-HLA matched donor cells can also be used as long as the transduced TCR recognizes the HLA/peptide complexes on recipient's cells, for example cancer cells when the peptide of interest is from a tumor associated antigen.

In the present disclosure, a cell population which has been transduced with a nucleic acid encoding a TCR chain may contain a cell expressing a T cell receptor (TCR) specific for a peptide of interest. The TCR expressed in such T cell consists of the TCR chain expressed from the transduced nucleic acid and another TCR chain endogenously expressed in the T cell. The cell population thus obtained can be stimulated with at least one stimulating factor selected from the group consisting of an antigen presenting cell presenting a peptide of interest, a peptide of interest, a CD3 ligand, a CD28 ligand, a cytokine, a chemokine and a cell having the capability of producing a cytokine or a chemokine.

Any cell having the capability of presenting a peptide (such as dendritic cells, macrophages, monocytes, B cells and the like) to which the appropriate peptide of interest has been added, a cell in which a gene is introduced to express the peptide of interest, or a cell collected from an organism, which presents the peptide of interest, can be used as an antigen presenting cell. In addition, an artificial antigen presenting cell (see WO 2003/065977) can be used in the present disclosure.

As used herein, the term "aAPC" refers to an artificial antigen-presenting cell. The aAPC can be any cell, including a fibroblastic cell, or antigen displaying fragment thereof, that is modified to display an antigenic peptide (e.g. the peptide of interest in the context of HLA) and optionally costimulatory molecules on a surface such that the peptide and/or costimulatory molecules is/are accessible for TCR activation. The aAPC can also be a bead or carrier comprising the peptide of interest (e.g. in the context of HLA) or any agent that can stimulate T cells in a peptide specific manner. Cytokine antibodies such as anti-CD3 antibodies and other TCR signaling effectors can be added for example to promote aAPC function, e.g. in assays presenting antigen to for example a T cell expressing a heterogeneous TCR, when costimulatory molecules are absent in the aAPC used. aAPC can comprise a single allele of HLA, for example aAPC comprising HLA-A2 for MART1 and HLA-A24 for WT1 are described herein.

As described in the Examples, an aAPC includes for example HLA null cells, such as K562 cells, transduced with costimulatory ligands such as CD80 and CD83, as well as HLA molecules and/or IL-21, anti-CD3 antibodies, for example wherein the stimulatory molecules and HLA complexed peptide are conjugated to a bead.

In the present specification, a peptide of interest is a peptide or a glycopeptide derived from tumor antigen, bacterial antigen or viral antigen. The peptide of interest may be a purified or isolated peptide. The peptide of interest may be a peptide obtained from tumor cell extracts, or tumor cell sonicates and tumor cell hot water extracts containing an antigen peptide, or processed materials of bacteria or virus. Peptides of interest include tumor antigen peptides such as any T cell defined tumor antigen, including for example peptides from cancer-germline genes, differentiation antigens expressed in malignancies, antigens overexpressed in tumors, including for example antigens described in Schultz et al., 2000; Vigneron et al., 2005; Tomita et al., 2011; Vigneron et al., 2012; Ma et al., 2011; Corbiere et al., 2011; Dalet, Stroobant et al., 2011; Charpiro et al., 2006; Guillaume et al., 2010; Dalet, Robbins et al., 2011; Vigneron et al., 2004; Skipper et al., 1996; Hanada et al., 2004; Chaux et al., 1999; and Zarour et al., 2000. A peptide from any antigen that is for example expressed by cancer cells but not by normal cells and that can be presented to T cells can be used.

In the method of the present disclosure for producing the cell, the well-known culture media prepared by mixing constituents that are necessary for cell culture, for example, suitable for the lymphocyte culture can be used. For instance, commercially available culture media can be selected and used appropriately. These culture media may contain cytokines, appropriate proteins and other constituents in addition to the original ingredients thereof. Preferably, a culture medium containing IL-2 cytokine is used. There is no particular limitation on the concentration of IL-2 in the culture medium, but it may be for instance, preferably 0.01 to $1 \times 10^5$ U/mL, more preferably 1 to $1 \times 10^4$ U/mL. In addition, for instance, fibronectin, fibronectin fragment or anti-IL-4 antibody can be used as an appropriate protein.

There is no particular limitation on the cell culture instrument used in the method for producing the cell selected in the present disclosure. For instance, plates, flasks, bags, large culture containers, bioreactors or the like can be used. For example, a $CO_2$ gas-permeable cell culture bag can be used as bag. In addition, although the cultivation can be carried out in an open system or a closed system, it is preferred to carry out the cultivation in a closed system from the point of view of safety of the selected cell.

In addition to being dissolved to coexist in the culture medium, co-stimulating factors such as CD3 ligand or fibronectin fragment, appropriate protein, cytokines or other constituents contained in the culture medium may also be immobilized on an appropriate solid phase, for instance, cell culture instrument such as plates, flasks and bags, cell culture supports such as beads, membrane or slide glass. There is no particular limitation on the material of these solid phases as long as it can be used for cell cultivation.

In the present specification, a cytokine is not limited in particular as long as it can act on and activate a lymphocyte, however, for instance, IL-2, IFN-γ, TGF-β, IL-15, IL-7, IFN-α, IL-12, CD40L, IL-27 and the like are indicated as examples, and from the point of view of enhancing cellular immunity, IL-2, IL-15 and IL-21 are particularly preferably indicated as examples.

In the present specification, there is no particular limitation on a cell capable of producing a cytokine, but, for instance, from the point of view of enhancing cellular immunity, Th1 cell is indicated as an example.

By adding antigen stimulation to a cell obtained by the method of the present disclosure, induction of a useful antigen-specific lymphocyte is allowed, with extremely high cytotoxic activity and high antigen recognition capability. The cell produced in the present disclosure can survive in an organism over a long period, being an extremely useful cell having high therapeutic effects.

In the present specification, production of a cell or a cell population is synonymous to cultivation of a cell or a cell population, and means a process that comprises each step of induction (activation), maintenance, expansion of the cell or cell population, and/or steps combining these.

The method for producing a cell in the present disclosure may further comprise the step of selecting, separating or isolating a cell expressing a TCR specific for a peptide of interest from a cell population transduced with a nucleic acid. This step can be carried out by using a complex (tetramer or multimer) of the peptide of interest and major histocompatibility complex (MHC) (e.g. using a MHC tetramer assay) or by the method based on the property of a cell, for example, a response against a cell presenting the peptide of interest (cytotoxicity or release of cytokine, etc.). In addition, the present disclosure comprises the step of selecting, separating or isolating a cell expressing TCR which has low allogeneic response.

For example, as shown in Example 3, the antigen reactivity and allogeneic reactivity in human T cells can be separated at the molecular level by modulating the primary structure of TCRs. TAK1, a WT1-specific TCR clone, recognizes the HLA-A*24:02/WT1235-243 (A24/WT1) while possessing allo-reactivity for HLA-B"57:01 (B57). T cells transduced with a TAK1β chain reconstituted with TRAV36 TCRα chains were shown to be reactive to both A24/WT1 and B57, however TAK1β chains reconstituted with non-TRAV36 TCRα chains showed reactivity to A24/WT1, but not to B57, thus demonstrating that antigen-specific reactivity and allo-reactivity of clonotypic TCRs are separable by modulating the primary structure of TCRs.

For example T cells that are less allogeneically reactive can be selected based on the decreased reactivity to antigen-presenting cells expressing specific allogeneic (non-self) HLA molecules in in vitro assays such as a cytokine ELISPOT assay. To determine alloreactivity, one can screen against a panel of antigen-presenting cells expressing different allogeneic HLA molecules, to identify which specific HLA molecules are associated with alloreactivity. As demonstrated in the Examples, B57 confers alloreactivity to the A24-restricted WT1 (235-243) peptide-specific TCR, clone TAK1. B57 can confer alloreactivity to other clonotic TCRs with unknown HLA-restriction and antigen specificity.

(3) The Cell Population Comprising the Cell Expressing a TCR, and the Method for Treating a Disorder The present disclosure relates to the cell population comprising the cell expressing a TCR specific for a peptide of interest obtained by a method described in (2). In addition, the present disclosure relates to the cell population comprising the cell expressing a TCR encoded by the pair of nucleic acids obtained by the method described in (1).

Furthermore, the present disclosure relates to the method for treating a disorder comprising the step of administering to the subject a therapeutically effective amount of said cell population.

Also provided is use of a nucleic acid, composition and/or cell population produced using a method described herein for treating a disorder. Another aspect is a nucleic acid, composition or cell population produced using a method described herein for treating a disorder.

The cell population produced by the method of the present disclosure is a cell population comprising a cell that recognizes a peptide of interest. For instance, such a cell population is useful for the treatment of a variety of disorders because it provides a cytotoxic activity against a cell presenting the peptide recognized by the TCR. Although there is no particular limitation on the disorder for which the cell population or composition comprising the cell population is administered, for instance, cancers (leukemia, solid tumors and the like), hepatitis, infectious diseases caused by a virus (influenza virus, HIV or the like), a bacteria (*Mycobacterium tuberculosis*, MRSA, VRE or the like), a fungus (*Aspergillus, Candida, Cryptococcus* and the like) are indicated as examples. In addition, the cell population produced by the method of the present disclosure can also be used for donor lymphocyte infusion for the purpose of achieving remission of relapsed leukemia, or the like.

In an example, Epstein-Barr virus(EBV)-specific cytotoxic T lymphocytes generated from EBV-seropositive blood donors have been used to successfully treat patients with EBV-positive post transplantation lymphoproliferative disease on the basis of the best HLA match and specific in vitro cytotoxicity (Barker et al., 2010, Hague et al., 2007). Hague et al., 2007 reported that out of 33 patients, 14 achieved a complete remission, 3 showed a partial remission and 16 had no response. Patients receiving CTLs with closer HLA matching responded better.

Infused cells, for example recombinant T cells transduced and expressing a heterogeneous TCR, may not have to be recipient-derived and HLA-matched. However, the transduced TCR must recognize the HLA/peptide complexes on the recipient's cells, for example cancer cells when the peptide of interest is a cancer peptide. Hence, the subject cell (e.g. cancer cell) must express an HLA type that is utilized by the heterogeneous TCR to recognize the peptide of interest. Depending on the peptide and the HLA, the donor cell can comprise for example 6, 7, 8 or 9 matching HLA.

The population of cells infused or to be infused can comprise cells expressing different heterogeneous TCRS, optionally directed to the same or different peptides of interest.

Furthermore, the present disclosure provides a pharmaceutical composition (therapeutic agent) comprising the above cell population and/or isolated and/or recombinantly engineered nucleic acid as an active ingredient, optionally in combination with a pharmaceutically acceptable carrier. The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The therapeutic agent containing the cell population is appropriate for use in immunotherapy. In immunotherapy, a cell appropriate for the treatment in a patient is administered, for instance, via injection or drip infusion transvenously, transarterially, subdermally, intraperitoneally or the like. The therapeutic agent is can be used for the above-mentioned disorder or donor lymphocyte infusion. The therapeutic agent can be prepared, for instance, as a drip infusion agent or an injectable agent according to a well-known method in the pharmaceutical field, by mixing the cell population prepared by the method of the present disclosure as an active ingredient, with a well-known organic or inorganic carrier, diluent, stabilizer or the like, which is appropriate for parenteral administration. The content of cell population of the present disclosure in the therapeutic agent, the dosage of the therapeutic agent and the conditions for the therapeutic agent can be determined appropriately according to well-known immunotherapies. For instance, although there is no particular limitation on the content of cell population of the present disclosure in a medicine, the cell concentration may be preferably $1\times10^3$ to $1\times10^{11}$ cells/mL, more preferably $1\times10^4$ to $1\times10^{10}$ cells/mL and even more preferably $1\times10^5$ to $1\times10^9$ cells/mL. In addition, although there is no particular limitation on the dosage of the medicine of the present disclosure, for instance, the adult dosage may be preferably $1\times10^6$ to $1\times10^{12}$ cells/day, more preferably $1\times10^7$ to $5\times10^{11}$ cells/day and even more preferably $1\times10^8$ to $2\times10^{11}$ cells/day. In addition, combinations of the immunotherapy with the therapeutic agent and a medicinal therapy by administration of well-known medicines, or a treatment by radiotherapy or surgical operation can be used.

The present disclosure further provides a therapeutic or prophylactic method for a disorder comprising administering to a subject an effective amount of the cell population obtained by the above-mentioned method. Although there is no particular limitation on the subject herein, preferably, an organism (for instance a human patient, or a non-human animal) with the above-mentioned disorder for which the cell population prepared by the method of the present disclosure is administered, is indicated. The therapeutic agent of the present disclosure containing as active ingredient a cell population into which a nucleic acid encoding the TCR is introduced, is administered to a subject expressing an HLA molecule that is identical to or has up to three locus mismatches with the HLA molecule expressed by the cell population.

In an embodiment, the cell population is purified prior to administration.

As used herein the term "purified cell population" as used herein refers to a population of cells that has been removed and separated (e.g. isolated) from a mixed or heterogeneous population of cells and/or other components such as culture medium. In some embodiments, a purified cell population is a substantially pure population of transduced cells as compared to the heterogeneous population from which the cells were isolated or enriched from.

The term "substantially pure", with respect to a particular cell population, refers to a population of cells that is at least about 65%, preferably at least about 75%, at least about 85%, more preferably at least about 90%, and most preferably at least about 95% pure, with respect to the cells making up a total cell population. Similarly, with regard to a "substantially pure" population, refers to a population of cells that contain fewer than about 30%, fewer than about 20%, more preferably fewer than about 15%, 10%, 8%, 7%, most preferably fewer than about 5%, 4%, 3%, 2%, 1%, or less than 1%, of cells that are not transduced.

The term "treatment" as used herein as applied to a subject, refers to an approach aimed at obtaining beneficial or desired results, including clinical results and includes medical procedures and applications including for example pharmaceutical interventions, surgery, radiotherapy and naturopathic interventions as well as test treatments. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

In addition, the term "effective amount" as used herein is the amount of the cell population, exerting therapeutic or prophylactic effects when the cell population is administered to the subject, compared to a subject into which the cell population has not been administered. While a specific effective amount can vary depending on the dosage form, administration method, purpose of use, age and body weight of the subject, symptoms and the like, preferably, it is similar to the above-mentioned medicines. The administration method is also not limited, but, for instance, administration by drip infusion, injection or the like is preferred, similarly to the above medicines.

Provided herein in another aspect is a use of a cell comprising a heterogeneous TCR, a population of cells comprising said cell, a therapeutic agent, an agent comprising a heterogeneous TCR conjugated to an agent such as an antibody and/or a toxic moiety, a nucleic acid encoding a single chain heterogeneous TCR and/or a pair of nucleic acids which together encode a heterogeneous TCR, or a pharmaceutical composition comprising one of the aforementioned products for alleviating a symptom and/or treating a subject, optionally a subject afflicted by a cancer or other disease expressing a peptide recognized by the heterogeneous TCR.

For example, adoptive transfer of TCR gene-modified T cells may be used for cancer immunotherapy. As shown in Example 2, adoptive transfer of SIG35alpha transduced T cells was also shown to inhibit in vivo growth of A2+

MART1+ tumor cells. This strategy was also used to in generate CD8+ T cells specific for peptides expressed in other types of malignancies, including A2/NYESO-1 and A2/Her2.

(4) Isolated Molecules

The present disclosure also provides novel TCR chains and CDR3 region polypeptides and nucleic acids encoding such TCR chains and CDR3 regions including for example, one or more of the sequences described herein. A cell expressing a TCR specific for the MART1$_{27-35}$ peptide, represented by SEQ ID NO: 73, can be obtained by using the nucleic acid encoding SIG35α chain which has an amino acid sequence of SEQ ID NO2. The TCR expressed in obtained T cell is formed by SIG35α chain and a β chain endogenously expressed in the transduced cell. For example, Clone 794 and Clone 830 each express a TCR constituted by the SIG35α chain and the endogenously expressed TCR β chain, and having a high avidity to the MART1$_{27-35}$ peptide. An isolated and/or recombinantly engineered nucleic acid encoding the TCR β chains of Clone 794 (SEQ ID NO:4) and clone 830 (SEQ ID NO:6) are included in the present disclosure. Similarly, a cell expressing a TCR specific for the WT1$_{235-243}$ peptide, represented by SEQ ID NO: 74, can be obtained by using the nucleic acid encoding TAK1β chain which has an amino acid sequence of SEQ ID NO:16. Clone T53, Clone A262, Clone T243 and Clone T262 each express a TCR constituted by the TAK1β chain and the endogenously expressed TCR α chain, and having a high avidity to the WT1$_{235-243}$ peptide. A nucleic acid encoding the TCR α chains of Clone T53 (SEQ ID NO:8), Clone A262 (SEQ ID NO:10), Clone T243 (SEQ ID NO:12) and Clone T262 (SEQ ID NO:14) are included in the present disclosure. In addition, Clone 8H, Clone 7Q and Clone 9J each express a TCR constituted by the SIG35α chain and the endogenously expressed TCR β chain, and having a high avidity to the MART1$_{27-35}$ peptide. An isolated and/or recombinantly engineered nucleic acid encoding the TCR β chains of Clone 8H (SEQ ID NO:94), Clone 7Q (SEQ ID NO:96) and Clone 9J (SEQ ID NO:98) are included in the present disclosure The term "recombinantly engineered" as used herein means an entity prepared using recombinant technology and not existing in nature, for example such as cDNA, a transduced cell, labelled nucleic acids (e.g. labelled with a fluorescent or radioactive label), chimeric nucleic acids and polypeptides and the like.

In another aspect, the disclosure includes an isolated and/or recombinantly engineered polypeptide comprising a sequence selected from SEQ ID NOs: 4, 6, 8, 10, 12, 14, 52, 54, 56, 58, 60, 62, 81-91, 94, 96, 98, 112, 114, 116-122 and/or a sequence having at least 85%, at least 90%, at least 95%, at least 96%, at least 97%, at least 98% or at least 99% sequence identity to a sequence selected from to a sequence selected from SEQ ID NOs: 4, 6, 8, 10, 12, 14, 52, 54, 56, 58, 60, 62, 81-91, 94, 96, 98, 112, 114, 116-122 or a portion thereof such as a CDR region or a non-CDR region. In an embodiment, the polypeptide is encoded by a nucleic acid selected from any one of SEQ ID NOs: 3, 5, 7, 9, 11, 13, 51, 53, 55, 57, 59, 61, 93, 95, 97, 111, 113, 115 and/or a sequence having at least 85%, at least 90%, at least 95%, at least 96%, at least 97%, at least 98% or at least 99% sequence identity to a sequence selected from SEQ ID NOs: 3, 5, 7, 9, 11, 13, 51, 53, 55, 57, 59, 61, 93, 95, 97, 111, 113, 115 and/or a portion thereof that encodes for example a CDR region or a non-CDR region. In an embodiment the polypeptide comprises a sequence of any one of SEQ ID NOs: 4, 6, 8, 10, 12, 14, 52, 54, 56, 58, 60, 62, 81-91, 94, 96, 98, 112, 114, 116-122.

A further aspect includes an antibody or binding fragment thereof that is specific for any one of SEQ ID NOs: 52, 54, 56, 58, 60, 62, 81-91, 94, 96, 98, 112, 114 and 116-122. Methods for making antibodies are known in the art. In an embodiment, the antibody is monoclonal antibody. In an embodiment the antibody is a polyclonal antibody.

In yet another aspect, the disclosure includes an isolated and/or recombinantly engineered nucleic acid comprising a sequence as shown in any one of SEQ ID NOs: 3, 5, 7, 9, 11, 13, 51, 53, 55, 57, 59, 61, 93, 95, 97, 111, 113 and 115.

Another aspect includes an isolated and/or recombinant TCR polypeptide chain comprising a CDR3 sequence selected from SEQ ID NO: 52, 54, 56, 58, 60 62 and 81 to 91, 94, 96, 98, 112, 114 and 116-122.

A further aspect includes an isolated and/or recombinantly engineered TCRbeta chain polypeptide wherein the CDR3 region comprises any one of SEQ ID NOs: 52, 54, 81 to 91, 112, 114 and 116 to 122.

A further aspect includes an isolated and/or recombinantly engineered TCR comprising a TCRbeta chain polypeptide wherein the CDR3 region comprises any one of SEQ ID NOs: 52, 54, 81 to 9, 112, 114 and 116 to 122.

Also provided is an isolated and/or recombinantly engineered TCRalpha chain polypeptide wherein the CDR3 region comprises any one of SEQ ID NOs: 56, 58, 60 and 62.

Another aspect includes an isolated and/or recombinantly engineered TCR comprising a TCRalpha chain polypeptide wherein the CDR3 region comprises any one of SEQ ID NOs: 56, 58, 60 and 62.

In an embodiment, the isolated TCR polypeptide chain comprises and/or is selected from any amino acid sequence shown in Table 1.

In another embodiment, the TCR polypeptide chain comprises a CDR1 region having a sequence selected from any one of the amino acid sequences shown in Table 1, for example SEQ ID NO: 18, 20, 22, 24, 26, 28, 30, 32, 100, 102 or 104; a CDR2 region having a sequence selected from any one of the amino acid sequences shown in Table 1, for example SEQ ID NO: 34, 36, 38, 40, 42, 44, 46, 48, 106, 108 or 110; and a CDR3 region having a sequence selected from any one of the amino acid sequences shown in Table 1, for example SEQ ID NO: 50, 52, 54, 56, 58, 60, 62, 64, 87-92 and 111-122.

In an embodiment, the TCRalpha polypeptide chain comprises a CDR1 region comprising the sequence of SEQ ID NO: 20, a CDR2 region comprising the sequence of SEQ ID NO: 36 and a CDR3 region comprising the sequence of SEQ ID NO: 52. In another embodiment, the TCRbeta polypeptide chain comprises a CDR1 region comprising the sequence of SEQ ID NO: 22, a CDR2 region comprising the sequence of SEQ ID NO: 38 and a CDR3 region comprising the sequence of SEQ ID NO: 54. In yet another embodiment, the TCRalpha polypeptide chain comprises a CDR1 region comprising the sequence of SEQ ID NO: 24, a CDR2 region comprising the sequence of SEQ ID NO: 40 and a CDR3 region comprising the sequence of SEQ ID NO: 56. In another embodiment, the TCRalpha polypeptide chain comprises a CDR1 region comprising the sequence of SEQ ID NO: 26, a CDR2 region comprising the sequence of SEQ ID NO: 42 and a CDR3 region comprising the sequence of SEQ ID NO: 58. In an embodiment, the TCRalpha polypeptide chain comprises a CDR1 region comprising the sequence of SEQ ID NO: 28, a CDR2 region comprising the sequence of SEQ ID NO: 44 and a CDR3 region comprising the sequence of SEQ ID NO: 60. In yet another embodiment, the TCRalpha polypeptide chain comprises a CDR1 region comprising the sequence of SEQ ID NO: 30, a CDR2 region comprising the sequence of SEQ ID NO: 46 and a CDR3 region comprising the sequence of SEQ ID NO: 62.

In an embodiment, the isolated TCR polypeptide chain is a recombinant TCR comprising a label or tag. In an embodiment, the polypeptide comprises at least one amino acid difference from a sequence described herein.

In an embodiment, the isolated TCR polypeptide chain comprises a sequence selected from SEQ ID NO: 4, 6, 8, 10, 12, 14, 94, 96 and 98.

Also provided is an isolated nucleic acid molecule encoding one of the TCR chain polypeptides, optionally comprising a tag or label. In an embodiment, the nucleic acid comprises at least one nucleotide difference from a sequence described herein optionally wherein said nucleotide difference encodes at least one amino acid chain.

In an embodiment, the isolated nucleic acid encoding a TCR polypeptide chain comprises and/or is selected from any nucleic acid sequence shown in Table 1.

Another aspect includes an isolated and/or recombinantly engineered cell comprising a TCR comprising a TCR alpha polypeptide and a TCR beta polypeptide wherein the TCR-beta chain polypeptide comprises a CDR3 region having a sequence selected from any one of SEQ ID NOs: 52, 54, 81 to 91, 112, 114 and 116 to 122.

Another aspect of the disclosure is an isolated and/or recombinantly engineered cell comprising a TCR comprising a TCR alpha polypeptide and a TCR beta polypeptide wherein the TCRalpha polypeptide chain comprises a CDR3 region having a sequence selected from any one of SEQ ID NOs: 56, 58, 60 and 62.

In an embodiment, the isolated and/or recombinantly engineered cell comprises a nucleic acid encoding a TCR chain comprising any one of SEQ ID NOs: 52, 54, 56, 58, 60, 62, 81 to 91, 112, 114 and 116 to 122.

In an embodiment, the nucleic acid is comprised in a composition, optionally in combination with a diluent, such as water and/or buffer.

In an embodiment, the polypeptide is comprised in a composition, optionally comprising a lipid membrane. In an embodiment, the polypeptide is comprised in a complex with CD3. In an embodiment, the complex comprises a TCR (optionally TCRalpha and TCRbeta) and CD3 consisting of a CD3γ chain, a CD3δ chain, and two CD3ε chains.

In an embodiment, the cell is comprised in a composition, optionally comprising an isotonic buffer.

In another aspect the paired nucleic acids are used to provide an isolated recombinantly engineered TCR.

Reference is made herein to the "IMGT nomenclature". The IMGT nomenclature as used herein refers to the nomenclature used for naming immunoglobulins, TCR, MHC including HLA, by the ImMunoGeneTics information system and for HL follows the following rule. The first three letters indicate the locus. The fourth letter indicates the V, D, J, or C region. The next couple of numbers or letters allow for the unambiguous identification of the gene. Alleles are denoted by an asterisk followed by a two-figure number (D1222-D1227 Nucleic Acids Research, 2013, Vol. 41, Database issue, The IMGT/HLA database, James Robinson). The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

The present disclosure will be further explained more in more detail by way of Examples, which the present disclosure is not limited to.

Example 1

Cells

The PG13 cell line and the phoenix-eco cell line were cultured in DMEM medium supplemented with 10% fetal calf serum (FCS) and 50 µg/mL gentamicin (Gibco). The Jurkat76 cell line, which is a Jurkat cell subclone that lacks the expression of CD8αβ and intrinsic TCR molecule, was cultured in RPMI 1640 medium supplemented with 10% FCS and 50 µg/mL gentamicin. HLA-null K562 cells that were transduced with CD80 and CD83 genes were additionally transduced with HLA-A*02:01 or HLA-A*24:02 gene and used as an aAPC. In some experiments, mutated-aAPC cells that were transduced with a mutated HLA-A*02:01 gene bearing two amino acid substitutions at positions 227 and 228 (D227K/T228A) and human IL-21 gene in lieu of wild-type HLA-A*02:01 gene were used. aAPC cells were also cultured in RPMI 1640 medium supplemented with 10% FCS and 50 µg/mL gentamicin. Particularly, mOKT3-aAPC cells, which were transduced with the heavy and light chains of a membranous form of α-human CD3 mAb (clone OKT3) instead of HLA class I molecule, were cultured in RPMI 1640 medium supplemented with 1 mg/mL G418 sulfate (Cellgro), 2.5 µg/mL puromycin (InvivoGen) and 50 µg/mL gentamicin. SupT1 and T2 cells obtained from American Type Culture Collection (ATCC) were cultured in RPMI 1640 supplemented with 10% FCS and 50 µg/mL gentamicin. Melanoma cell lines, A375 (HLA-A*02:01$^+$, MART1$^-$) and Malme-3M (HLA-A*02:01$^+$, MART1$^+$) obtained from ATCC were cultured in DMEM supplemented with 10% FCS and 50 µg/mL gentamicin. Peripheral blood mononuclear cells from healthy volunteers were isolated and stored in liquid nitrogen until use.

Construction of SIG35α, TAK1α and TAK1β Retroviral Vector

A TCRα chain, cloned from the HLA-A*02:01-restricted and MART1$_{27-35}$ (A2/MART1)-specific TCR and designated as SIG35α, was reported as a public TCRα chain (Dietrich et al., 2003, Trautmann et al., 2002, Li et al., 2010). The HLA-A*24:02-restricted and WT1$_{235-243}$ (A24/WT1)-specific TCRα and TCRβ genes were cloned from an established CTL clone, TAK1, using the 5' RACE method (Clontech). The SIG35α gene is TRAV12-2/TRAJ35/Cα, and the TCRα and TCRβ genes of TAK1 are TRAV20/TRAJ33/Ca and TRBV5.1/TRBD2/TRBJ2-1/Cβ2, respectively. SIG35α, TAK1α and TAK1β genes were codon-optimized and each gene was linked with furin cleavage sequence, sgsg linker and foot-and-mouth disease virus (F2A) peptide followed by truncated NGFR gene (ΔNGFR) and the construct was integrated into a pMX retroviral vector. Ecotropic retroviral vectors were obtained by transient transfection of SIG35α/ΔNGFR, TAK1α/ΔNGFR or TAK1β/ΔNGFR retroviral plasmid with TransIT293 (Mirus Bio) to the phoenix-eco cell line; subsequently, PG13 cell lines were transduced with the ecotropic retroviral vectors and cloned. High-titer GaLV-pseudotyped retroviral vectors were obtained from a stable PG13 cell line and used for transduction into human peripheral T cells.

Establishment of TCR Gene-Transduced T Cells

Peripheral blood mononuclear cells (PBMCs) were isolated from healthy volunteers and stimulated with 50 ng/mL α-human CD3 mAb (clone OKT3) in the presence of 100 IU/mL human IL-2 (Proleukin; Novartis) 3 days before transduction. Then, T cells were transduced with the SIG35α/ΔNGFR retroviral vector by centrifuging 1 hour at 1000 g at 32° C. for following 6 days. To measure the frequency of A2/MART1-specific T cells after transduction, the cells were labeled with α-human CD8 mAb (clone B9.11; Beckman Coulter), α-human NGFR mAb (clone ME20.4; Biolegend) and PE-conjugated HLA-A*02:01/MART1$_{26-35}$ heteroclitic multimer (Proimmune), HLA-A*02:01/HIV pol$_{476-484}$ multimer (Proimmune) or HLA-A*02:01/Flu$_{58-66}$ multimer. In other experiments, the TAK1α/ΔNGFR or TAK1β/ΔNGFR gene was also transduced into stimulated T cells as described above to see which TCR chain has a dominant role in dictating A24/WT1 specificity. To evaluate the positivity of WT1-specific T cells after transduction, the cells were labeled with antibodies described above and PE-conjugated HLA-A*24:02/WT1$_{235-243}$ heteroclitic tetramer or HLA-A*24:02/Survivin-2B$_{80-88}$ tetramer. The labeled cells were analyzed using a CANTO™ II flow cytometer (Becton Dickinson) and FlowJo Version 7.6.4 software (TreeStar). The frequency of tetramer and CD8$^+$ gene-modified T cells was analyzed by gating of ΔNGFR$^+$ cells.

Stimulation of Gene-Modified T Cells with aAPC Cells

To establish antigen-specific T cell lines, CD8$^+$ gene-modified T cells were obtained by CD8$^+$ T cell isolation kit (MACS® beads; Miltenyi Biotec). For expansion of A2/MART1-specific CD8$^+$ gene-modified T cells, wtA2-aAPC cells which express wild-type HLA-A*02:01 molecule or mutA2-aAPC cells which express mutated HLA-A*02:01 molecule and human IL-21 described above instead of wild-type HLA-A*02:01 was pulsed with 10 μg/mL MART1$_{27-35}$ peptide (AAGIGILTV) (SEQ ID NO: 73). For expansion of A24/wT1-specific CD8$^+$ gene-modified T cells, A24-aAPC cells which express HLA-A*24:02 molecule was pulsed with 1 μg/mL WT1$_{235-243}$ heteroclitic peptide (CYTWNQMNL) (SEQ ID NO: 74). aAPC cells were pulsed with peptides in serum-free RPMI 1640 medium for 6 hour at room temperature. Then, aAPC cells were irradiated with 20,000 rads, washed, and added to purified CD8$^+$ gene-modified T cells at a ratio of 1:20 in 24-well plates in RPMI supplemented with 50 μg/mL gentamicin and 10% human AB serum (Gemini Bio-products). The following day, redirected CD8$^+$ T cell cultures were supplemented with low dose of human IL-2 (10 IU/mL) and human IL-15 (10 ng/mL) (PeproTech) every 3 to 4 days. Repeat stimulations were done every 7 days. Following 2 rounds of stimulation, lines were evaluated for each tetramer positivity and IFN-γ secretion. The frequency of tetramer and CD8$^+$ gene-modified T cells was analyzed by gating of ΔNGFR$^+$ cells.

Analysis of TRBV Usage in A2/MART1-Specific Gene-Modified T Cells

As shown in Tables 1 and 2 TCR Vβ subtype analysis was performed on A2/MART1 multimer$^+$ CD8$^+$ T cells with the Beta Mark TCR Vβ Repertoire kit (Beckman-Coulter). The nomenclature used for the TCR Vβ subtype analysis is the one from Wei et al., 1994.

Cloning of TCRβ Chains Paired with SIG35α and TCRα Chains Paired with TAK1β

Total RNA was extracted from the SIG35α/ΔNGFR or TAK1β/ΔNGFR transduced T cells using the TRIzol (Ambion) according to the manufacturer's instructions. Full-length TCRβ genes that contain TRBV27 and paired with SIG35α were amplified by RT-PCR using a TRBV27 specific forward primer, 5'-TRBV27 (5'-ATCCCAGTGTG-GTGGTACGGGAATTCTGCCATGGGCCCCCAGCTC-CTTGGC-3'), (SEQ ID NO: 75) and β constant region specific reverse primers, 3'-Cβ-1 (5'-ATCGTCGACCACT-GTGCTGGCGGCCGCTCGAGTTCCAGGGCTGCCT-TCAGAAATCC-3') (SEQ ID NO: 76) and 3'-Cβ-2 primer (5'-GACCACTGTGCTGGCGGCCGCTCGAGCTAGC-CTCTGGAATCCTTTCTCTTGACCATTGC-3') (SEQ ID NO: 77). Full-length TCRα genes paired with TAK1β were cloned as follows. Briefly, cDNA was prepared by SMART RACE cDNA Amplification Kit (Clontech). For the first PCR, cDNA was amplified using a 5'-RACE primer and a 3'-TCRα UTR region primer; 5'-GGAGAGTTCCCTCT-GTTTGGAGAG-3' (SEQ ID NO: 78). The second-round semi-nested PCR was performed by using a first PCR product as a template, a modified 5'-RACE primer; 5'-GT-GTGGTGGTACGGGAATTCAAGCAGTGGTAT-CAACGCAGAGT-3' (SEQ ID NO: 79) and a 3'-TCRa constant region primer; 5'-ACCACTGTGCTGGCGGC-CGCTCAGCTGGACCACAGCCGCAGCG-3' (SEQ ID NO: 80). Each TCRβ or TCRα chain amplicon was cloned into the pMX retroviral vector by Gibson Assembly reaction and sequenced. TCRβ or TCRα gene names are in accordance with IMGT unique gene nomenclatures. Cloned pMX/TCRβ or pMX/TCRα plasmids were directly used for transduction.

ELISPOT Assay 96-well flat-bottom polyvinylidene difluoride plates (Millipore) were coated with capture α-human interferon-gamma (IFN-γ) mAb (clone 1D1K; MABTECH) or α-human Interleukin-2 (IL-2) mAb (R&D Systems) and incubated overnight at 4° C. After being washed with PBS supplemented with 2% FCS, T cells were incubated with $2.0\times10^4$ per well of indicated APC in the presence or absence of peptides in RPMI 1640 medium supplemented with 10% FCS for 20-24 hour at 37° C. Peptides used were 10 μg/mL MART1$_{27-35}$ or 10 μg/mL HIV pol$_{476-484}$ peptide for A2/MART1 and 1 μg/mL WT1$_{235-243}$ heteroclitic peptide or HIV-1 env$_{584-592}$ peptide for A24/WT1. After incubation, plates were washed and incubated with biotin-conjugated detection α-human IFN-γ mAb (7-B6-1; MABTECH) or α-human IL-2 mAb (R&D system) overnight at 4° C., followed by exposure to HRP-conjugated streptavidin (SA) for IFN-γ or ALP-conjugated SA for IL-2. To reveal specific spots, 100 μL of 0.1 M acetate buffer containing 3-amino-9-ethylcarbazole (Sigma-Aldrich) and 0.015% $H_2O_2$ for IFN-γ or 100 mM Tris-HCl (pH9.5) buffer containing 100 mM NaCl and 0.5 mM $MgCl_2$ and nitro blue tetrazolium/5-bromo-4-chloro-3-indolyl-phosphate (Promega) for IL-2 was added to each well. After 40 minutes, the color reaction was interrupted by washing with water, and the plates were dried. Diffuse large spots were counted using ImmunoSpot® Version 5.0.2 software (Cellular Technology Limited).

Evaluation of A2/MART1-Specific TCR Reactivity and A24/WT1-Specific TCR Reactivity To investigate A2/MART1 reactivity, Jurkat76 cell lines were retrovirally transduced with SIG35α gene with or without CD8αβ gene. Following transduction of these genes, Jurkat76/SIG35α or Jurkat76/CD8αβ/SIG35α transfectants were additionally transduced with TCRβ gene (clone: 413, 523, 788, 1086, 830, or 794) and sorted with human CD3 MACS® beads system (Miltenyi Biotec). Jurkat76 cell lines were also transduced with an A2/MART1-specific TCR, designated as DMF5, with or without CD8αβ gene. Jurkat76/DMF5 TCR transfectants and Jurkat76/CD8αβ/DMF5 TCR transfectants were also established to compare A2/MART1 reactivity of DMF5 TCR with that of SIG35α/TCRβ TCRs. These Jurkat76 transfectants were stained with HLA-A*02:01/MART1$_{27-35}$ heteroclitic multimer with graded concentrations to evaluate structural avidity of TCR for A2/MART1. Functional avidity was tested using T2 cells pulsed with graded concentrations of MART1$_{27-35}$ peptide as stimulators in an IL-2 ELISPOT assay. To assess A24/WT1 reactivity, Jurkat76/CD8αβ transfectants were transduced with TAK1β gene. Jurkat76/CD8αβ/TAK1β transfectants were additionally transduced with TCRα gene (clone: T53, A262, T243, T262) or parent TAK1α gene and sorted with FITC-conjugated α-human Vβ5.1 mAb (Beckman Coulter) and an α-FITC-MACS® beads system (Miltenyi Biotec). The established Jurkat76/CD8αβ/TAK1β/TCRα cell lines were evaluated for A24/WT1 reactivity in an IL-2 ELISPOT assay. In some experiments, these Jurkat76 transfectants were used to see the reactivity for A2/MART1 or A24/WT1 that naturally processed and presented on tumor cell surface. Malme-3M cells were used for A2/MART1-specific TCRs and A24-aAPC cells were used for A24/WT1-specific TCRs.

Example 2: TCR Single Chain Gene Transfer Generates High Avidity Antitumor T Cells Adoptive transfer of TCR gene-modified T cells is technically feasible and a promising treatment for cancer immunotherapy. However, thymic selection and peripheral tolerance make it difficult to identify high affinity tumor-reactive TCRs from peripheral T cells. To efficiently isolate high affinity TCRs, a thymically unselected T cell repertoire was generated by introducing peripheral T cells with a single TCR chain gene (e.g. also referred to herein as a hemichain), which alone can dictate HLA-restricted peptide specificity. A shared TCRα gene (clone SIG35α) has been isolated from multiple HLAA*02:01(A2)/MART1 CD8+ T cell clones expressing different clonotypic TCRβ chains. When transduced with SIG35α, peripheral CD8+ T cells, from both A2+ and A2− donors, recognized A2/MART1 and expanded in an A2/MART1-specific manner. In all donors tested, A2/MART1 multimer+ cells predominantly expressed TRBV27 TCRβ chains and their CDR3β sequences were highly diverse (see FIGS. 24 and 25)]. Eleven clonotypic TRBV27 TCR1β chains were individually reconstituted with SIG35α on human TCRαβ-deficient T cells in the presence or absence of the CD8 co-receptor. These transfectants possessed a broad range of structural and functional avidities (>2 orders of magnitude). As shown in Table 6, six out of 11 transfectants demonstrated higher avidity than the one expressing A2/MART1 TCR, clone DMF5, and recognized A2+ MART1+ tumor cells in a CD8-independent manner. Adoptive transfer of polyclonal SIG35α chain-transduced CD8+ T cells inhibited the growth of A2+ MART1+ tumor cells in vivo. Importantly, the single chain TCR gene transfer strategy was successfully extended to generating CD8+ T cells specific for A2/NYESO-1 and A2/Her2.

Example 3: Molecular Separation of Antigen Reactivity and Allogeneic Reactivity in Human T Cells A routine strategy to separate graft versus leukemia (GVL) effect from graft versus host disease (GVHD) in allogeneic hematopoietic stem cell transplantation (HSCT) is still lacking. It has been shown that a clonotypic T-cell receptor (TCR) can possess not only MHC-restricted antigen-specific reactivity but also allogeneic MHC-restricted reactivity (allo-reactivity). It was investigated whether GVL and GVHD caused by T cells are separable at a molecular level by modulating the primary structure of TCRs. Wilms tumor 1 (WT1) is a tumor-associated antigen overexpressed in many tumors but not normal cells. A WT1-specific TCR, clone TAK1, which recognizes the HLA-A*24:02/WT1235-243 (A24/WT1) while possessing allo-reactivity for HLA-B*57:01 (B57) was previously isolated. Peripheral T cells transduced with the TAK1β chain but not with the TAK1α chain recognized both A24/WT1 and B57 in all 6 donors tested including two A24-negative donors. Importantly, the A24/WT1 reactivity shown by polyclonal TAK1β-transduced T cells did not correlate with the B57 allo-reactivity. Forty three A24/WT1 and/or B57 reactive TCRs composed of different TCRα chains along with TAK1β chain on CD8α/β+ TCR− T cell line were reconstituted. It was found that A24/WT1 reactivity and B57 allo-reactivity of TRAV36 TCRα chains paired with TAK1β chain did correlate (R2=0.904, p<0.0001). In contrast, A24/WT1 and B57 reactivities of non-TRAV36 TCRα chains reconstituted with TAKβ chain did not (R2=0.031, p<0.471). A clonotypic non-TRAV36 TCRα chain reactive for A24/WT1 but not B57 was successfully identified. These results suggest that antigen-specific reactivity and allo-reactivity of clonotypic TCRs are separable by modulating the primary structure of TCRs.

TABLE 1

Sequences of A2/MART1 TCRα (clone SIG35α) and paired TCRβ

| Donor | Clone | TRAV | CDR3α | TRAJ | TRBV | CDR3β | TRBJ |
|---|---|---|---|---|---|---|---|
| Healthy | 5H9 | 12-2 | CAVSIGFGNVLHC (SEQ ID NO: 50) | 35 | 27 | CASSLLGGSTDTQYF (SEQ ID NO: 81) | 2-3 |
| Patient A | 4C8 | 12-2 | CAVSIGFGNVLHC (SEQ ID NO: 50) | 35 | 27 | CASSPIDGLNTEAFF (SEQ ID NO: 82) | 1-1 |
| Patient B | 31 | 12-2 | CAVSIGFGNVLHC (SEQ ID NO: 50) | 35 | 27 | CASSFNDEQFF (SEQ ID NO: 83) | 2-1 |

TABLE 1-continued

Sequences of A2/MART1 TCRα (clone SIG35α) and paired TCRβ

| Donor | Clone | TRAV | CDR3α | TRAJ | TRBV | CDR3β | TRBJ |
|---|---|---|---|---|---|---|---|
| Patient C | 31 | 12-2 | CAVSIGFGNVLHC (SEQ ID NO: 50) | 35 | 27 | CASSPSQGGNTEAFF (SEQ ID NO: 84) | 2-1 |
| Patient C | 16 | 12-2 | CAVSIGFGNVLHC (SEQ ID NO: 50) | 35 | 27 | CASSDSTASSEQFF (SEQ ID NO: 85) | 2-1 |
| Patient D | 29 | 12-2 | CAVSIGFGNVLHC (SEQ ID NO: 50) | 35 | 5.1 | CASSLSGSGDEQFF (SEQ ID NO: 86) | 2-1 |

Clone SIG35alpha can pair with multiple distinct clonotypic TCRβ chains to recognize A2/MART1.

TABLE 2

Sequencing results of TCR TRBV27 chains isolated from A2/MART1 multimer+ CD8+ T cells

| | wtA2-aAPC stimulation | | mutA2-aAPC/IL-21 stimulation | |
|---|---|---|---|---|
| Donor | Number of unique clonotypes | Number of isolates sequenced | Number of unique clonotypes | Number of isolates sequenced |
| #1 | 56 | 190 | 12 | 19 |
| #3 | 83 | 122 | 26 | 89 |
| Total | 139 | 312 | 38 | 108 |

TABLE 4

Sequences of A24/WT1TCRα

| Clone | TRAV | CDR3α | TRAJ |
|---|---|---|---|
| T53 | 36 | CAVITGGTSYGKLTF (SEQ ID NO: 56) | 52 |
| A262 | 36 | CAVQNAGGTSYGKLTF (SEQ ID NO: 58) | 52 |
| T243 | 36 | CAVLTQTGANNLFF (SEQ ID NO: 60) | 36 |

TABLE 3

Functional and structural avidities of the A2/MART1 TCRs

| Clone | Donor | Stimulation | TRBV | CDR3β | TRBJ | Functional avidity w/o CD8 EC50 (μM) | Functional avidity w/ CD8 EC50 (μM) | Structural avidity w/o CD8 EC50 (μg/mL) | Structural avidity w/ CD8 EC50 (μg/mL) |
|---|---|---|---|---|---|---|---|---|---|
| CI.794 | #3 (A2−) | mutA2-aAPC/IL-21 | 27 | CASSLLGDYGYTF (SEQ ID NO: 52) | 1-2 | 0.12 | 0.16 | 0.06 | 0.02 |
| CI.830 | #3 (A2−) | mutA2-aAPC/IL-21 | 27 | CASSLGGAYEQYF (SEQ ID NO: 54) | 2-7 | 0.13 | 0.14 | 0.01 | 0.006 |
| DMF5 | — | — | 6-4 | CASSLSFGTEAFF (SEQ ID NO: 87) | 1-1 | 1.4 | 0.33 | 0.03 | 0.02 |
| CI.1086 | #3 (A2−) | wtA2-aAPC | 27 | CASSLHGPGGYTF (SEQ ID NO: 88) | 1-2 | 2.4 | 0.63 | 0.04 | 0.01 |
| CI.788 | #3 (A2−) | wtA2-aAPC | 27 | CASGPSYEQYF (SEQ ID NO: 89) | 2-7 | 2.9 | 0.57 | 0.05 | 0.01 |
| CI.523 | #3 (A2−) | wtA2-aAPC | 27 | CASGSYEQYF (SEQ ID NO: 90) | 2-7 | — | 2.7 | — | 0.3 |
| CI.413 | #1 (A2+) | wtA2-aAPC | 27 | CASSVFGGDMGEKLFF (SEQ ID NO: 91) | 1-4 | — | 10 | — | — |

Functional avidity, expressed as EC50 in μM, was defined as the concentration of peptide required to achieve 50% of maximal response. Structural avidity, expressed as EC50 in μg/mL, was defined as the concentration of A2/MART1 multimer required to achieve half maximal multimer staining. They were calculated with GraphPad prism 6 software.

TABLE 4-continued

Sequences of A24/WT1TCRα

| Clone | TRAV | CDR3α | TRAJ |
|---|---|---|---|
| T262 | 20 | CAVQALRNNAGNNRKLIW (SEQ ID NO: 62) | 38 |
| TAK1a | 20 | CAVQAVDSNYQLIW (SEQ ID NO: 92) | 33 |

TABLE 5

List of Sequences

| SEQ ID NO | NAME OF SEQUENCE | SEQUENCE |
|---|---|---|
| 1 | TCRα chain, Clone SIG35α nucleotide sequence | See FIG. 12 |
| 2 | TCRα chain, Clone SIG35α amino acid sequence | See FIG. 12 |
| 3 | TCRβ chain, Clone 794 nucleotide sequence | See FIG. 13 |
| 4 | TCRβ chain, Clone 794 amino acid sequence | See FIG. 13 |
| 5 | TCRβ chain, Clone 830 nucleotide sequence | See FIG. 14 |
| 6 | TCRβ chain, Clone 830 amino acid sequence | See FIG. 14 |
| 7 | TCRα chain, Clone T53 nucleotide sequence | See FIG. 15 |
| 8 | TCRα chain, Clone T53 amino acid sequence | See FIG. 15 |
| 9 | TCRα chain, Clone A262 nucleotide sequence | See FIG. 16 |
| 10 | TCRα chain, Clone A262 amino acid sequence | See FIG. 16 |
| 11 | TCRα chain, Clone T243 nucleotide sequence | See FIG. 17 |
| 12 | TCRα chain, Clone T243 amino acid sequence | See FIG. 17 |
| 13 | TCRα chain, Clone T262 nucleotide sequence | See FIG. 18 |
| 14 | TCRα chain, Clone T262 amino acid sequence | See FIG. 18 |
| 15 | TCRβ chain, Clone TAK1 nucleotide sequence | See FIG. 19 |
| 16 | TCRβ chain, Clone TAK1 amino acid sequence | See FIG. 19 |
| 17 | CDR1 sequence of TCRα chain, Clone SIG35α nucleotide sequence | GACCGGGGCTCCCAGAGC |
| 18 | CDR1 sequence of TCRα chain, Clone SIG35α amino acid sequence | DRGSQS |
| 19 | CDR1 sequence of TCRβ chain, Clone 794 nucleotide sequence | ATGAACCATGAGTAT |
| 20 | CDR1 sequence of TCRβ chain, Clone 794 amino acid sequence | MNHEY |

TABLE 5-continued

List of Sequences

| SEQ ID NO | NAME OF SEQUENCE | SEQUENCE |
|---|---|---|
| 21 | CDR1 sequence of TCRβ chain, Clone 830 nucleotide sequence | ATGAACCATGAGTAT |
| 22 | CDR 1 sequence of TCRβ chain, Clone 830 amino acid sequence | MNHEY |
| 23 | CDR1 sequence of TCRα chain, Clone T53 nucleotide sequence | GTGACTAACTTTCGAAGC |
| 24 | CDR1 sequence of TCRα chain, Clone T53 amino acid sequence | VTNFRS |
| 25 | CDR1 sequence of TCRα chain, Clone A262 nucleotide sequence | GTGACTAACTTTCGAAGC |
| 26 | CDR1 sequence of TCRα chain, Clone A262 amino acid sequence | VTNFRS |
| 27 | CDR1 sequence of TCRα chain, Clone T243 nucleotid sequence | GTGACTAACTTTCGAAGC |
| 28 | CDR1 sequence of TCRα chain, Clone T243 amino acid sequence | VTNFRS |
| 29 | CDR1 sequence of TCRα chain, Clone T262 nucleotide sequence | GTCAGCGGTTTAAGAGGG |
| 30 | CDR1 sequence of TCRα chain, Clone T262 amino acid sequence | VSGLRG |
| 31 | CDR1 sequence of TCRβ chain, Clone TAK1 nucleotide sequence | AGCGGCCACAGAAGC |
| 32 | CDR1 sequence of TCRβ chain, Clone TAK1 amino acid sequence | SGHRS |
| 33 | CDR2 sequence of TCRα chain, Clone SIG35α nucleotide sequence | ATCTACAGCAACGGCGAC |
| 34 | CDR2 sequence of TCRα chain, Clone SIG35α amino acid sequence | IYSNGD |
| 35 | CDR2 sequence of TCRβ chain, Clone 794 nucleotide sequence | TCAATGAATGTTGAGGTG |
| 36 | CDR2 sequence of TCRβ chain, Clone 794 amino acid sequence | SMNVEV |
| 37 | CDR2 sequence of TCRβ chain, Clone 830 nucleotide sequence | TCAATGAATGTTGAGGTG |
| 38 | CDR 2 sequence of TCRβ chain, Clone 830 amino acid sequence | SMNVEV |
| 39 | CDR2 sequence of TCRα chain, Clone T53 nucleotide sequence | CTAACTTCAAGTGGAATTGAA |
| 40 | CDR2 sequence of TCRα chain, Clone T53 amino acid sequence | LTSSGIE |
| 41 | CDR2 sequence of TCRα chain, Clone A262 nucleotide sequence | CTAACTTCAAGTGGAATTGAA |
| 42 | CDR2 sequence of TCRα chain, Clone A262 amino acid sequence | LTSSGIE |
| 43 | CDR2 sequence of TCRα chain, Clone T243 nucleotide sequence | CTAACTTCAAGTGGAATTGAA |
| 44 | CDR2 sequence of TCRα chain, Clone T243 amino acid sequence | LTSSGIE |

TABLE 5-continued

List of Sequences

| SEQ ID NO | NAME OF SEQUENCE | SEQUENCE |
|---|---|---|
| 45 | CDR2 sequence of TCRα chain, Clone T262 nucleotide sequence | CTGTATTCAGCTGGGGAAGAA |
| 46 | CDR2 sequence of TCRα chain, Clone T262 amino acid sequence | LYSAGEE |
| 47 | CDR2 sequence of TCRβ chain, Clone TAK1 nucleotide sequence | TACTTCAGCGAGACACAG |
| 48 | CDR2 sequence of TCRβ chain, Clone TAK1 amino acid sequence | YFSETQ |
| 49 | CDR3 sequence of TCRα chain, Clone SIG35α nucleotide sequence | TGTGCCGTGTCCATCGGCTTCGGCAACGTGCTGCACTGC |
| 50 | CDR3 sequence of TCRα chain, Clone SIG35α amino acid sequence | CAVSIGFGNVLHC |
| 51 | CDR3 sequence of TCRβ chain, Clone 794 nucleotide sequence | TGTGCCAGCAGTCTACTCGGGGACTATGGCTACACCTTC |
| 52 | CDR3 sequence of TCRβ chain, Clone 794 amino acid sequence | CASSLLGDYGYTF |
| 53 | CDR3 sequence of TCRβ chain, Clone 830 nucleotide sequence | TGTGCCAGCAGTTTAGGGGGTGCCTACGAGCAGTACTTC |
| 54 | CDR 3 sequence of TCRβ chain, Clone 830 amino acid sequence | CASSLGGAYEQYF |
| 55 | CDR3 sequence of TCRα chain, Clone T53 nucleotide sequence | TGTGCTGTGATAACTGGTGGTACTAGCTATGGAAAGCTGACATTT |
| 56 | CDR3 sequence of TCRα chain, Clone T53 amino acid sequence | CAVITGGTSYGKLTF |
| 57 | CDR3 sequence of TCRα chain, Clone A262 nucleotide sequence | TGTGCTGTGCAGAATGCTGGTGGTACTAGCTATGGAAAGCTGACATTT |
| 58 | CDR3 sequence of TCRα chain, Clone A262 amino acid sequence | CAVQNAGGTSYGKLTF |
| 59 | CDR3 sequence of TCRα chain, Clone T243 nucleotide sequence | TGTGCTGTGCTTACCCAAACTGGGGCAAACAACCTCTTCTTT |
| 60 | CDR3 sequence of TCRα chain, Clone T243 amino acid sequence | CAVLTQTGANNLFF |
| 61 | CDR3 sequence of TCRα chain, Clone T262 nucleotide sequence | TGTGCTGTGCAGGCCTTAAGGAATAATGCTGGCAACAACCGTAAGCTGATTTGG |
| 62 | CDR3 sequence of TCRα chain, Clone T262 amino acid sequence | CAVQALRNNAGNNRKLIW |
| 63 | CDR3 sequence of TCRβ chain, Clone TAK1 nucleotide sequence | TGTGCCTCTTCTCTGGGCTGGCGGGAAACCTACAACGAGCAGTTCTTC |
| 64 | CDR3 sequence of TCRβ chain, Clone TAK1 amino acid sequence | CASSLGWRETYNEQFF |
| 65 | Furin recognition nucleotide sequence | AGGGCCAAGAGA |
| 66 | Furin recognition amino acid sequence | RAKR |
| 67 | SGSG linker nucleotide sequence | TCTGGATCTGGC |
| 68 | SGSG linker amino acid sequence example | SGSG |

TABLE 5-continued

List of Sequences

| SEQ ID NO | NAME OF SEQUENCE | SEQUENCE |
|---|---|---|
| 69 | F2A nucleotide sequence | GCCCCTGTGAAGCAGACCCTGAACTTCGACCT GCTGAAGCTGGCCGGCGACGTGGAAAGCAAC CCTGGCCCC |
| 70 | F2A amino acid sequence | APVKQTLNFDLLKLAGDVESNPGP |
| 71 | Δ NGFR nucleotide sequence | ATGGACGGGCCGCGCCTGCTGCTGTTGCTGC TTCTGGGGGTGTCCCTTGGAGGTGCCAAGGA GGCATGCCCCACAGGCCTGTACACACACAGC GGTGAGTGCTGCAAAGCCTGCAACCTGGGCG AGGGTGTGGCCCAGCCTTGTGGAGCCAACCA GACCGTGTGTGAGCCCTGCCTGGACAGCGTG ACGTTCTCCGACGTGGTGAGCGCGACCGAGC CGTGCAAGCCGTGCACCGAGTGCGTGGGGCT CCAGAGCATGTCGGCGCCATGCGTGGAGGCC GACGACGCCGTGTGCCGCTGCGCCTACGGCT ACTACCAGGATGAGACGACTGGGCGCTGCGA GGCGTGCCGCGTGTGCGAGGCGGGCTCGGG CCTCGTGTTCTCCTGCCAGGACAAGCAGAACA CCGTGTGCGAGGAGTGCCCCGACGGCACGTA TTCCGACGAGGCCAACCACGTGGACCCGTGC CTGCCCTGCACCGTGTGCGAGGACACCGAGC GCCAGCTCCGCGAGTGCACACGCTGGGCCGA CGCCGAGTGCGAGGAGATCCCTGGCCGTTGG ATTACACGGTCCACACCCCAGAGGGCTCGGA CAGCACAGCCCCAGCACCCAGGAGCTGAG GCACCTCCAGAACAAGACCTCATAGCCAGCAC GGTGGCAGGTGTGGTGACCACAGTGATGGGC AGCTCCCAGCCCGTGGTGACCCGAGGCACCA CCGACAACCTCATCCCTGTCTATTGCTCCATCC TGGCTGCTGTGGTTGTGGGTCTTGTGGCCTAC ATAGCCTTCAAGAGGTGGAACAGC |
| 72 | Δ NGFR amino acid sequence | MDGPRLLLLLLLGVSLGGAKEACPTGLYTHSGEC CKACNLGEGVAQPCGANQTVCEPCLDSVTFSDV VSATEPCKPCTECVGLQSMSAPCVEADDAVCRC AYGYYQDETTGRCEACRVCEAGSGLVFSCQDK QNTVCEECPDGTYSDEANHVDPCLPCTVCEDTE RQLRECTRWADAECEEIPGRWITRSTPPEGSDS TAPSTQEPEAPPEQDLIASTVAGVVTTVMGSSQP VVTRGTTDNLIPVYCSILAAVVVGLVAYIAFKRWN S |
| 73 | MART$_{127-35}$ peptide | AAGIGILTV |
| 74 | WT1$_{235-243}$ heteroclitic peptide | CYTWNQMNL |
| 75 | TRBV27 specific forward primer | 5'-ATCCCAGTGTGGTGGTACGGGAATTCTGCCAT GGGCCCCCAGCTCCTTGGC-3' |
| 76 | β constant region specific reverse primers, 3'-cβ-1 | 5'-ATCGTCGACCACTGTGCTGGCGGCCGCTCGA GTTCCAGGGCTGCCTTCAGAAATCC-3' |
| 77 | β constant region specific reverse primers, 3'-Cβ-2 | 5'-GACCACTGTGCTGGCGGCCGCTCGAGCTAGC CTCTGGAATCCTTTCTCTTGACCATTGC-3' |
| 78 | 3'-TCRα UTR region primer | 5'-GGAGAGTT000TCTGTTTGGAGAG-3' |
| 79 | modified 5'-RACE primer | 5'-GTGTGGTGGTACGGGAATTCAAGCAGTGGTAT CAACGCAGAGT-3' |
| 80 | 3'-TCRα constant region primer | 5'-ACCACTGTGCTGGCGGCCGCTCAGCTGGACC ACAGCCGCAGCG-3' |
| 81 | Paired TCRβ chain of CR3 sequence of SIG35 α amino acid sequence from healthy donor, clone 5H9 | CASSLLGGSTDTQYF |

TABLE 5-continued

List of Sequences

| SEQ ID NO | NAME OF SEQUENCE | SEQUENCE |
|---|---|---|
| 82 | Paired TCRβ chain of CR3 sequence of SIG35 α amino acid sequence from Patient A, clone 4C8 | CASSPIDGLNTEAFF |
| 83 | Paired TCRβ chain of CR3 sequence of SIG35 α amino acid sequence from Patient B, clone 31 | CASSFNDEQFF |
| 84 | Paired TCRβ chain of CR3 sequence of SIG35 α amino acid sequence from Patient C, clone 31 | CASSPSQGGNTEAFF |
| 85 | Paired TCRβ chain of CR3 sequence of SIG35 α amino acid sequence from Patient C, clone 16 | CASSDSTASSEQFF |
| 86 | Paired TCRβ chain of CR3 sequence of SIG35 α amino acid sequence from Patient D, clone 29 | CASSLSGSGDEQFF |
| 87 | CDR3 sequence of TCRβ chain, DMFS amino acid | CASSLSFGTEAFF |
| 88 | CDR3 sequence of TCRβ chain, Clone 1086 amino acid | CASSLHGPGGYTF |
| 89 | CDR3 sequence of TCRβ chain, Clone 788 amino acid | CASGPSYEQYF |
| 90 | CDR3 sequence of TCRβ chain, Clone 523 amino acid | CASGSYEQYF |
| 91 | CDR3 sequence of TCRβ chain, Clone 413 amino acid | CASSVFGGDMGEKLFF |
| 92 | CDR3 sequence of TCRα chain, Clone TAK1 amino acid sequence | CAVQAVDSNYQLIW |
| 93 | TCRβ chain, Clone 8H nucleotide sequence | See FIG. 28 |
| 94 | TCRβ chain, Clone 8H amino acid sequence | See FIG. 28 |
| 95 | TCRβ chain, Clone 7Q nucleotide sequence | See FIG. 29 |
| 96 | TCRβ chain, Clone 7Q amino acid sequence | See FIG. 29 |
| 97 | TCRβ chain, Clone 9J nucleotide sequence | See FIG. 30 |
| 98 | TCRβ chain, Clone 9J amino acid sequence | See FIG. 30 |
| 99 | CDR1 sequence of TCRβ chain, Clone 8H nucleotide sequence | ATGAACCATGAGTAT |
| 100 | CDR1 sequence of TCRβ chain, Clone 8H amino acid sequence | MNHEY |
| 101 | CDR1 sequence of TCRβ chain, Clone 7Q nucleotide sequence | ATGAACCATGAGTAT |
| 102 | CDR1 sequence of TCRβ chain, Clone 7Q amino acid sequence | MNHEY |

TABLE 5-continued

List of Sequences

| SEQ ID NO | NAME OF SEQUENCE | SEQUENCE |
|---|---|---|
| 103 | CDR1 sequence of TCRβ chain, Clone 9J nucleotide sequence | TCTGGGCATAGGAGT |
| 104 | CDR1 sequence of TCRβ chain, Clone 9J amino acid sequence | SGHRS |
| 105 | CDR2 sequence of TCRβ chain, Clone 8H nucleotide sequence | TCAATGAATGTTGAGGTG |
| 106 | CDR2 sequence of TCRβ chain, Clone 8H amino acid sequence | SMNVEV |
| 107 | CDR2 sequence of TCRβ chain, Clone 7Q nucleotide sequence | TCAATGAATGTTGAGGTG |
| 108 | CDR2 sequence of TCRβ chain, Clone 7Q amino acid sequence | SMNVEV |
| 109 | CDR2 sequence of TCRβ chain, Clone 9J nucleotide sequence | TACTTCAGTGAGACACAG |
| 110 | CDR2 sequence of TCRβ chain, Clone 9J amino acid sequence | YFSETQ |
| 111 | CDR3 sequence of TCRβ chain, Clone 8H nucleotide sequence | TGTGCCAGCAGTCCCCTGGGGGCCATGGAGCAGTACTTC |
| 112 | CDR3 sequence of TCRβ chain, Clone 8H amino acid sequence | CASSPLGAMEQYF |
| 113 | CDR3 sequence of TCRβ chain, Clone 7Q nucleotide sequence | TGTGCCAGCAGTCCCTACATGATGAACACTGAAGCTTTCTTT |
| 114 | CDR3 sequence of TCRβ chain, Clone 7Q amino acid sequence | CASSPYMMNTEAFF |
| 115 | CDR3 sequence of TCRβ chain, Clone 9J nucleotide sequence | TGCGCCAGCAGCTGGACAGGGGATGGCTACACCTTC |
| 116 | CDR3 sequence of TCRβ chain, Clone 9J amino acid sequence | CASSWTGDGYTF |
| 117 | Paired TCRβ chain of CR3 sequence of SIG35 α amino acid sequence from Clone 4K | CASSHGGNEQYF |
| 118 | Paired TCRβ chain of CR3 sequence of SIG35 α amino acid sequence from Clone 7E | CASSRDFGNTIYF |
| 119 | Paired TCRβ chain of CR3 sequence of SIG35 α amino acid sequence from Clone 9I | CASSLAMGATEAFF |
| 120 | Paired TCRβ chain of CR3 sequence of SIG35 α amino acid sequence from Clone 6X | CATGVTDTQYF |
| 121 | Paired TCRβ chain of CR3 sequence of SIG35 α amino acid sequence from Clone 6B | CASSEVAWQFF |
| 122 | Paired TCRβ chain of CR3 sequence of SIG35 α amino acid sequence from Clone 11C | CASDEGFGYTF |
| 123 | Furin concensus motif | RX(K/R)R |
| 124 | Glycine serine linker | GGSG |

TABLE 6

Sequencing results of TCRβ chains isolated from A2/MART1 multimer+ CD4+ T cells

| | Donor #7 (A2+) | | Donor #3 (A2−) | |
|---|---|---|---|---|
| Vb subtype | Number of unique clonotypes | Number of isolates sequenced | Number of unique clonotypes | Number of isolates sequenced |
| TRBV2 | 7 | 42 | 7 | 36 |
| TRBV5-1 | 11 | 19 | 11 | 31 |
| TRBV27 | 13 | 29 | 13 | 30 |

TABLE 7

Functional and structural avidities of Jurkat 76 cells reconstituted with A2/MART1 TCRs

| Clone | Donor | aAPC used for stimulation | TRBV | CDR3b | TRBJ | Functional avidity* without CD8 EC50 (mg/ml) | Functional avidity with CD8 EC50 (mg/ml) | Structural avidity† without CD8 EC50 (mg/ml) | Structural avidity with CD8 EC50 (mg/ml) |
|---|---|---|---|---|---|---|---|---|---|
| CI.8H | #3 (A2−) | mutA2-aAPC/IL-21 | 27 | CASSPLGAMEQYF (SEQ ID NO: 112) | 2-7 | 0.063 | 0.040 | 0.014 | 0.008 |
| CI.7Q | #3 (A2−) | mutA2-aAPC/IL-21 | 27 | CASSPYMMNTEAFF (SEQ ID NO: 114) | 1-1 | 0.065 | 0.043 | 0.016 | 0.009 |
| CI.9J | #3 (A2−) | mutA2-aAPC/IL-21 | 5-1 | CASSVVTGDGYTF (SEQ ID NO: 116) | 1-2 | 0.075 | 0.071 | 0.018 | 0.010 |
| C1.4K | #7 (A2+) | mutA2-aAPC/IL-21 | 5-1 | CASSHGGNEQYF (SEQ ID NO: 117) | 2-7 | 0.083 | 0.080 | 0.018 | 0.011 |
| CI.7E | #3 (A2−) | mutA2-aAPC/IL-21 | 27 | CASSRDFGNTIYF (SEQ ID NO: 118) | 1-3 | 0.102 | 0.071 | 0.010 | 0.006 |
| CI.9I | #3 (A2−) | mutA2-aAPC/IL-21 | 5-1 | CASSLAMGATEAFF (SEQ ID NO: 119) | 1-1 | 0.140 | 0.097 | 0.025 | 0.013 |
| CI.6X | #7 (A2+) | mutA2-aAPC/IL-21 | 2 | CATGVTDTQYF (SEQ ID NO: 120) | 2-3 | 0.150 | 0.083 | 0.039 | 0.018 |
| DMF5 | — | — | 6-4 | CASSLSFGTEAFF (SEQ ID NO: 87) | 1-1 | 0.363 | 0.102 | 0.022 | 0.013 |
| CI.6B | #7 (A2+) | mutA2-aAPC/IL-21 | 2 | CASSEVAWQFF (SEQ ID NO: 121) | 2-1 | 0.600 | 0.120 | 0.044 | 0.013 |
| CI.11C | #3 (A2−) | mutA2-aAPC/IL-21 | 2 | CASDEGFGYTF (SEQ ID NO: 122) | 1-2 | 2.460 | 0.292 | 0.108 | 0.018 |

*Functional avidity, expressed as EC50 in mg/ml, was defined as the concentration of peptide required to achieve 50% of maximal response.
†Structural avidity, expressed as EC50 in mg/ml, was defined as the concentration of A2/MART1 multimer required to achieve half maximal multimer staining.

REFERENCES

Kunert A et al. Front Immunol. 2013 Nov. 8; 4:363
Hinrichs C S, et al. Immunol Rev. 2014 January; 257(1): 56-71
Li et al 2005 Nature Biotechnology 23 349-354.
Dietrich et al., 2003, J Immunol. 15; 170(10):5103-9.
Trautmann et al., 2002, Eur J Immunol. November; 32(11): 3181-90.
Wei et al., Immunogenetics. 1994; 40(1):27-36.
Imataki et al, J Immunol. 2012 Feb. 15; 188(4):1609-19.
Schultz E S, Lethé B, Cambiaso C L, Van Snick J, Chaux P, Corthals J, Heirman C, Thielemans K, Boon T, van der Bruggen P. A MAGE-A3 peptide presented by HLA-DP4 is recognized on tumor cells by CD4+ cytolytic T lymphocytes. *Cancer Res* 2000; 60: 6272-6275. (PMID: 11103782)
Vigneron N, Ooms A, Morel S, Ma W, Degiovanni G, Van den Eynde B. A peptide derived from melanocytic protein gp100 and presented by HLA-B35 is recognized by autologous cytolytic T lymphocytes on melanoma cells. *Tissue Antigens* 2005; 65: 156-162. (PMID: 15713214)
Tomita Y, Imai K, Senju S, Irie A, Inoue M, Hayashida Y, Shiraishi K, Mori T, Daigo Y, Tsunoda T, Ito T, Nomori H, Nakamura Y, Kohrogi H, Nishimura Y. A novel tumor-associated antigen, cell division cycle 45-like can induce cytotoxic T-lymphocytes reactive to tumor cells. *Cancer Sci* 2011; 102: 697-705. (PMID: 21231984)
Vigneron N, Van den Eynde B J. Proteasome subtypes and the processing of tumor antigens: increasing antigenic diversity. *Curr. Opin Immunol* 2012; 24: 84-91. (PMID: 22206698)
Ma W, Vigneron N, Chapiro J, Stroobant V, Germeau C, Boon T, Coulie P G, Van den Eynde B J. A MAGE-C2 antigenic peptide processed by the immunoproteasome is recognized by cytolytic T cells isolated from a melanoma patient after successful immunotherapy. *Int J Cancer* 2011; 129: 2427-2434. (PMID: 21207413)
Corbière V, Chapiro J, Stroobant V, Ma W, Lurquin C, Lethé B, van Baren N, Van den Eynde B J, Boon T, Coulie P G. Antigen spreading contributes to MAGE vaccination-induced regression of melanoma metastases. *Cancer Res* 2011; 71: 1253-1262. (PMID: 21216894)
Dalet A, Stroobant V, Vigneron N, Van den Eynde B J. Differences in the production of spliced antigenic peptides by the standard proteasome and the immunoproteasome. *Eur J Immunol.* 2011; 41: 39-46. (PMID: 21182075)

Chapiro J, Claverol S, Piette F, Ma W, Stroobant V, Guillaume B, Gairin J-E, Morel S, Burlet-Schiltz O, Monsarrat B, Boon T, Van den Eynde B. Destructive cleavage of antigenic peptides either by the immunoproteasome or by the standard proteasome results in differential antigen presentation. *J Immunol* 2006; 176: 1053-1061. (PMID: 16393993)

Guillaume B, Chapiro J, Stroobant V, Colau D, Van Holle B, Parvizi G, Bousquet-Dubouch M P, Theate I, Parmentier N, Van den Eynde B J. Two abundant proteasome subtypes that uniquely process some antigens presented by HLA class I molecules. *Proc Natl Acad Sci USA* 2010; 107: 18599-18604. (PMID: 20937868)

Dalet A, Robbins P F, Stroobant V, Vigneron N, Li Y F, E I-Gamil M, Hanada K, Yang J C, Rosenberg S A, Van den Eynde B J. An antigenic peptide produced by reverse splicing and double asparagine deamidation. *Proc Natl Acad Sci USA* 2011; 108: E323-331. (PMID: 21670269)

Vigneron N, Stroobant V, Chapiro J, Ooms A, Degiovanni G, Morel S, van der Bruggen P, Boon T, Van den Eynde B. An antigenic peptide produced by peptide splicing in the proteasome. *Science* 2004; 304: 587-590. (PMID: 15001714)

Skipper J C A, Hendrickson R C, Gulden P H, Brichard V, Van Pel A, Chen Y, Shabanowitz J, Wölfel T, Slingluff C L, Jr, Boon T, Hunt D F, Engelhard V H. An HLA-A2-restricted tyrosinase antigen on melanoma cells results from posttranslational modification and suggests a novel pathway for processing of membrane proteins. *J Exp Med* 1996; 183: 527-534. (PMID: 8627164)

Hanada K, Yewdell J W, Yang J C. Immune recognition of a human renal cancer antigen through posttranslational protein splicing. *Nature* 2004; 427: 252-256. (PMID: 14724640)

Chaux P, Vantomme V, Stroobant V, Thielemans K, Corthals J, Luiten R, Eggermont A M, Boon T, van der Bruggen P. Identification of MAGE-3 epitopes presented by HLA-DR molecules to CD4[+] T lymphocytes. *J Exp Med* 1999; 189: 767-777. (PMID: 10049940)

Zarour H M, Storkus W J, Brusic V, Williams E, Kirkwood J M. NY-ESO-1 encodes DRB1*0401-restricted epitopes recognized by melanoma-reactive CD4+ T cells. *Cancer Res* 2000; 60: 4946-4952. (PMID: 10987311)

Parkhurst, Clin Cacer Res 15:169, 2009

Theoret, Hum Gene Ther, 19:1219. 2008

Kung P, Goldstein G, Reinherz E L, Schiossman S F. Monoclonal antibodies defining distinctive human T cell surface antigens. Science, Volume 206, pp 347-349 (1979)

Barker et al. Blood 115:1843-9 (2010),

Hague et al. Blood 110:1123-31 (2007).

Li et al., Nature Med. 16:1029-34 2010.

---

What is claimed is:

1. A method for obtaining a recombinant cell expressing a TCR specific for a peptide of interest comprising:
   a. transducing a cell population comprising cells expressing an endogenous prey TCR polypeptide chain with a bait nucleic acid encoding an exogenous bait TCR polypeptide chain, wherein the bait TCR polypeptide chain in combination with a counterchain TCR polypeptide can constitute a parent TCR that specifically binds said peptide of interest, wherein the counterchain TCR polypeptide is not the endogenous prey TCR polypeptide chain;
   b. culturing the transduced cell population under conditions that permit the bait TCR polypeptide chain to be expressed;
   c. i) obtaining a recombinant cell expressing a TCR comprising the bait TCR polypeptide chain and the prey TCR polypeptide chain that selectively binds said peptide of interest from the transduced cell population obtained in step (b), the obtaining comprising measuring the avidity and/or affinity of the TCR comprising the bait TCR polypeptide chain and the prey TCR polypeptide chain, and selecting the recombinant cell wherein the TCR has increased avidity and/or affinity for the peptide of interest compared to a preselected standard;

ii) isolating a prey nucleic acid encoding the prey TCR polypeptide chain from the cell obtained in step (c)(i); and iii) introducing the isolated prey nucleic acid and the bait nucleic acid into a cell able to express a TCR or differentiate into a cell able to express a TCR under conditions that permit the TCR polypeptide chains to be expressed.

2. The method of claim 1, wherein the step of obtaining the recombinant cell expressing a TCR comprising the bait TCR polypeptide chain and the prey TCR polypeptide chain that selectively binds said peptide of interest from the transduced cell population obtained in step (b) comprises isolating one or more cells of the cell population that express the transduced bait TCR polypeptide chain and which bind the peptide of interest.

3. The method of claim 1, wherein the prey nucleic acid is isolated by cloning the prey nucleic acid.

4. The method of claim 1, wherein the prey TCR polypeptide chain comprises a CDR3 region comprising at least one amino acid modification relative to the CDR3 region of the cognate polypeptide chain in the parent TCR.

5. The method of claim 1, wherein the bait TCR polypeptide chain was previously isolated from a T cell recognizing said peptide of interest.

6. The method of claim 1, wherein the step of obtaining the recombinant cell expressing the TCR comprises the step of culturing the transduced cell population with an antigen presenting cell presenting the peptide of interest.

7. The method of claim 1, wherein the step of obtaining the recombinant cell expressing the TCR specific for a peptide of interest from the transduced cell population comprises using cell sorting.

8. The method of claim 1, wherein the bait TCR polypeptide chain was expressed and previously isolated from a T cell recognizing the peptide of interest.

9. The method of claim 1, wherein the cell population is a population of peripheral blood mononuclear cells (PBMCs).

10. The method of claim 1, wherein the bait nucleic acid transduced into said cell population in step (a) encodes a TCR alpha chain or a TCR beta chain.

11. The method of claim 1, wherein the bait nucleic acid transduced into said cell population in step (a) encodes a TCR chain which predominantly contributes to peptide recognition by a TCR.

12. The method of claim 1, wherein the transduction is repeated a second, third, fourth, fifth and/or sixth time.

13. The method of claim 1, wherein the cell population or cell is also transduced with an antisense molecule for suppressing expression of an endogenous TCR chain.

14. The method of claim 1, wherein the bait nucleic acid is codon optimized.

15. The method of claim 1, wherein the bait nucleic acid transduced into said cell population in step (a) encodes a TCR delta chain or a TCR gamma chain.

16. The method of claim 7, wherein the cell sorting is fluorescence-activated cell sorting.

17. The method of claim 9, wherein the PBMCs are PBMCs activated with a CD3 ligand.

* * * * *